US011619636B2

United States Patent
Ford et al.

(10) Patent No.: US 11,619,636 B2
(45) Date of Patent: Apr. 4, 2023

(54) MASS SPECTROMETRY ASSAY METHOD FOR DETECTION AND QUANTITATION OF KIDNEY FUNCTION METABOLITES

(71) Applicant: Metabolon, Inc., Morrisville, NC (US)

(72) Inventors: Lisa Ford, Durham, NC (US); Tiffany A. Freed, Apex, NC (US); Deirdre M. Hauser, Hillsborough, NC (US); Kelli Goodman, Raleigh, NC (US)

(73) Assignee: Metabolon, Inc., Morrisville, NC (US)

( * ) Notice: Subject to any disclaimer, the term of this patent is extended or adjusted under 35 U.S.C. 154(b) by 184 days.

(21) Appl. No.: 16/466,451

(22) PCT Filed: Dec. 14, 2017

(86) PCT No.: PCT/US2017/066364
§ 371 (c)(1),
(2) Date: Jun. 4, 2019

(87) PCT Pub. No.: WO2018/118630
PCT Pub. Date: Jun. 28, 2018

(65) Prior Publication Data
US 2019/0346455 A1   Nov. 14, 2019

Related U.S. Application Data

(60) Provisional application No. 62/435,967, filed on Dec. 19, 2016, provisional application No. 62/526,043, (Continued)

(51) Int. Cl.
*G01N 33/68* (2006.01)
*G01N 30/72* (2006.01)
(Continued)

(52) U.S. Cl.
CPC ..... *G01N 33/6848* (2013.01); *G01N 30/7233* (2013.01); *G01N 33/62* (2013.01);
(Continued)

(58) Field of Classification Search
USPC .......................................... 436/173
See application file for complete search history.

(56) References Cited

U.S. PATENT DOCUMENTS

2009/0194685 A1   8/2009 Corr et al.
2012/0164741 A1   6/2012 Chen et al.
(Continued)

FOREIGN PATENT DOCUMENTS

CN      102680599 A      9/2012
CN      104897821 A      9/2015
(Continued)

OTHER PUBLICATIONS

Zhou, H. et al. Rapid detection and quantification of apolipoprotein L1 genetic variants and total levels in plasma by ultra-performance liquid chromatography/tandem mass spectrometry, Rapid Commun. Mass Spectrom. 2013, 27, 2639-2647 (Year: 2013).*

(Continued)

*Primary Examiner* — Xiaoyun R Xu
(74) *Attorney, Agent, or Firm* — NK Patent Law

(57) ABSTRACT

A method for determining in a sample, by mass spectrometry, the amount of one or more analytes selected from the group consisting of N-acetylthreonine, TMAP, phenylacetylglutamine, tryptophan, creatinine, meso-erythritol, arabitol, myo-inositol, N-acetyl serine, N-acetylalanine, 3-methylhistidine, trans-4-hydroxyproline, kynurenine, urea, C-glycosyltryptophan, 3-indoxyl sulfate, pseudouridine, and combinations thereof is described. The method comprises subjecting the sample to an ionization source under conditions suitable to produce one or more ions detectable by mass spectrometry from each of the one or more of the analytes; measuring, by mass spectrometry, the amount of the one or more ions from each of the one or more analytes; and using the measured amount of the one or more ions to determine the amount of each of the one or more (Continued)

analytes in the sample. Also described is a kit comprising one or more isotopically labeled analogues as internal standards for each of the one or more analytes.

12 Claims, 25 Drawing Sheets

Related U.S. Application Data filed on Jun. 28, 2017, provisional application No. 62/558,014, filed on Sep. 13, 2017.

(51) Int. Cl.
*G01N 33/62* (2006.01)
*G01N 33/70* (2006.01)
*H01J 49/00* (2006.01)
*H01J 49/14* (2006.01)

(52) U.S. Cl.
CPC ............ *G01N 33/70* (2013.01); *H01J 49/005* (2013.01); *H01J 49/0009* (2013.01); *H01J 49/0031* (2013.01); *H01J 49/145* (2013.01)

(56) References Cited

U.S. PATENT DOCUMENTS

| | | | |
|---|---|---|---|
| 2014/0343865 A1 | 11/2014 | Brown et al. | |
| 2014/0364337 A1 | 12/2014 | Hermanson et al. | |
| 2015/0362510 A1* | 12/2015 | Gall | G01N 33/5308 435/7.92 |
| 2016/0116486 A1 | 4/2016 | Perichon et al. | |
| 2016/0195547 A1 | 7/2016 | Cohen et al. | |
| 2016/0282371 A1 | 9/2016 | Huang et al. | |
| 2016/0349221 A1 | 12/2016 | Goldman et al. | |

FOREIGN PATENT DOCUMENTS

| | | |
|---|---|---|
| CN | 105738626 A | 7/2016 |
| JP | 2009222421 A | 10/2009 |
| JP | 2011511276 A | 4/2011 |
| JP | 2016520192 A | 7/2016 |
| WO | 2010126146 A1 | 11/2010 |
| WO | 2014186311 A1 | 11/2014 |
| WO | 2016025429 A1 | 2/2016 |
| WO | 2018118630 A1 | 6/2018 |

OTHER PUBLICATIONS

Creek, D.J. et al. Toward Global Metabolomics Analysis with Hydrophilic Interaction Liquid Chromatography-Mass Spectrometry: Improved Metabolite Identification by Retention Time Prediction, Analytical Chemistry, 2011, 83, 8703-8710 (Year: 2011).*

EPO; Partial Supplementary European Search Report for European Patent Application No. 17885159.8 dated Jul. 3, 2020, 16 pages.
Takahashi, N., et al., "Tandem mass spectrometry measurements of creatinine in mouse plasma and urine for determining glomerular filtration rate" International Society of Nephrology, Kidney International, vol. 71, Issue 3, Feb. 2007, pp. 266-271.
Solini, Anna, et al., "Prediction of Declining Renal Function and Albuminuria in Patients With Type 2 Diabetes by Metabolomics", The Journal of Clinical Endocrinology and Metabolism, Feb. 2016, vol. 101, No. 2, pp. 696-704.
Guay, Vincent, "Material Safety Data Sheet: Sheet No. 250", CDN Isotopes Flyer, Jan. 2014, 2 pages, XP055699855.
ISA/US; International Search Report and Written Opinion for International Patent Application No. PCT/US17/66364 dated Mar. 5, 2018, 13 pages.
WIPO; International Preliminary Report on Patentability for International Patent Application No. PCT/US2017/066364 dated Jun. 25, 2019, 11 pages.
EPO; Extended European Search Report for European Patent Application No. 17885159.8 dated Oct. 5, 2020, 14 pages.
EPO; Communication pursuant to Rules 70(2) and 70a(2) EPC for European Patent Application No. 17885159.8 dated Oct. 22, 2020, 1 page.
CNIPA; Office Action for Chinese Patent Application No. 201780078615.8 dated Jul. 6, 2021, 23 pages.
JPO; Office Action for Japanese Patent Application No. 2019-553158 dated Oct. 5, 2021, 6 pages.
"Direct analysis of free amino acid in foods by atmospheric pressure chemical ionization LC / MS, applications", Agilent Technologies, Oct. 27, 2006, 12 pages. Translation Included.
JPO; Decision of Rejection for Japanese Patent Application No. 2019-553158 dated Jan. 13, 2022, 5 pages.
IP Australia; Office Action for Australian Patent Application No. 2017382744 dated Feb. 22, 2022, 5 pages.
CNIPA; Office Action for Chinese Patent Application No. 201780078615.8 dated May 30, 2022, 12 pages.
EPO; Communication pursuant to Article 94(3) EPC for European Patent Application No. 17885159.8 dated Jul. 28, 2022, 7 pages.
JPO; Re-examination Report for Japanese Patent Application No. 2019-553158 dated Jul. 25, 2022, 2 pages.
Fuertig, René, et al., "LC-MS/MS-based quantification of kynurenine metabolites, tryptophan, monoamines and neopterin in plasma, cerebrospinal fluid and brain", Bioanallysis, Methodology, 2016, vol. 8, No. 18, 15 pages.
IP Australia; Office Action for Australian Patent Application No. 2017382744 dated Dec. 16, 2022, 4 pages.
IP Australia; Examination Report for Australian Patent Application No. 2017382744 dated Oct. 25, 2022, 6 pages.
CNIPA; Rejection Decision for Chinese Patent Application No. 201780078615.8 dated Nov. 3, 2022, 11 pages.

* cited by examiner

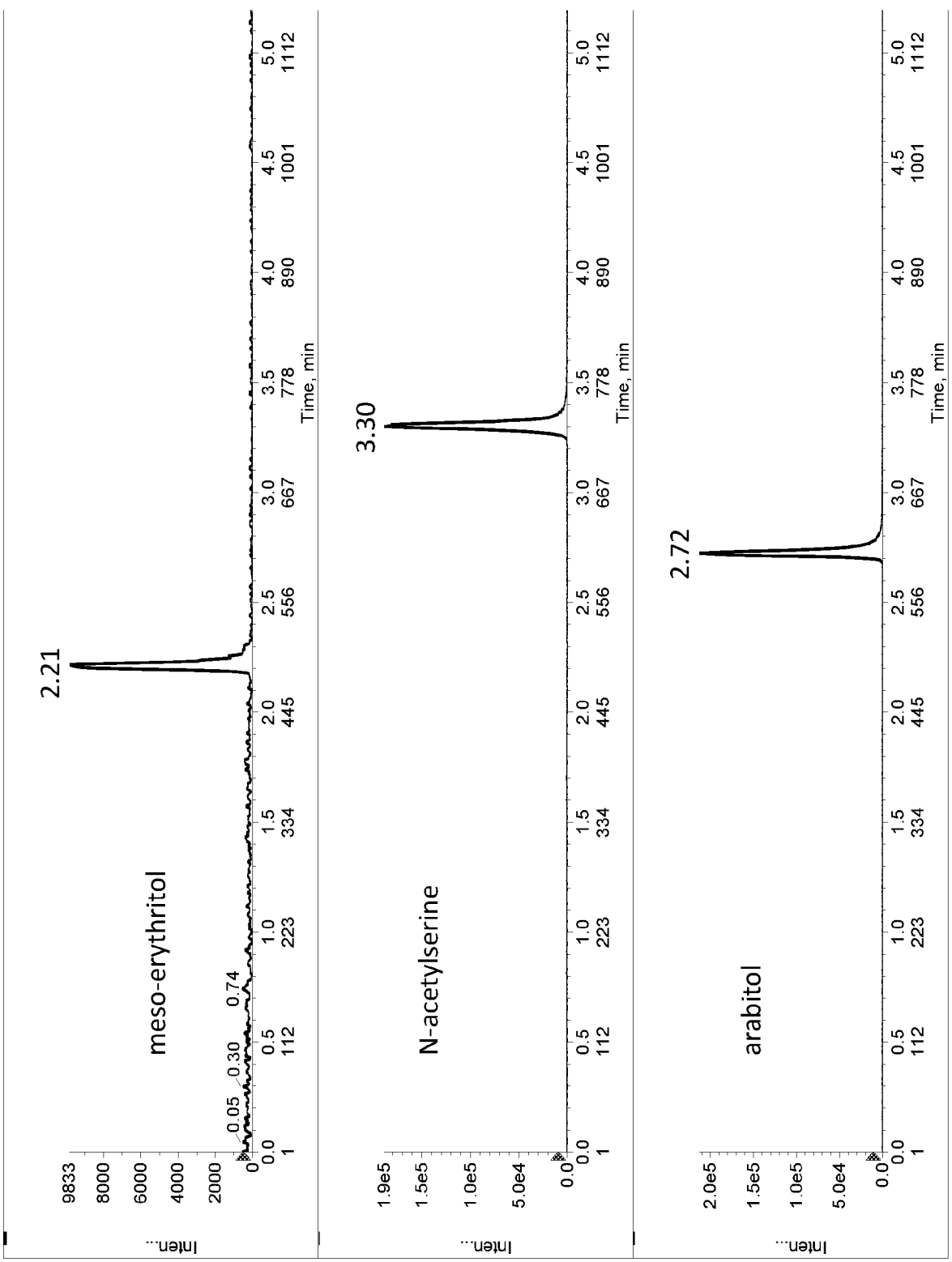

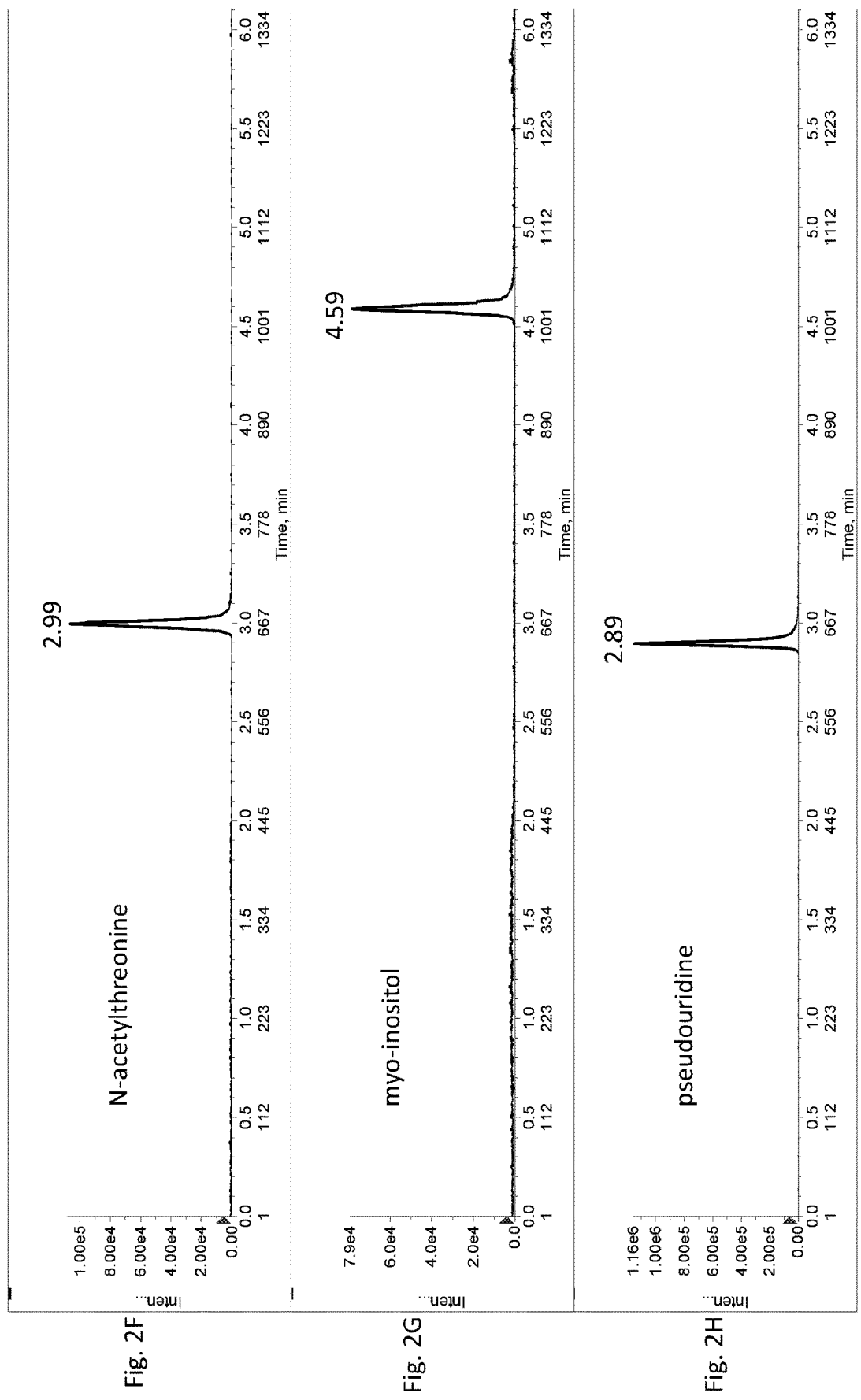

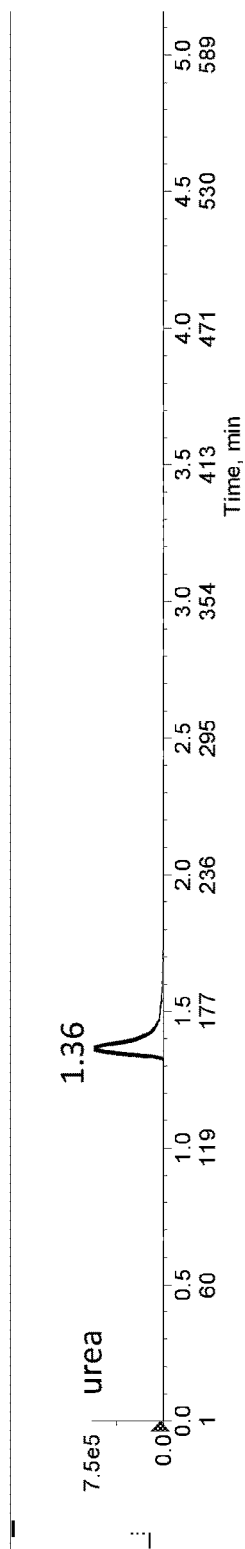
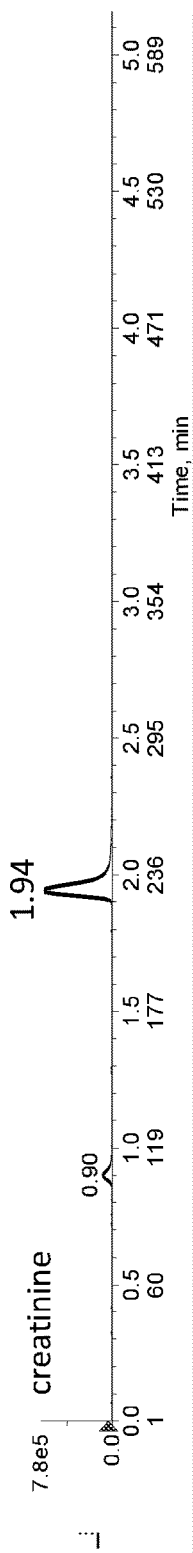
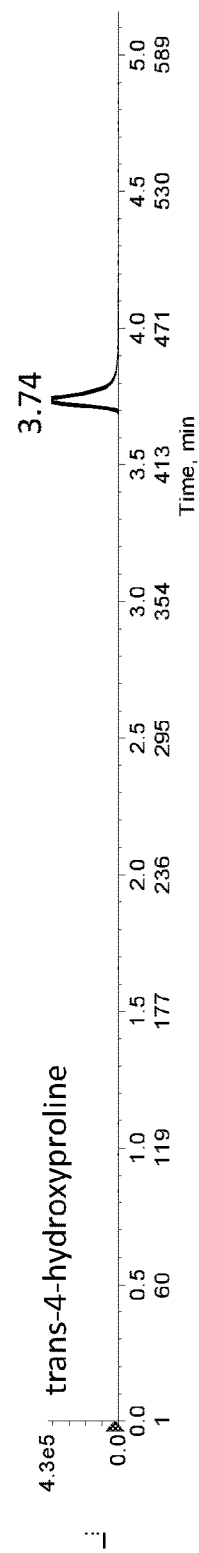
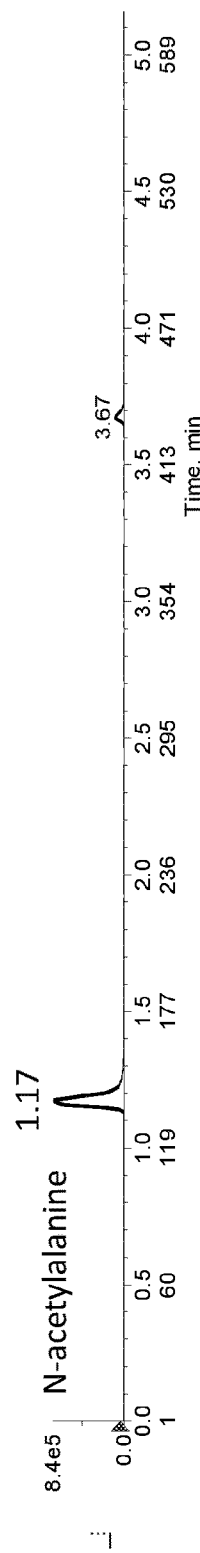
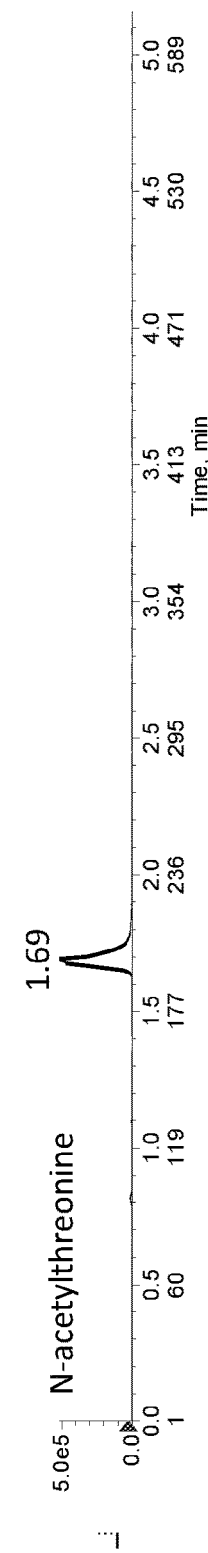
Fig. 3C
Fig. 3D
Fig. 3E
Fig. 3F
Fig. 3G

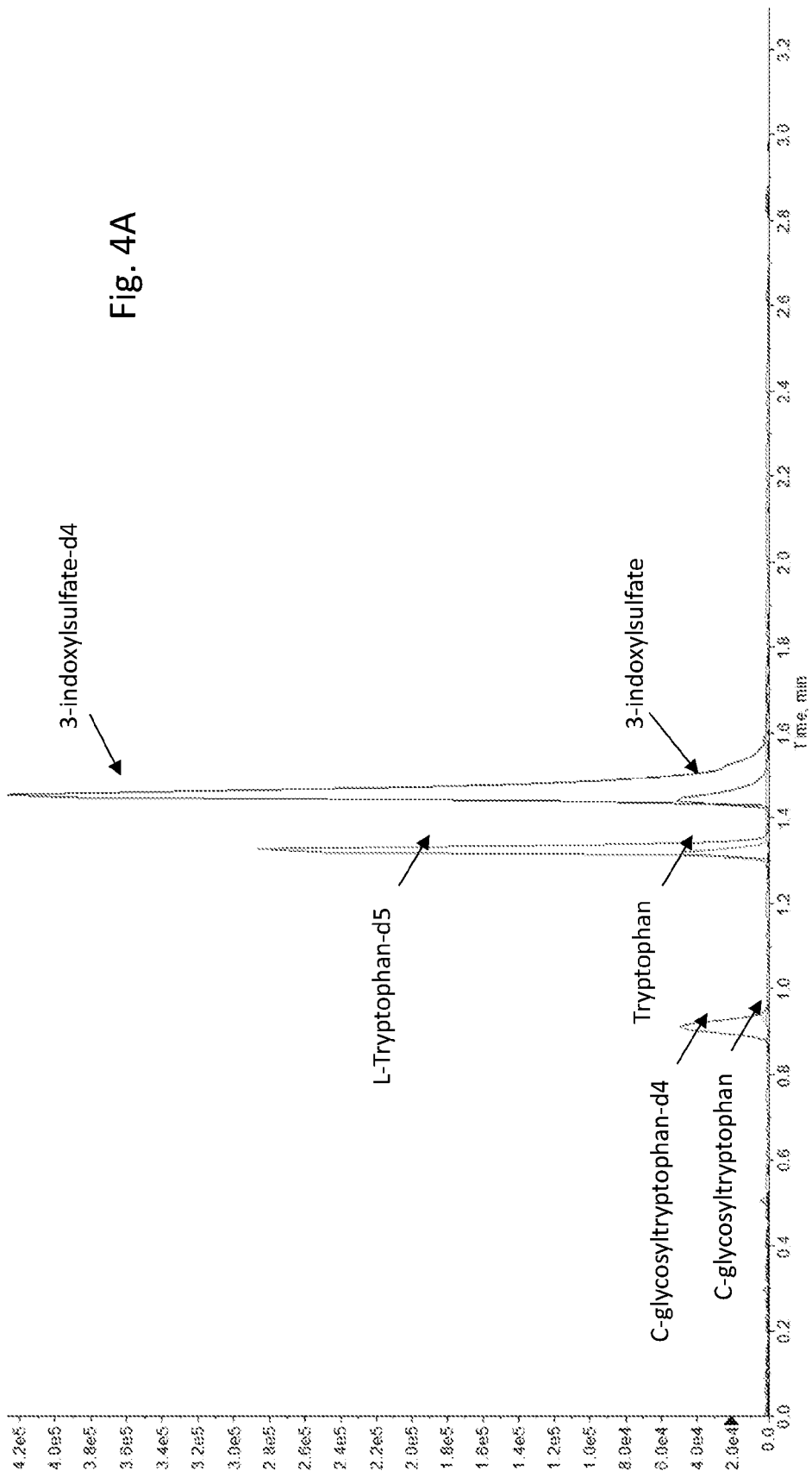

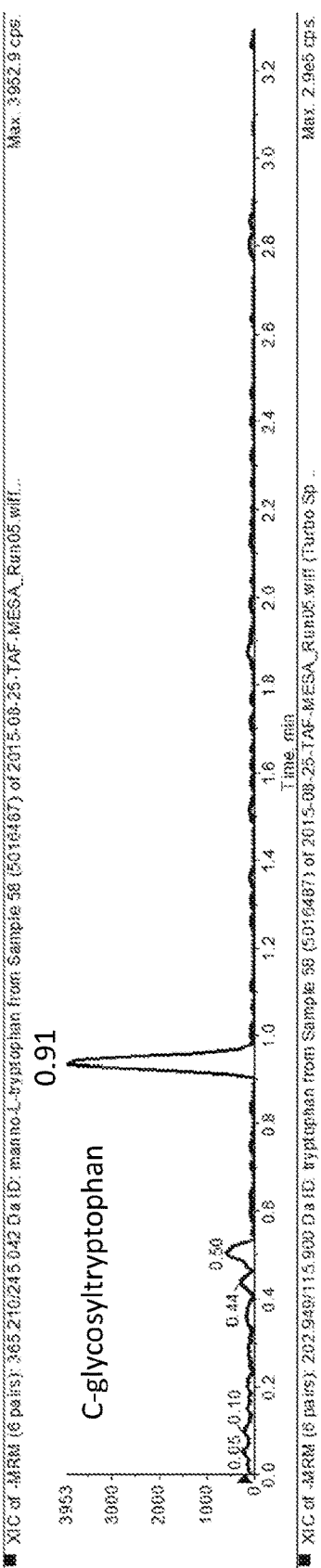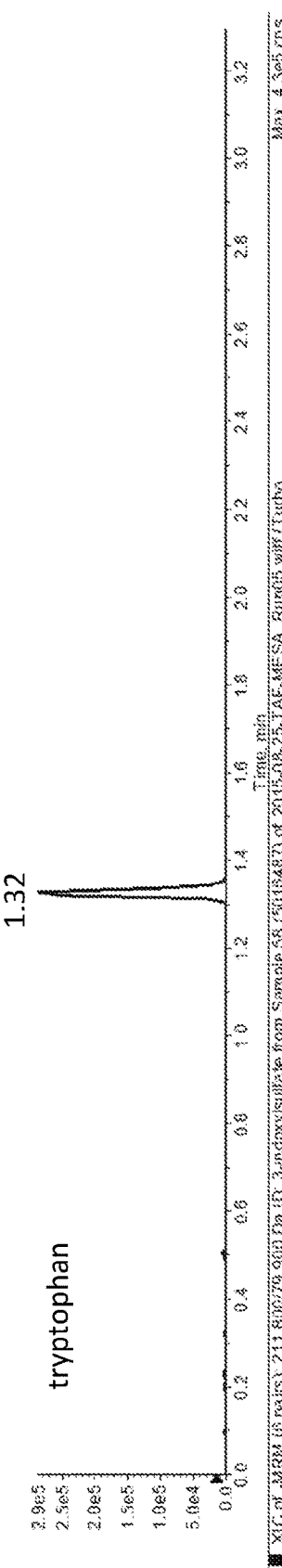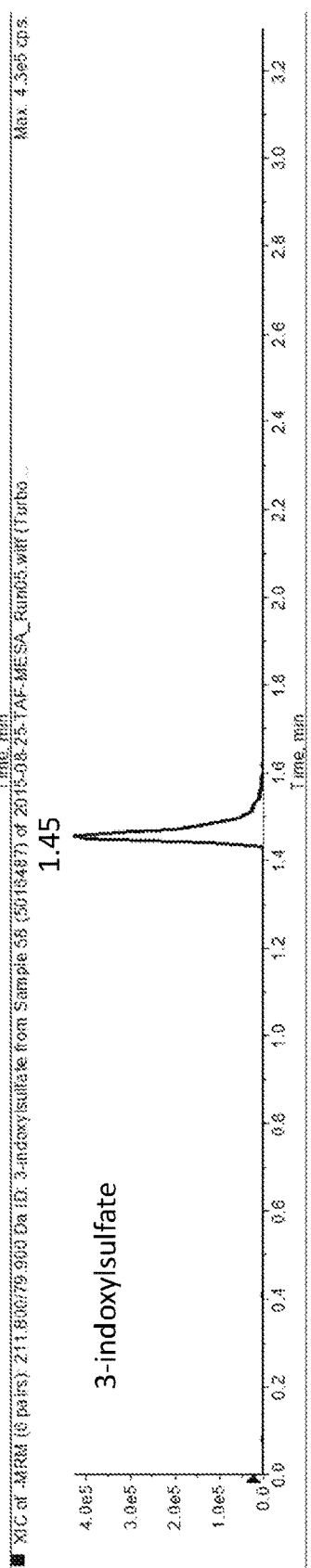
Fig. 4B
Fig. 4C
Fig. 4D

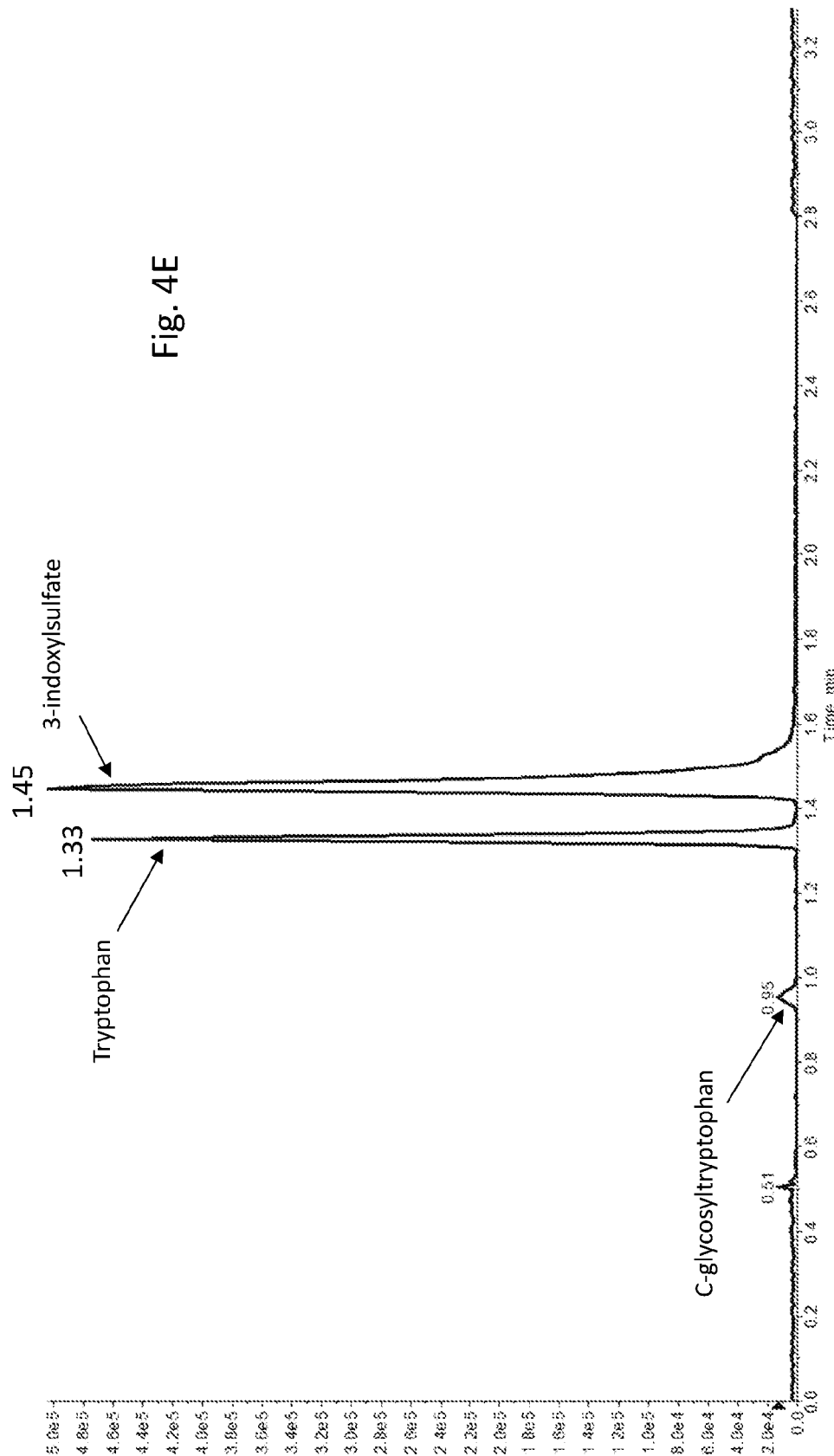

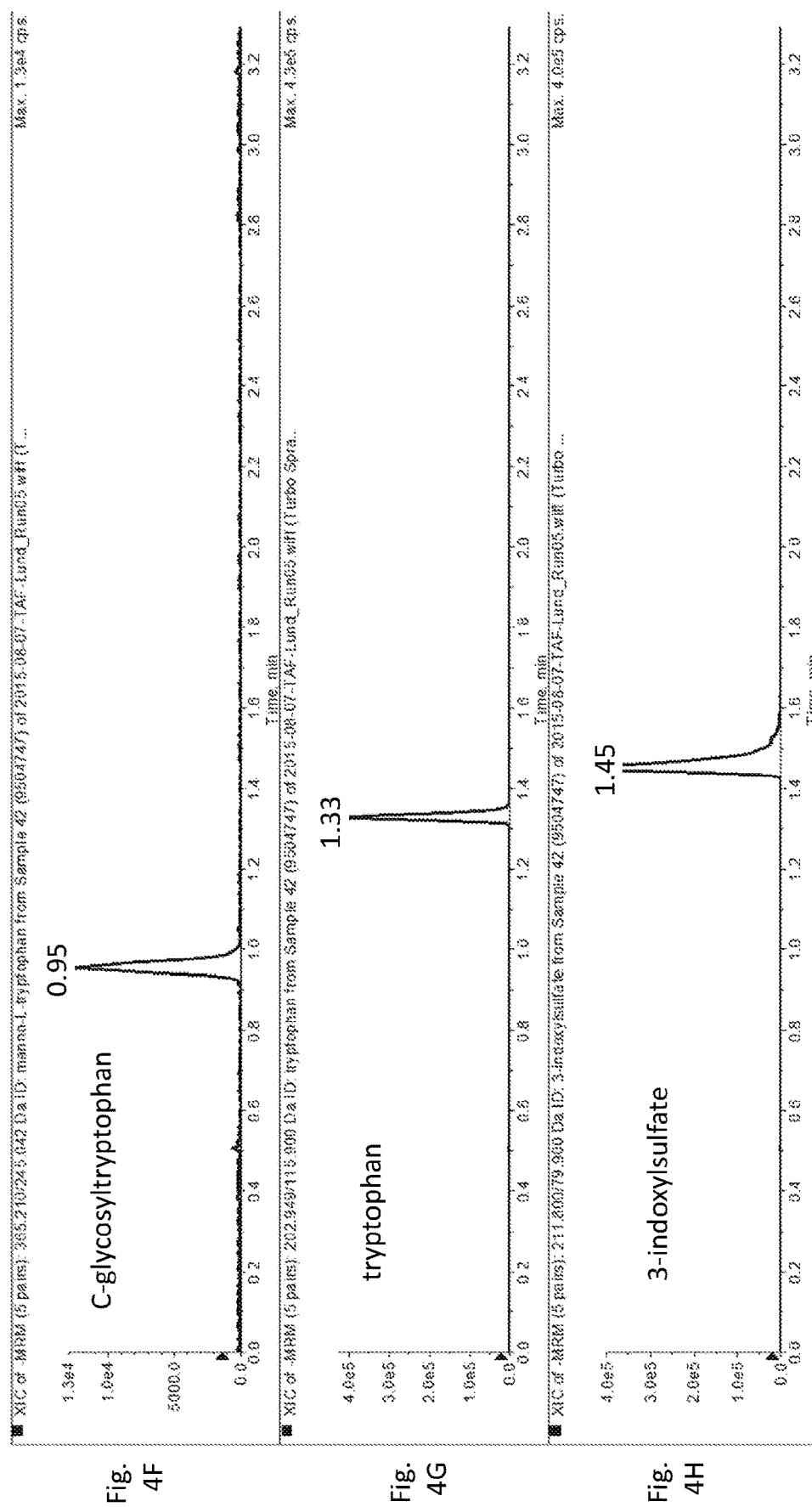

MASS SPECTROMETRY ASSAY METHOD FOR DETECTION AND QUANTITATION OF KIDNEY FUNCTION METABOLITES

CROSS-REFERENCE TO RELATED APPLICATIONS

This application is a U.S. National Stage application of International Application No. PCT/US17/66364, filed on Dec. 14, 2017, which claims the benefit of U.S. Provisional Patent Application No. 62/435,967, filed Dec. 19, 2016, U.S. Provisional Patent Application No. 62/526,043, filed Jun. 28, 2017, and U.S. Provisional Patent Application No. 62/558,014, filed Sep. 13, 2017, the entire contents of each of which are hereby incorporated herein by reference.

BACKGROUND

The following information to describe the background of the invention is provided to assist the understanding of the invention and is not admitted to constitute or describe prior art to the invention.

There is a significant unmet clinical need for a sensitive, accurate and convenient test to assess the excretory function of the kidneys (glomerular filtration rate, GFR). The most accurate measurement of renal function is the measured glomerular filtration rate (mGFR), which requires the use of filtration markers (e.g., inulin, iothalamate, iohexol). Due to its complexity, this measurement is expensive, difficult to perform in routine clinical practice, and is typically only used in research studies or for potential kidney donors. Other current assessments of kidney function (e.g., BUN, urine albumin measurements; glomerular filtration rate estimates (eGFR) based on the levels of serum creatinine, cystatin C) are not sufficiently sensitive and/or accurate to detect compromised kidney function at an early stage of kidney injury or early kidney disease or to monitor disease progression, especially at the earliest stages of chronic kidney disease (CKD) when individuals are asymptomatic. Consequently, alternative measures of kidney function based on the measured levels of combinations of one or more and up to seventeen metabolite biomarkers selected from the group consisting of pseudouridine, N-acetylthreonine, phenylacetylglutamine, tryptophan, N,N,N-Trimethyl-L-Alanyl-L-Proline (TMAP), creatinine, meso-erythritol, arabitol, myo-inositol, N-acetylserine, N-acetylalanine, 3-methylhistidine, trans-4-hydroxyproline, kynurenine, urea, C-glycosyltryptophan (also referred to as 2-mannopyranosyl-tryptophan, 2-(α-D-Mannopyranosyl)-L-tryptophan, Manno-L-tryptophan, or 2-MT), and 3-indoxylsulfate have been developed. Combinations of these analytes are used in complex equations to derive an estimated GFR (eGFR) that is more precise than the eGFR estimates based on the levels of serum creatinine and/or cystatin C. The advantage of this approach is its ease of use in routine clinical practice for more precise assessment of kidney function. The improved precision in assessing kidney function allows appropriate treatment intervention and monitoring of kidney function, which enables better treatment outcomes.

Described herein are methods for the detection and quantitation of up to seventeen analytes in a biological sample. The seventeen analytes may include a panel comprised of one or more analytes selected from pseudouridine, N-acetylthreonine, phenylacetylglutamine, tryptophan, TMAP, creatinine, meso-erythritol, arabitol, myo-inositol, N-acetylserine, N-acetylalanine, 3-methylhistidine, trans-4-hydroxyproline, kynurenine, urea, C-glycosyltryptophan, and 3-indoxylsulfate. Advantageously, the metabolite assays require a small sample size, do not require derivatization and can be performed using mass spectrometry analysis methods.

SUMMARY

In a first aspect of the invention, a method comprises detecting and determining the amount of a panel of analytes comprised of one or more analytes selected from the group consisting of pseudouridine, N-acetylthreonine, phenylacetylglutamine, tryptophan, TMAP, creatinine, meso-erythritol, arabitol, myo-inositol, N-acetylserine, N-acetylalanine, 3-methylhistidine, trans-4-hydroxyproline, kynurenine, urea, C-glycosyltryptophan, 3-indoxylsulfate and combinations thereof in a sample by mass spectrometry. In one embodiment, the method comprises subjecting the sample to an ionization source under conditions suitable to produce one or more ions detectable by mass spectrometry from each of the one or more analytes. In another embodiment, the analytes are not derivatized prior to ionization. Methods to extract the analytes from biological samples and to chromatographically separate the analytes prior to detection by mass spectrometry are also provided.

In another aspect, a method comprises detecting and determining the amount of a panel of analytes comprised of one or more analytes selected from the group consisting of pseudouridine, N-acetylthreonine, phenylacetylglutamine, tryptophan, TMAP, creatinine, meso-erythritol, arabitol, myo-inositol, N-acetylserine, N-acetylalanine, 3-methylhistidine, trans-4-hydroxyproline, kynurenine, urea, C-glycosyltryptophan, 3-indoxylsulfate and combinations thereof in a sample by mass spectrometry wherein, if the one or more assayed analytes is only one analyte, the one analyte is not creatinine.

In an embodiment, the mass spectrometry is tandem mass spectrometry.

In an embodiment wherein the one or more analytes comprises N-acetylthreonine, the one or more ions from N-acetylthreonine may comprise one or more ions selected from the group consisting of ions with a mass to charge ratio (m/z) of about 162.0±0.5, 74.1±0.5, 144.0±0.5, 126.1±0.5, 119.9±0.5, 116.1±0.5, 102.0±0.5, 97.9±0.5, 84.0±0.5, 70.0±0.5, 57.0±0.5, 56.0±0.5, 43.0±0.5, 28.1±0.5, 159.9±0.5, 73.9±0.5, 118.1±0.5, 115.8±0.5, 97.9±0.5, 71.9±0.5, 70.9±0.5, 70.1±0.5, 56.1±0.5, 54.0±0.5, 42.0±0.5, 40.9±0.5, 26.0±0.5, and 159.9±0.5.

In an embodiment wherein the one or more analytes comprises phenylacetylglutamine, the one or more ions from phenylacetylglutamine may comprise one or more ions selected from the group consisting of ions with a mass to charge ratio (m/z) of about 265.0±0.5, 91.0±0.5, 248.1±0.5, 219.1±0.5, 147.1±0.5, 136.0±0.5, 130.0±0.5, 129.1±0.5, 101.1±0.5, 84.0±0.5, 83.0±0.5, 65.0±0.5, 56.0±0.5, 50.9±0.5, 44.0±0.5, 40.9±0.5, 39.1±0.5, 28.0±0.5, 262.9±0.5, and 42.0±0.5.

In an embodiment wherein the one or more analytes comprises creatinine, the one or more ions from creatinine may comprise one or more ions selected from the group consisting of ions with a mass to charge ratio (m/z) of about 113.9±0.5, 43.0±0.5, 86.0±0.5, 72.0±0.5, 44.1±0.5, 42.0±0.5, 28.1±0.5, 111.9±0.5, and 67.9±0.5.

In an embodiment wherein the one or more analytes comprises tryptophan, the one or more ions from tryptophan may comprise one or more ions selected from the group consisting of ions with a mass to charge ratio (m/z) of about 205.0±0.5, 146.0±0.5, 191-193±0.5, 173-174±0.5, 163-

164±0.5, 144.8-151.2±0.5, 117.1-122.1±0.5, 102.9-110.1±0.5, 89.9-96.0±0.5, 74.1-81.1±0.5, 60.9-68.9±0.5, 50.1-54.1±0.5, 38.0-43.1±0.5, 28.0-29.0±0.5, 202.9±0.5, 115.9±0.5, 185.9±0.5, 158.9±0.5, 141.9±0.5, 130.0±0.5, 74.1±0.5, 72.2±0.5, 59.0±0.5, 44.9±0.5.

In an embodiment wherein the one or more analytes comprises pseudouridine, the one or more ions from pseudouridine may comprise one or more ions selected from the group consisting of ions with a mass to charge ratio (m/z) of about 244.9±0.5, 191.0±0.5, 209.0±0.5, 179.0±0.5, 167.0±0.5, 163.0±0.5, 154.8±0.5, 151.0±0.5, 148.0±0.5, 139.0±0.5, 125.0±0.5, 120.0±0.5, 111.8±0.5, 109.8±0.5, 107.8±0.5, 96.0±0.5, 92.0±0.5, 84.0±0.5, 82.0±0.5, 80.0±0.5, 68.0±0.5, 65.2±0.5, 55.0±0.5, 54.0±0.5, 43.0±0.5, 41.0±0.5, 39.0±0.5, 242.9±0.5, 153.0±0.5, 182.8±0.5, 151.9±0.5, 139.9±0.5, 138.9±0.5, 124.0±0.5, 110.8±0.5, 109.9±0.5, 96.0±0.5, 82.0±0.5, 55.0±0.5, 42.0±0.5, and 41.0±0.5.

In an embodiment wherein the one or more analytes comprises meso-erythritol, the one or more ions from meso-erythritol may comprise one or more ions selected from the group consisting of ions with a mass to charge ratio (m/z) of about 120.9±0.5, 88.9±0.5, 120.0±0.5, 119.0±0.5, 105.9±0.5, 103.0±0.5, 100.9±0.5, 93.9±0.5, 92.8±0.5, 79.9±0.5, 77.0±0.5, 70.9±0.5, 67.9±0.5, 65.8±0.5, 65.0±0.5, 58, 9±0.5, 52.0±0.5, 43.210.5, and 40.010.5.

In an embodiment wherein the one or more analytes comprises arabitol, the one or more ions from arabitol may comprise one or more ions selected from the group consisting of ions with a mass to charge ratio (m/z) of about 150.9±0.5, 88.9±0.5, 149.1±0.5, 136.0±0.5, 133.0±0.5, 131.1±0.5, 119.0±0.5, 112.8±0.5, 108.2±0.5, 103.1±0.5, 100.9±0.5, 96.8±0.5, 91.8±0.5, 84.9±0.5, 83.0±0.5, 81.9±0.5, 78.8±0.5, 77.0±0.5, 73.0±0.5, 70.9±0.5, 68.9±0.5, 66.9±0.5, 59.0±0.5, 57.0±0.5, 55.0±0.5, 45.0±0.5, 42.9±0.5, and 41.2±0.5.

In an embodiment wherein the one or more analytes comprise myo-inositol, the one or more ions from myo-inositol may comprise one or more ions selected from the group consisting of ions with a mass to charge ratio (m/z) of about 178.9±0.5, 87.0±0.5, 177.2±0.5, 161.0±0.5, 159.0±0.5, 146.8±0.5, 141.0±0.5, 134.9±0.5, 128.8±0.5, 125.0±0.5, 122.7±0.5, 117.0±0.5, 112.8±0.5, 110.9±0.5, 100.9±0.5, 98.9±0.5, 97.0±0.5, 95.0±0.5, 90.8±0.5, 89.0±0.5, 85.0±0.5, 82.9±0.5, 81.0±0.5, 78.8±0.5, 74.8±0.5, 73.1±0.5, 70.9±0.5, 68.9±0.5, 59.0±0.5, 56.9±0.5, 55.0±0.5, 45.1±0.5, 43.0±0.5, and 41.0±0.5.

In an embodiment wherein the one or more analytes comprise N-acetylserine, the one or more ions from N-acetylserine may comprise one or more ions selected from the group consisting of ions with a mass to charge ratio (m/z) of about 145.9±0.5, 74.0±0.5, 119.0±0.5, 116.0±0.5, 104.9±0.5, 103.9±0.5, 103.0±0.5, 97.9±0.5, 84.0±0.5, 81.0±0.5, 72.0±0.5, 70.0±0.5, 64.9±0.5, 60.8±0.5, 57.0±0.5, 42.0±0.5, and 40.9±0.5.

In an embodiment wherein the one or more analytes comprise N-acetylalanine, the one or more ions from N-acetylalanine may comprise one or more ions selected from the group consisting of ions with a mass to charge ratio (m/z) of about 131.9±0.5, 89.9±0.5, 114.1±0.5, 86.1±0.5, and 44.0±0.5.

In an embodiment wherein the one or more analytes comprise 3-methylhistidine, the one or more ions from 3-methylhistidine may comprise one or more ions selected from the group consisting of ions with a mass to charge ratio (m/z) of about 170.0±0.5, 94.9±0.5, 109.1±0.5, 97.0±0.5, 96.0±0.5, 92.9±0.5, 83.0±0.5, 81.0±0.5, 80.1±0.5, 70.2±0.5, 67.9±0.5, 67.0±0.5, 55.0±0.5, 54.0±0.5, 42.0±0.5, and 41.0±0.5.

In an embodiment wherein the one or more analytes comprise trans-4-hydroxyproline, the one or more ions from trans-4-hydroxyproline may comprise one or more ions selected from the group consisting of ions with a mass to charge ratio (m/z) of about 131.9±0.5, 68.0±0.5, 114.2±0.5, 86.0±0.5, 58.0±0.5, and 41.0±0.5.

In an embodiment wherein the one or more analytes comprise kynurenine, the one or more ions from kynurenine may comprise one or more ions selected from the group consisting of ions with a mass to charge ratio (m/z) of about 209.0±0.5, 94.0±0.5, 192.1±0.5, 191.2±0.5, 174.0±0.5, 164.1±0.5, 163.1±0.5, 150.0±0.5, 146.1±0.5, 136.0±0.5, 119.9±0.5, 118.1±0.5, 98.9±0.5, 88.0±0.5, and 73.9±0.5.

In an embodiment wherein the one or more analytes comprise urea, the one or more ions from urea may comprise one or more ions selected from the group consisting of ions with a mass to charge ratio (m/z) of about 60.9±0.5, 29.2±0.5, 44.0±0.5, 43.0±0.5, 42.1±0.5, 28.0±0.5, and 27.1±0.5.

In an embodiment wherein the one or more analytes comprise 3-indoxylsulfate, the one or more ions from 3-indoxylsulfate may comprise one or more ions selected from the group consisting of ions with a mass to charge ratio (m/z) of about 211.8±0.5, 79.9±0.5, 132.0±0.5, 104.0±0.5, 80.9±0.5, and 77.0±0.5.

In an embodiment wherein the one or more analytes comprise TMAP, the one or more ions from TMAP may comprise one or more ions selected from the group consisting of ions with a mass to charge ratio (m/z) of about 229.1±0.5, 170.1±0.5, 142.2±0.5, 126.0±0.5, 124.0±0.5, 116.0±0.5, 114.0±0.5, 98.0±0.5, 96.0±0.5, 70.0±0.5, 68.0±0.5, 60.0±0.5, 59.1±0.5, 58.1±0.5, 54.9±0.5, 227.0±0.5, 181.0±0.5, 159.0±0.5, 133.2±0.5, 114.8±0.5, 112.9±0.5, 105.8±0.5, 89.1±0.5, 71.0±0.5, 69.0±0.5, and 45.1±0.5.

In an embodiment wherein the one or more analytes comprise C-glycosyltryptophan, the one or more ions from C-glycosyltryptophan may comprise one or more ions selected from the group consisting of ions with a mass to charge ratio (m/z) of about 365.2±0.5, 245.0±0.5, 130.0±0.5, 142.0±0.5, 156.0±0.5, and 116.0±0.5.

In an embodiment, the method includes determining the amount of a plurality of analytes, such as, for example, the amount of two or more analytes selected from the group consisting of tryptophan and 3-indoxylsulfate in a sample by mass spectrometry using a single injection.

In an embodiment, the method includes determining the amount of a plurality of analytes, such as, for example, the amount of two or more or three analytes selected from the group consisting of tryptophan, 3-indoxylsulfate, and C-glycosyltryptophan in a sample by mass spectrometry using a single injection.

In an embodiment, the method includes determining the amount of a plurality of analytes, such as, for example, the amount of two or more, three or more, four or more, or five analytes selected from the group consisting of pseudouridine, N-acetylthreonine, phenylacetylglutamine, tryptophan, and creatinine, in a sample by mass spectrometry using a single injection. In another embodiment, the method includes determining the amount of N-acetylthreonine, pseudouridine, phenylacetylglutamine, and tryptophan.

In an exemplary embodiment, the levels of two or more analytes are determined wherein the two or more analytes comprise pseudouridine and N-acetylthreonine.

In an exemplary embodiment, the levels of two or more analytes are determined wherein the two or more analytes comprise pseudouridine and phenylacetylglutamine.

In an exemplary embodiment, the levels of two or more analytes are determined wherein the two or more analytes comprise pseudouridine and tryptophan.

In an exemplary embodiment, the levels of two or more analytes are determined wherein the two or more analytes comprise pseudouridine and creatinine.

In an exemplary embodiment, the levels of two or more analytes are determined wherein the two or more analytes comprise N-acetylthreonine and phenylacetylglutamine.

In an exemplary embodiment, the levels of two or more analytes are determined wherein the two or more analytes comprise N-acetylthreonine and tryptophan.

In an exemplary embodiment, the levels of two or more analytes are determined wherein the two or more analytes comprise N-acetylthreonine and creatinine.

In an exemplary embodiment, the levels of two or more analytes are determined wherein the two or more analytes comprise phenylacetylglutamine and tryptophan.

In an exemplary embodiment, the levels of two or more analytes are determined wherein the two or more analytes comprise phenylacetylglutamine and creatinine.

In an exemplary embodiment, the levels of two or more analytes are determined wherein the two or more analytes comprise tryptophan and creatinine.

In an exemplary embodiment, the levels of two or more analytes are determined wherein the two or more analytes comprise TMAP and pseudouridine.

In an exemplary embodiment, the levels of two or more analytes are determined wherein the two or more analytes comprise TMAP and N-acetylthreonine.

In an exemplary embodiment, the levels of two or more analytes are determined wherein the two or more analytes comprise TMAP and phenylacetylglutamine.

In an exemplary embodiment, the levels of two or more analytes are determined wherein the two or more analytes comprise TMAP and tryptophan.

In an exemplary embodiment, the levels of two or more analytes are determined wherein the two or more analytes comprise TMAP and creatinine.

In an exemplary embodiment, the levels of two or more analytes are determined wherein the two or more analytes comprise C-glycosyltryptophan and pseudouridine.

In an exemplary embodiment, the levels of two or more analytes are determined wherein the two or more analytes comprise C-glycosyltryptophan and N-acetylthreonine.

In an exemplary embodiment, the levels of two or more analytes are determined wherein the two or more analytes comprise C-glycosyltryptophan and phenylacetylglutamine.

In an exemplary embodiment, the levels of two or more analytes are determined wherein the two or more analytes comprise C-glycosyltryptophan and tryptophan.

In an exemplary embodiment, the levels of two or more analytes are determined wherein the two or more analytes comprise C-glycosyltryptophan and creatinine.

In an exemplary embodiment, the levels of two or more analytes are determined wherein the two or more analytes comprise C-glycosyltryptophan and TMAP.

In an embodiment, the method includes determining the amount of a plurality of analytes, such as, for example, the amount of two or more, three or more, four or more, or five analytes selected from the group consisting of N-acetylthreonine, arabitol, phenylacetylglutamine, creatinine, and pseudouridine, in a sample by mass spectrometry using a single injection.

In an embodiment, the method includes determining the amount of a plurality of analytes, such as, for example, the amount of two or more, three or more, four or more, five or more, or six analytes selected from the group consisting of N-acetylthreonine, pseudouridine, meso-erythritol, arabitol, myo-inositol, and N-acetylserine, in a sample by mass spectrometry using a single injection.

In an embodiment, the method includes determining the amount of a plurality of analytes, such as, for example, the amount of two or more, three or more, four or more, five or more or six analytes selected from the group consisting of N-acetylthreonine, pseudouridine, phenylacetylglutamine, tryptophan, TMAP, and creatinine, in a sample by mass spectrometry using a single injection.

In an embodiment, the method includes determining the amount of a plurality of analytes, such as, for example, the amount of two or more, three or more, four or more, five or more, or six analytes selected from the group consisting of N-acetylthreonine, myo-inositol, tryptophan, phenylacetylglutamine, creatinine, and pseudouridine, in a sample by mass spectrometry using a single injection.

In an embodiment, the method includes determining the amount of a plurality of analytes, such as, for example, the amount of two or more, three or more, four or more, five or more, six or more, seven or more, eight or more, or nine analytes selected from the group consisting of N-acetylthreonine, phenylacetylglutamine, tryptophan, creatinine, N-acetylalanine, 3-methylhistidine, trans-4-hydroxyproline, kynurenine, urea, and combinations thereof in a sample by mass spectrometry using a single injection. Exemplary combinations of analytes are shown in Table A, provided as Appendix A.

In an embodiment, the method includes determining the amount of a plurality of analytes, such as, for example, the amount of two or more, three or more, four or more, five or more, six or more, seven or more, eight or more, nine or more, or ten analytes selected from the group consisting of N-acetylthreonine, meso-erythritol, arabitol, myo-inositol, 3-indoxyl sulfate, tryptophan, phenylacetylglutamine, creatinine, pseudouridine, and N-acetylserine, and combinations thereof in a sample by mass spectrometry using a single injection.

In one embodiment, the run time may be 7 minutes or less. In another embodiment, the run time may be less than 4 minutes.

In embodiments, the sample may be a plasma sample or a serum sample. The sample volume may be 10 µl to 200 µl. For example, the sample volume may be 10 µl, 15, 20, 25, 30, 40, 50 µl, 60, 70, 80, 90, 100, 120, 140, 160, 180 or 200 µl or any other volume between 10 and 200 µl.

BRIEF DESCRIPTION OF THE DRAWINGS

FIGS. 2A-H show example chromatograms of meso-erythritol, N-acetylserine, arabitol, N-acetylthreonine, myo-inositol, and pseudouridine, in a single chromatogram including internal standards from serum (2A) or calibration standards in BSA (2B) and the chromatogram for each analyte individually (2C-H), respectively, generated using Chromatography Method 2.

FIGS. 3A-K show chromatograms of urea, creatinine, trans-4-hydroxyproline, N-acetylalanine, N-acetylthreonine, 3-methylhistidine, tryptophan, kynurenine, and phenylacetylglutamine, in a single chromatogram from serum (3A) or plasma (3B) and the chromatogram for each analyte individually (3C-K), respectively, generated using Chromatography Method 3.

FIGS. 4A-H show chromatograms of C-glycosyltryptophan, tryptophan and 3-indoxylsulfate, in a single chromatogram from serum (4A) or plasma (4E) and the chromatogram for each analyte individually from serum (4B-D) and plasma (4F-H), generated using Chromatography Method 4.

DETAILED DESCRIPTION

Figure 1A:
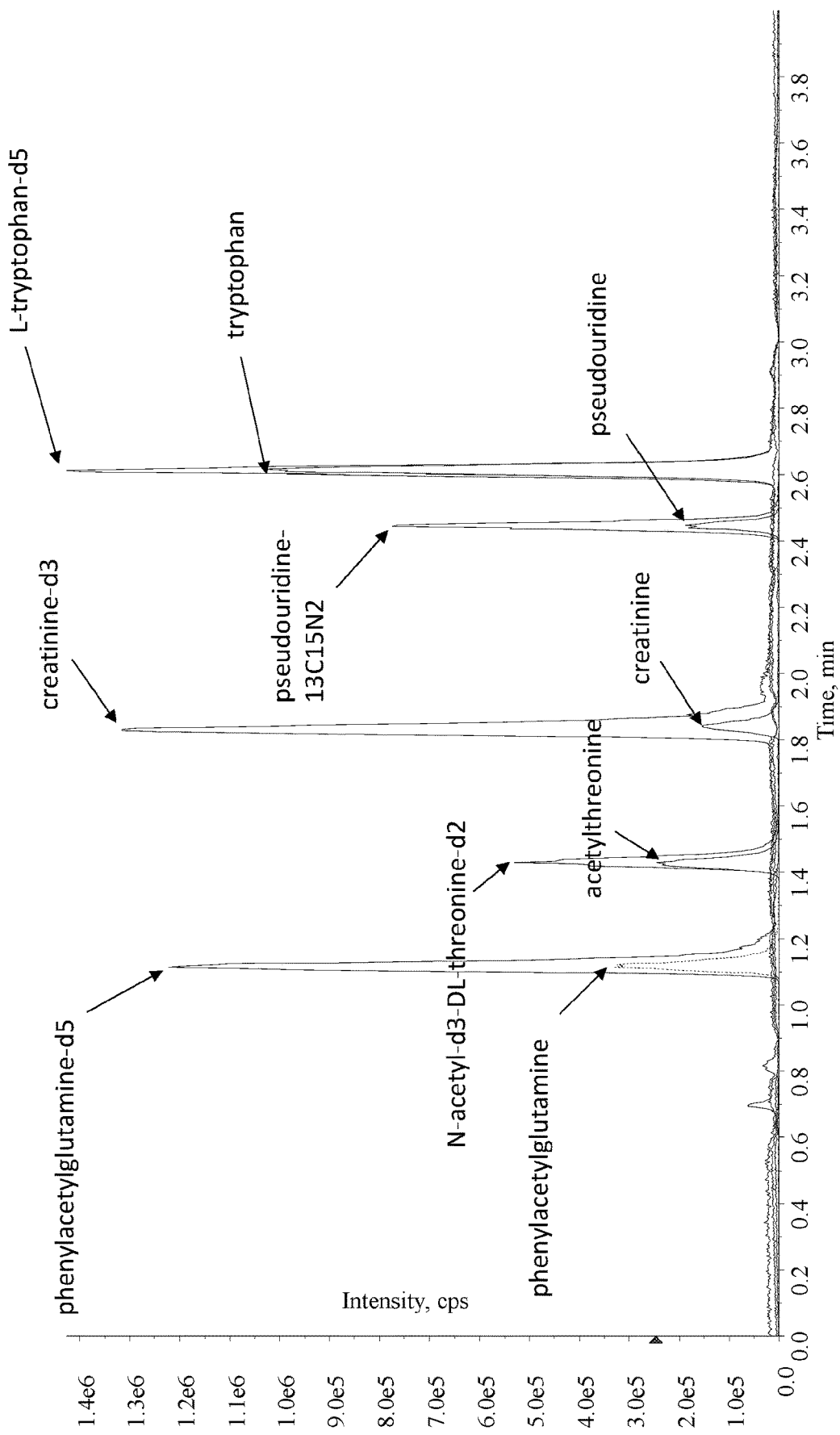
FIGS. 1A-F show example chromatograms of phenylacetylglutamine, pseudouridine, tryptophan, N-acetylthreonine, and creatinine, in a single chromatogram with internal standards (1A) and the chromatogram for each analyte individually (1B-F), respectively, generated using Chromatography Method 1.
Figure 1B:
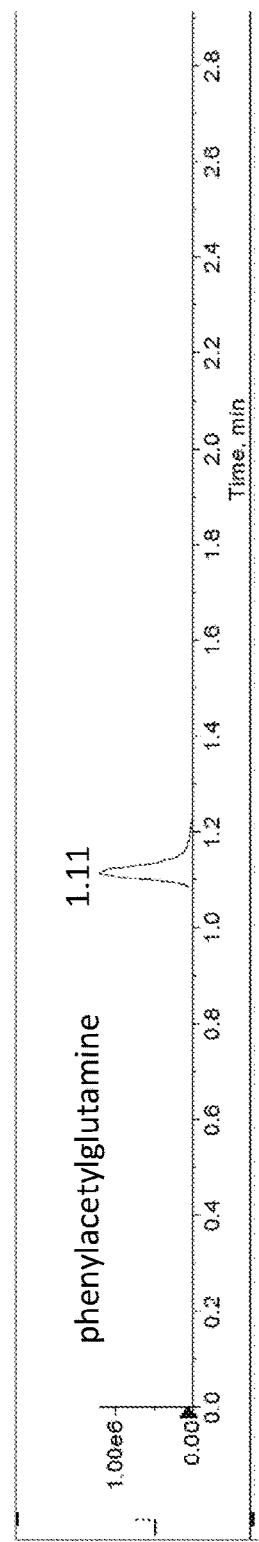
Figure 1C:
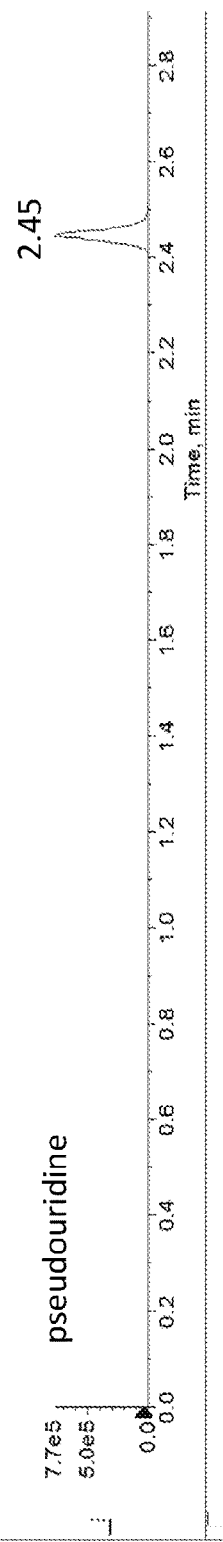
Figure 1D:
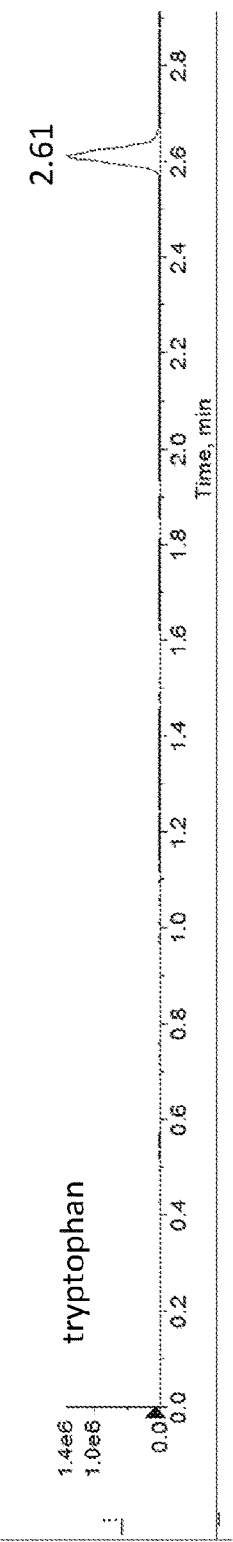
Figure 1E:
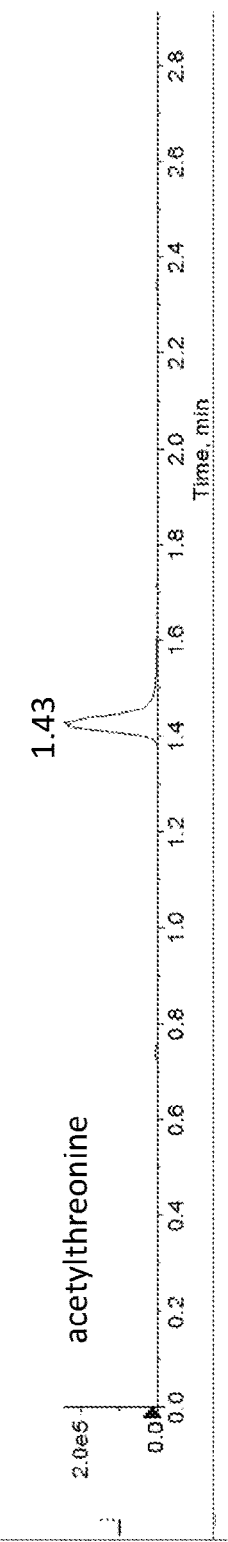
Figure 1F:
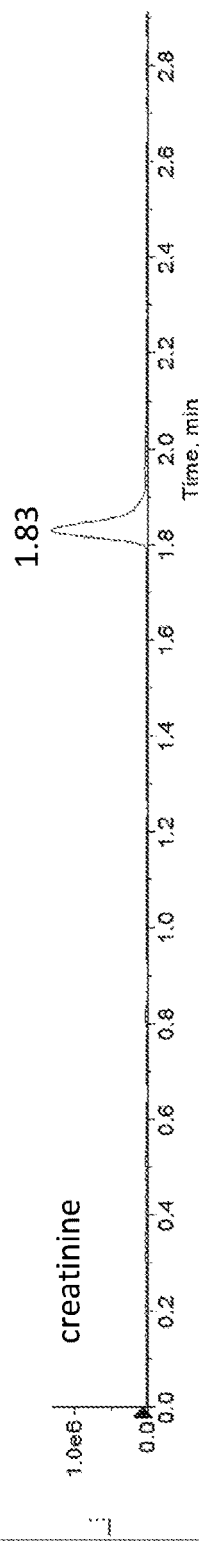
Figure 2A:
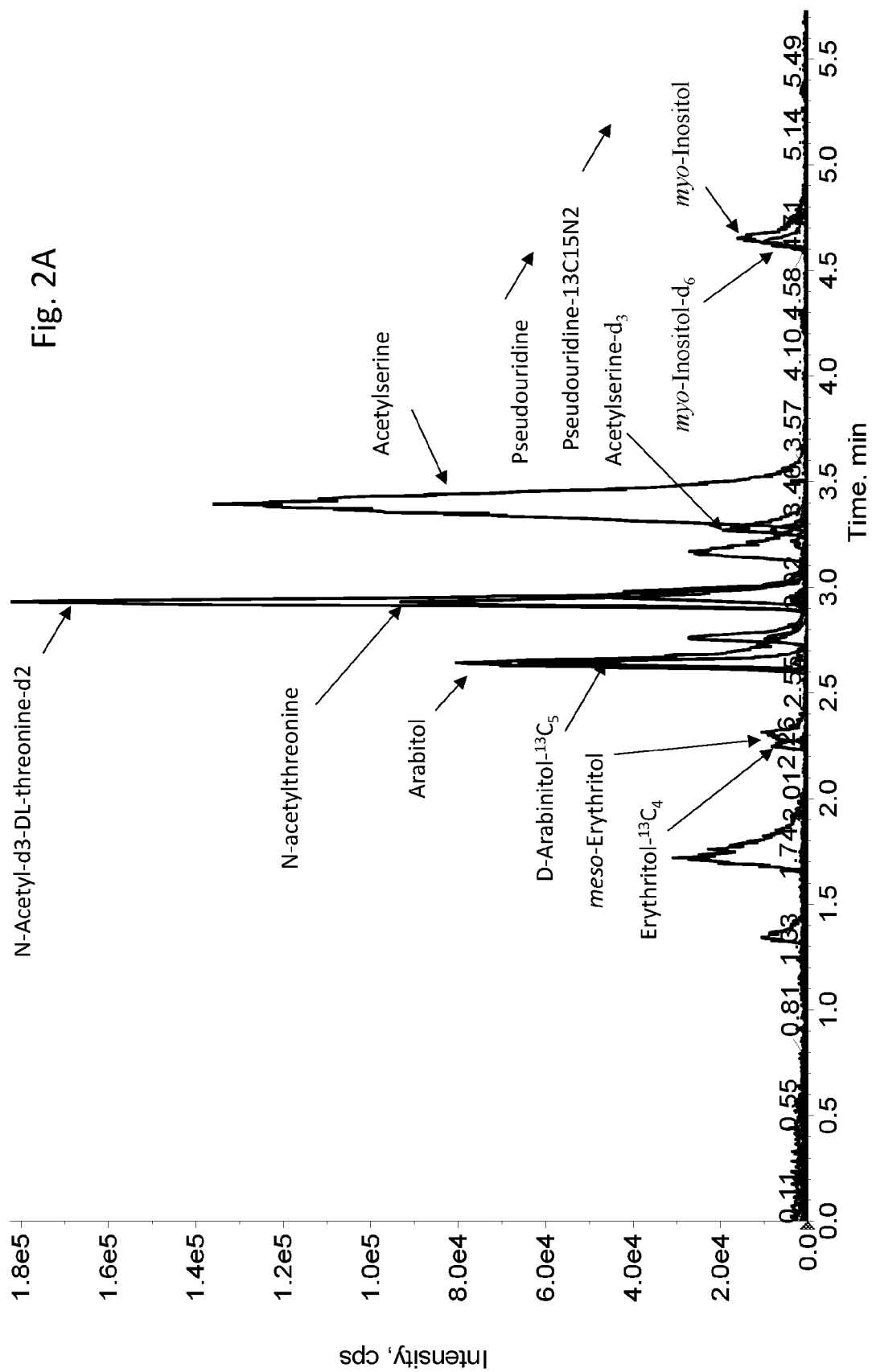
Figure 2B:
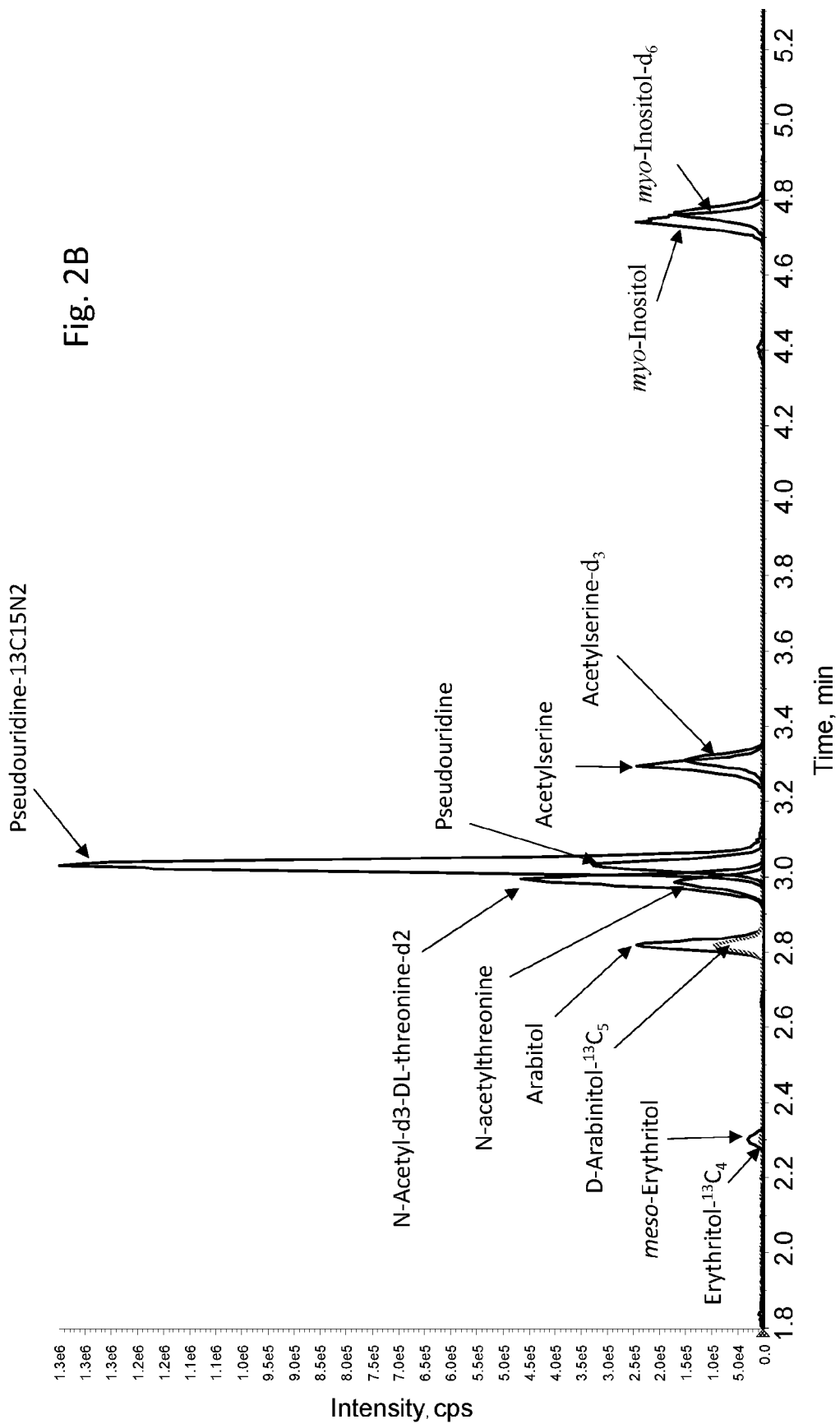
Figure 3A:
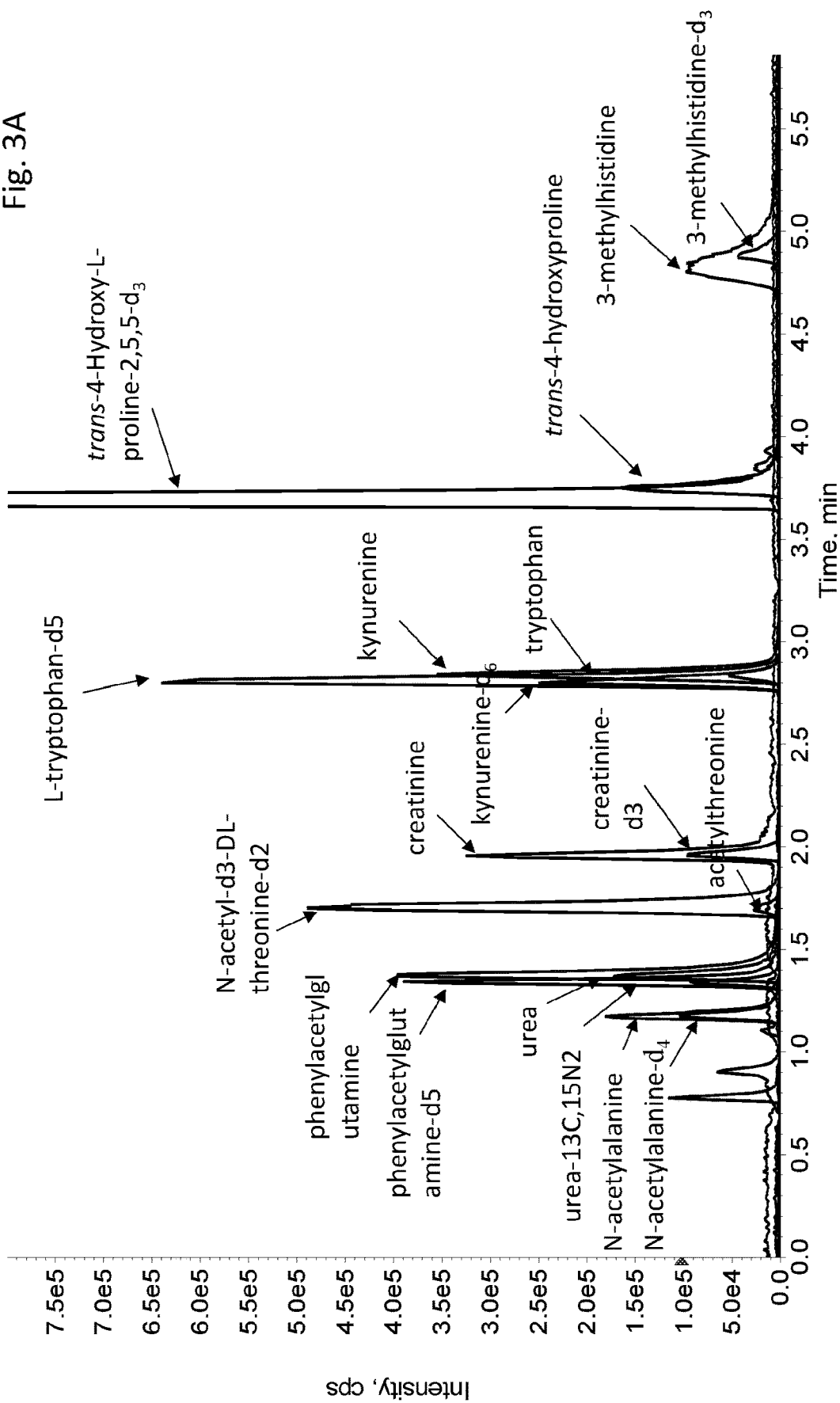
Figure 3B:
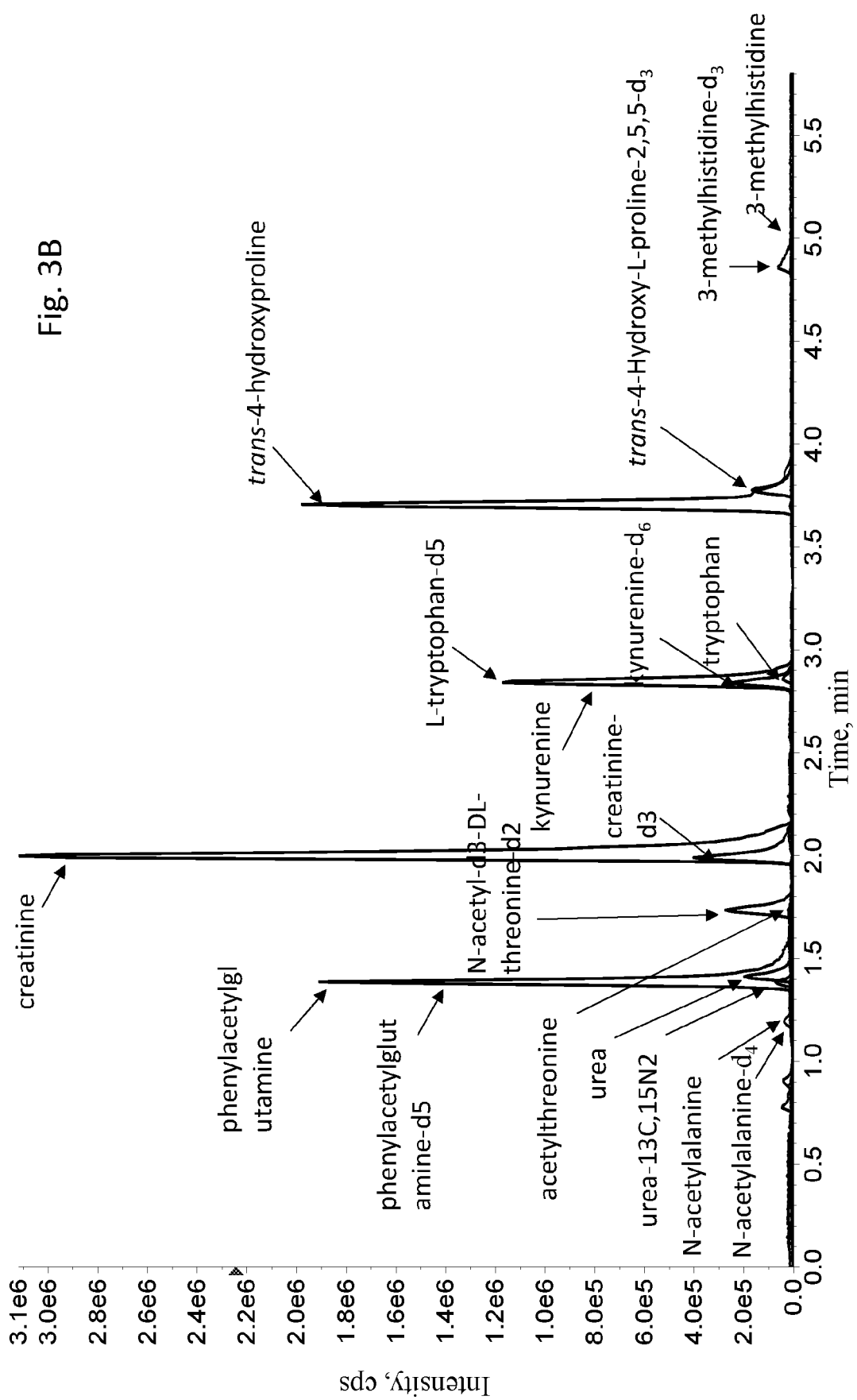
Figures 3H, 3I, 3J, 3K:
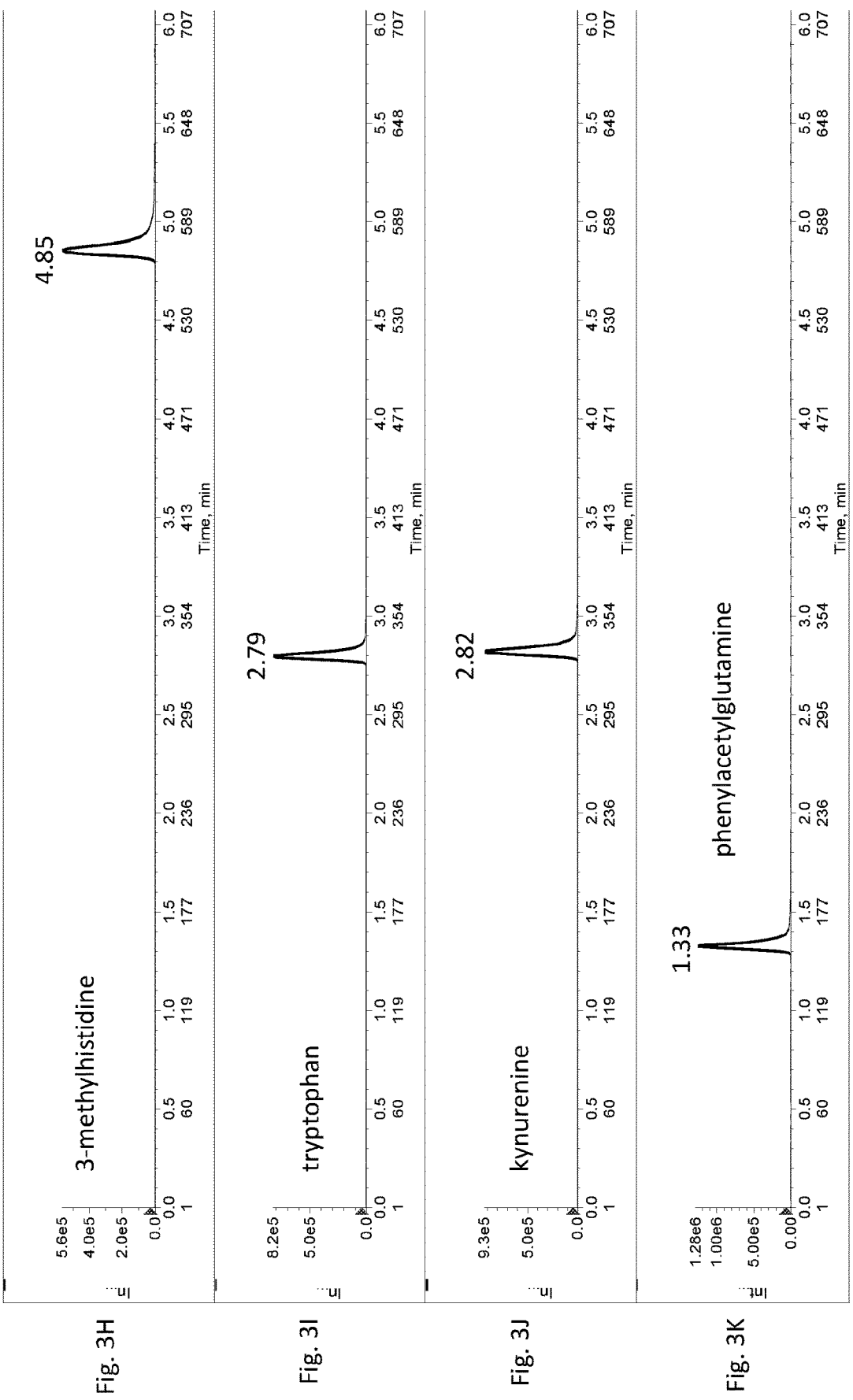

Methods are described for measuring the amount of one or more analytes selected from the group of metabolites consisting of: N-acetylthreonine, pseudouridine, phenylacetylglutamine, tryptophan, TMAP, meso-erythritol, arabitol, myo-inositol, N-acetylserine, N-acetylalanine, 3-methylhistidine, trans-4-hydroxyproline, kynurenine, urea, C-glycosyltryptophan, 3-indoxylsulfate and creatinine in a sample wherein, if the one or more assayed analytes is only one analyte, the one analyte is not creatinine. Mass spectrometric methods are described for quantifying single and multiple analytes in a sample using a single injection method. The methods may use a liquid chromatography step such as UPLC to perform a separation (purification, enrichment) of selected analytes combined with methods of mass spectrometry, thereby providing a high-throughput assay system for quantifying a plurality of analytes in a sample that is amenable to automation.

The methods presented herein provide advantages over current methods to measure these analytes. The ability to measure, in a single injection, a plurality of analytes in various combinations, reduces the time required to obtain analysis results, uses fewer resources in terms of laboratory disposables (e.g., tubes, pipette tips, reagents), laboratory instruments and human resources. These improvements lead to savings by decreasing the costs of the assays and increasing the instrument and laboratory capacity for sample analysis.

Prior to describing this invention in further detail, the following terms are defined.

Definitions:

The term "solid phase extraction" refers to a sample preparation process where components of complex mixture (i.e., mobile phase) are separated according to their physical and chemical properties using solid particle chromatographic packing material (i.e. solid phase or stationary phase). The solid particle packing material may be contained in a cartridge type device (e.g. a column).

The term "separation" refers to the process of separating a complex mixture into its component molecules or metabolites. Common, exemplary laboratory separation techniques include electrophoresis and chromatography.

The term "chromatography" refers to a physical method of separation in which the components (i.e., chemical constituents) to be separated are distributed between two phases, one of which is stationary (stationary phase) while the other (the mobile phase) moves in a definite direction. The mobile phase may be gas ("gas chromatography", "GC") or liquid ("liquid chromatography", "LC"). Chromatographic output data may be used in embodiments of the method described herein.

The term "liquid chromatography" or "LC" refers to a process of selective inhibition of one or more components of a fluid solution as the fluid uniformly moves through a column of a finely divided substance or through capillary passageways. The inhibition results from the distribution of the components of the mixture between one or more stationary phases and the mobile phase(s) as the mobile phase(s) move relative to the stationary phase(s). Examples of "liquid chromatography" include "Reverse phase liquid chromatography" or "RPLC", "high performance liquid chromatography" or "HPLC", "ultra-high performance liquid chromatography" or "UPLC" or "UHPLC".

The term "retention time" refers to the elapsed time in a chromatography process since the introduction of the sample into the separation device. The retention time of a constituent of a sample refers to the elapsed time in a chromatography process between the time of injection of the sample into the separation device and the time that the constituent of the sample elutes (e.g., exits from) the portion of the separation device that contains the stationary phase.

The term "retention index" of a sample component refers to a number, obtained by interpolation (usually logarithmic), relating the retention time or the retention factor of the sample component to the retention times of standards eluted before and after the peak of the sample component, a mechanism that uses the separation characteristics of known standards to remove systematic error.

The term "separation index" refers to a metric associated with chemical constituents separated by a separation technique. For chromatographic separation techniques, the separation index may be retention time or retention index. For non-chromatographic separation techniques, the separation index may be physical distance traveled by the chemical constituent.

As used herein, the terms "separation information" and "separation data" refer to data that indicates the presence or absence of chemical constituents with respect to the separation index. For example, separation data may indicate the presence of a chemical constituent having a particular mass eluting at a particular time. The separation data may indicate that the amount of the chemical constituent eluting over time rises, peaks, and then falls. A graph of the presence of the chemical constituent plotted over the separation index (e.g., time) may display a graphical peak. Thus, within the context of separation data, the terms "peak information" and "peak data" are synonymous with the terms "separation information" and "separation data".

The term "Mass Spectrometry" (MS) refers to a technique for measuring and analyzing molecules that involves ionizing or ionizing and fragmenting a target molecule, then analyzing the ions, based on their mass/charge ratios, to produce a mass spectrum that serves as a "molecular fingerprint". Determining the mass/charge ratio of an object may be done through means of determining the wavelengths at which electromagnetic energy is absorbed by that object. There are several commonly used methods to determine the mass to charge ratio of an ion, some measuring the interaction of the ion trajectory with electromagnetic waves, others measuring the time an ion takes to travel a given distance, or a combination of both. The data from these fragment mass measurements can be searched against databases to obtain identifications of target molecules.

The terms "operating in negative mode" or "operating in negative MRM mode" or "operating in negative ionization mode" refer to those mass spectrometry methods where negative ions are generated and detected. The terms "operating in positive mode" or "operating in positive MRM mode" or "operating in positive ionization mode" refer to those mass spectrometry methods where positive ions are generated and detected.

The term "mass analyzer" refers to a device in a mass spectrometer that separates a mixture of ions by their mass-to-charge ("m/z") ratios.

The term "m/z" refers to the dimensionless quantity formed by dividing the mass number of an ion by its charge number. It has long been called the "mass-to-charge" ratio.

As used herein, the term "source" refers to a device in a mass spectrometer that ionizes a sample to be analyzed. Examples of ion sources include electrospray ionization (ESI), atmospheric pressure chemical ionization (APCI), heated electrospray ionization (HESI), atmospheric pressure photoionization (APPI), flame ionization detector (FID), matrix-assisted laser desorption ionization (MALDI), etc.

As used herein, the term "detector" refers to a device in a mass spectrometer that detects ions.

The term "ion" refers to any object containing a charge, which can be formed for example by adding electrons to or removing electrons from the object.

The term "mass spectrum" refers to a plot of data produced by a mass spectrometer, typically containing m/z values on x-axis and intensity values on y-axis.

The term "scan" refers to a mass spectrum that is associated with a particular separation index. For example, systems that use a chromatographic separation technique may generate multiple scans, each scan at a different retention time.

The term "run time", refers to the time from sample injection to generation of the instrument data. The total run time includes chromatography and mass spectrometry for the sample.

The term "tandem MS" refers to an operation in which a first MS step, called the "primary MS", is performed, followed by performance of one or more of a subsequent MS step, generically referred to as "secondary MS". In the primary MS, an ion, representing one (and possibly more than one) chemical constituent, is detected and recorded during the creation of the primary mass spectrum. The substance represented by the ion is subjected to a secondary MS, in which the substance of interest undergoes fragmentation in order to cause the substance to break into sub-components, which are detected and recorded as a secondary mass spectrum. In a true tandem MS, there is an unambiguous relationship between the ion of interest in the primary MS and the resulting peaks created during the secondary MS. The ion of interest in the primary MS corresponds to a "parent" or precursor ion, while the ions created during the secondary MS correspond to sub-components of the parent ion and are herein referred to as "daughter" or "product" ions.

Thus, tandem MS allows the creation of data structures that represent the parent-daughter relationship of chemical constituents in a complex mixture. This relationship may be represented by a tree-like structure illustrating the relationship of the parent and daughter ions to each other, where the daughter ions represent sub-components of the parent ion. Tandem MS may be repeated on daughter ions to determine "grand-daughter" ions, for example. Thus, tandem MS is not limited to two-levels of fragmentation, but is used generically to refer to multi-level MS, also referred to as "MS$^n$". The term "MS/MS" is a synonym for "MS$^2$". For simplicity, the term "daughter ion" hereinafter refers to any ion created by a secondary or higher-order (i.e., not the primary) MS.

The "level" of one or more biomarkers means the absolute or relative amount or concentration of the biomarker measured in the sample.

"Sample" or "biological sample" means biological material isolated from a subject. The biological sample may contain any biological material suitable for detecting the desired biomarkers, and may comprise cellular and/or non-cellular material from the subject. The sample can be isolated from any suitable biological fluid or tissue such as, for example, blood, blood plasma (plasma), blood serum (serum), urine, cerebral spinal fluid (CSF), or tissue.

"Subject" means any animal, but is preferably a mammal, such as, for example, a human, monkey, mouse, rabbit or rat.

C-glycosyltryptophan is also referred to as 2-mannopyranosyl-tryptophan, 2-(α-D-Mannopyranosyl)-L-tryptophan, Manno-L-tryptophan, 2-MT. Accordingly, these terms are used interchangeably herein.

I. Sample Preparation and Quality Control (QC)

Sample extracts containing analytes are prepared by isolating the analytes away from the macromolecules (e.g., proteins, nucleic acids, lipids) that may be present in the sample. Some or all analytes in a sample may be bound to proteins. Various methods may be used to disrupt the interaction between analyte(s) and protein prior to MS analysis. For example, the analytes may be extracted from a sample to produce a liquid extract, while the proteins that may be present are precipitated and removed. Proteins may be precipitated using, for example, a solution of ethyl acetate or methanol. To precipitate the proteins in the sample, an ethyl acetate or methanol solution is added to the sample, then the mixture may be spun in a centrifuge to separate the liquid supernatant, which contains the extracted analytes, from the precipitated proteins In other embodiments, analytes may be released from protein without precipitating the protein. For example, a formic acid solution may be added to the sample to disrupt the interaction between protein and analyte. Alternatively, ammonium sulfate, a solution of formic acid in ethanol, or a solution of formic acid in methanol may be added to the sample to disrupt ionic interactions between protein and analyte without precipitating the protein. In one example, a solution of acetonitrile, methanol, water, and formic acid may be used to extract analytes from the sample.

In some embodiments the extract may be subjected to various methods including liquid chromatography, electrophoresis, filtration, centrifugation, and affinity separation as described herein to purify or enrich the amount of the selected analyte relative to one or more other components in the sample.

To assess, for example, precision, accuracy, calibration range, or analytical sensitivity of methods of detecting and quantifying analytes, quality control (QC) samples may be used. The concentration of a given analyte(s) to be used in a QC sample may be determined based on lower limit of quantitation (LLOQ) or upper limit of quantitation (ULOQ) of the given analyte(s), as detected in a sample. In one example, the LLOQ may be represented by the concentration of a standard (e.g., Standard A), and the ULOQ may be represented by the concentration of a second standard (e.g., Standard H). The Low QC value may be set at a concentration of about 3×LLOQ, the Mid QC value may be at a concentration of about 25-50% of High QC, and the High QC value may be at a concentration of about 80% of the ULOQ. The QC target concentration levels may be chosen based on a combination of the Analytical Measurement Range (AMR) and the frequency of sample results as measured in a set of representative samples.

II. Chromatography

Prior to mass spectrometry, the analyte extract may be subjected to one or more separation methods such as electrophoresis, filtration, centrifugation, affinity separation, or chromatography. In one embodiment the separation method may comprise liquid chromatography (LC), including, for example, ultra high performance LC (UHPLC).

In some embodiments, UHPLC may be conducted using a reversed phase column chromatographic system, hydrophilic interaction chromatography (HILIC), or a mixed phase column chromatographic system.

The column heater (or column manager) for LC may be set at a temperature of from about 25° C. to about 80° C. For example, the column heater may be set at about 30° C., 40° C., 50° C., 60° C., 70° C., etc.

In an example, UHPLC may be conducted using HILIC system. In another example, UHPLC may be conducted using a reversed phase column chromatographic system. The system may comprise two or more mobile phases. Mobile phases may be referred to as, for example, mobile phase A, mobile phase B, mobile phase A', and mobile phase B'.

In an exemplary embodiment using two mobile phases, A and B, mobile phase A may comprise ammonium formate, formic acid, and water, and mobile phase B may comprise acetonitrile. The concentration of ammonium formate in mobile phase A may range from 0.1 mM to 100 mM and the concentration of formic acid may range from 0.001% to 5%. Further, the concentration of acetonitrile may range from 0% to 100%. In one example, mobile phase A may comprise 20 mM ammonium formate+1% formic acid in water and mobile phase B may comprise 100% acetonitrile. In another example, mobile phase A may comprise 50 mM ammonium formate+1% formic acid in water and mobile phase B may comprise 100% acetonitrile.

In one example, linear gradient elution may be used for chromatography. The starting conditions for linear gradient elution may include the concentration of a mobile phase (e.g., mobile phase A) and/or the flow rate of a mobile phase through the column (e.g., mobile phase A). The starting conditions may be optimized for the separation and/or retention of one or more analytes. The gradient conditions may also be optimized for the separation and/or retention of analytes and may vary depending on the flow rate selected. For example, with initial conditions of 12% mobile phase A and 550 µL/min flow rate, mobile phase A may be increased to 22% at 1.9 min, to 30% at 2.5 min, then to 42% at 2.7 min. Mobile phase B may revert to 12% at 3.4 min where it may be maintained for 0.3 min for equilibration for next sample injection. In another example, initial conditions may be 12% mobile phase A and a 500 µL/min flow rate. Mobile phase A may be increased to 22% at 1.9 min, to 30% at 2.5 min, to 35% at 3.1 min, to 38% at 3.7 min, and to 45% at 5.0 min where it may be maintained for 0.5 min. Mobile phase A may revert to 12% at 5.7 min where it may be maintained for 1.3 min for equilibration before the next sample injection. In another example, initial conditions may be 12% mobile phase A and 550 µL/min flow rate. Mobile phase A may be increased to 22% at 1.9 min, to 30% at 2.5 min, and 42% at 2.7 min. Then, mobile phase A may revert to 12% at 3.4 min where it may be maintained for 0.3 min for equilibration before the next sample injection.

In another example, mobile phase A may comprise ammonium acetate, ammonium hydroxide, and water, and mobile phase B may comprise acetonitrile. The concentration of ammonium acetate may range from about 5 mM to about 200 mM. For example, the concentration of ammonium acetate may be about 50 mM or about 100 mM. The concentration of ammonium hydroxide may range from about 0.001% to about 1%. For example, the concentration of ammonium hydroxide may be about 0.1% or about 0.2%. In a further example, mobile phase A may be 50 mM ammonium acetate+0.1% ammonium hydroxide in water and mobile phase B may be 100% acetonitrile. Linear gradient elution may be used for chromatography and may be carried out with an initial condition of 7% mobile phase A and a flow rate of 450 µL/min. The proportion of mobile phase A may then be increased to 20% at 1.5 min. The proportion of mobile phase A may be increased to 30% at 4.7 min, to 35% at 5.0 min then back to 7% at 5.1 min where it may be maintained for 1.9 min for equilibration before the next sample injection. The total run time may be 7 minutes or less. In another example, mobile phase A may be 100 mM ammonium acetate+0.2% ammonium hydroxide in water and mobile phase B may be 100% acetonitrile. Linear gradient elution may be used for chromatography and may be carried out with an initial condition of 7% mobile phase A and a flow rate of 500 µL/min. Mobile phase A may be increased to 20% at 1.5 min, to 30% at 4.7 min, and to 35% at 5.0 min. Then, mobile phase A may revert to 7% at 5.1 min where it may be maintained for 1.9 min for equilibration before the next sample injection. In another example, linear gradient elution may be carried out with an initial condition of 7% mobile phase A and a flow rate of 800 µL/min. Mobile phase A may be increased to 20% at 0.9 min, to 25% at 1.9 min, and to 30% at 2.1 min. Then, mobile phase A may revert to 7% at 2.2 min where it may be maintained for 0.5 min for equilibration before the next sample injection. In yet another example, using an initial condition of 7% mobile phase A and a flow rate of 800 µL/min for linear gradient elution, mobile phase A may be increased to 22% at 0.9 min, to 30% at 2.5 min, and to 35% at 2.7 min. Then, mobile phase A may revert to 7% at 2.8 min where it may be maintained for 0.4 min for equilibration before the next sample injection.

In yet other embodiments, mobile phase A may comprise formic acid and water, and mobile phase B may comprise formic acid and acetonitrile. In an exemplary embodiment, mobile phase A may contain from about 0.001 to about 1.0% formic acid, and mobile phase B may contain formic acid and acetonitrile from 0-100%. In an example, the concentration of mobile phase A may be about 0.1% formic acid in water and the concentration of mobile phase B may be about 0.1% formic acid in acetonitrile. Linear gradient elution may be used for chromatography and may be carried out with initial conditions of 2% mobile phase B and a flow rate was 700 µL/min. Mobile phase B may be increased to 90% at 2.5 min, maintained at 90% for 0.3 min, and may then be decreased to 2% at 2.9 min where it may be maintained for 0.4 min for equilibration before the next sample injection. The total run time may be less than 4 minutes.

III. Mass Spectrometry and Quantitation

One or more analytes may be ionized by any method known to the skilled artisan, including, for example, mass spectrometry. Mass spectrometry is performed using a mass spectrometer that includes an ion source for ionizing the fractionated sample and creating charged molecules for further analysis. Ionization of the sample may be performed by, for example, electrospray ionization (ESI). Other ion sources may include, for example, atmospheric pressure chemical ionization (APCI), heated electrospray ionization (HESI), atmospheric pressure photoionization (APPI), flame ionization detector (FID), or matrix-assisted laser desorption ionization (MALDI). The choice of ionization method may be determined based on a number of considerations. Exemplary considerations include the analyte to be measured, type of sample, type of detector, and the choice of positive or negative mode.

The one or more analytes may be ionized in positive or negative mode to create one or more ions. For example, the analytes N-acetylthreonine, pseudouridine, phenylacetylglutamine, tryptophan, TMAP, creatinine, N-acetylalanine, 3-methylhistidine, trans-4-hydroxyproline, kynurenine, and urea may be ionized in positive mode. In yet another example, the analytes N-acetylthreonine, TMAP, pseudouridine, meso-erythritol, arabitol, myo-inositol, N-acetylserine, tryptophan, C-glycosyltryptophan, and 3-indoxyl sulfate may be ionized in negative mode. In yet another example, the analytes N-acetylthreonine, meso-erythritol, arabitol, myo-inositol, 3-indoxyl sulfate, tryptophan, phenylacetylglutamine, creatinine, pseudouridine, and N-acetylserine may be ionized in negative mode. In some examples, analytes may be ionized in positive mode and negative mode in a single injection.

Mass spectrometer instrument settings may be optimized for the given method and/or for the particular mass spectrometer used. The instrument may use various gases, for example, nitrogen, helium, argon, or zero air. Mass spectrometry may be performed using AB Sciex QTrap 5500 mass spectrometers. In one example, the mass spectrometer may be operated in positive multiple reaction monitoring (MRM) mode. The ionspray voltage setting may range from about 0.5 kV to about 5.0 kV; in one embodiment the voltage may be set at 4.0 kV. The source temperature may range from about 350° C. to about 600° C.; in one embodiment the source temperature may be set at 550° C. The curtain gas may range from about 10 to about 55 psi; in one embodiment the curtain gas is set at 20 psi. The nebulizer and desolvation gas flow rates may range from about 0 to about 90 psi. In one embodiment the flow rates may be set at 75. The CAD gas setting may range from high to low; in one embodiment the collisionally activated dissociation (CAD) gas is set at medium. Declustering potential may range from less than 15V to more than 170V. The collision energy (CE) may range from less than 12 eV to more than 100 eV. The entrance potential (EP) setting may range from less than about 10V to more than 10V. The collision cell exit potential (CXP) setting may range from less than 8V to more than 14V.

In another example, the instrument may be operated in negative MRM mode. Ionspray voltage settings may range from −0.5 kV to −5.5 kV; in one embodiment the voltage may be set at −4.0 kV. In one embodiment, the voltage may be set at −4.5 kV. The source temperature may range from about 350° C. to 600° C.; in one embodiment the source temperature may be set at 550° C. The curtain gas may range from 10 to 30 or another appropriate value; in one embodiment the curtain gas may be set at 20. The nebulizer and desolvation gas flow rates may range from 40 to 80 or another appropriate value. In one embodiment the flow rates may be set at 70; in another embodiment, the flow rates may be set at 50. In another example the nebulizer gas flow rate may be set at 60 and the desolvation gas flow rate may be set at 65. The CAD gas may range from low to high. In one example the CAD may be set, for example, at medium. In another example, the CAD may be set at high.

After a sample has been ionized, the positively or negatively charged ions may be analyzed to determine a mass-to-charge ratio. Exemplary suitable analyzers for determining mass-to-charge ratios include quadrupole analyzers, ion trap analyzers, and time of flight analyzers. The ions may be detected using, for example, a selective mode or a scanning mode. Exemplary scanning modes include MRM and selected reaction monitoring (SRM).

Analysis results may include data produced by tandem MS. In exemplary embodiments, tandem MS may be accurate-mass tandem MS. For example, the accurate-mass tandem mass spectrometry may use a quadrupole time-of-flight (Q-TOF) analyzer. Tandem MS allows the creation of data structures that represent the parent-daughter relationship of chemical constituents in a complex mixture. This relationship may be represented by a tree-like structure illustrating the relationship of the parent and daughter ions to each other, where the daughter ions represent sub-components of the parent ion.

For example, a primary mass spectrum may contain five distinct ions, which may be represented as five graphical peaks. Each ion in the primary MS may be a parent ion. Each parent ion may be subjected to a secondary MS that produces a mass spectrum showing the daughter ions for that particular parent ion.

The parent/daughter relationship may be extended to describe the relationship between separated components (e.g., components eluting from the chromatography state) and ions detected in the primary MS, and to the relationship between the sample to be analyzed and the separated components.

The mass spectrometer typically provides the user with an ion scan (i.e., a relative abundance of each ion with a particular mass/charge over a given range). Mass spectrometry data may be related to the amount of the analyte in the original sample by a number of methods. In one example, a calibration standard is used to generate a standard curve (calibration curve) so that the relative abundance of a given ion may be converted into an absolute amount of the original analyte. In another example, the calibration standard may be an external standard and a standard curve may be generated based on ions generated from those standards to calculate the quantity of one more analytes. In a further example, the external standard may be an unlabeled analyte.

Internal standards may be added to calibration standards and/or test samples. An internal standard may be used to account for loss of analytes during sample processing in order to get a more accurate value of a measured analyte in the sample. The ratio of analyte peak area to internal standard peak area in the levels of the calibration standards may be used to generate a calibration curve and quantitate samples. One or more isotopically labeled analogs of analytes, for example, N-acetyl-$d_3$-DL-threonine-$d_2$, phenylacetylglutamine-$d_5$, creatinine-$d_3$, L-tryptophan-$d_5$, pseudouridine-$^{13}$C, $^{15}$N$_2$, Erythritol-$^{13}$C$_4$, D-Arabinitol-$^{13}$C$_5$, myo-Inositol-$d_6$, Acetylserine-$d_3$, N-N-Acetyl-L-alanine-$d_4$, 3-Methyl-L-histidine-$d_3$, trans-4-Hydroxy-L-proline-$d_3$, Kynurenine-$d_6$, Urea-$^{13}$C, $^{15}$N$_2$, 2-($\alpha$-D-Mannopyranosyl)-L-tryptophan-$d_4$, 3-indoxylsulfate-$d_4$, and N,N,N-Trimethyl-L-Alanyl-L-Proline-$^{13}$C$_3$, may be used as internal standards.

The analysis data may be sent to a computer and processed using computer software. In one example, peak area ratios of analyte to internal standard are fitted against the concentrations of the calibration standards using a statistical regression method for quantitation. In another example, the statistical regression is weighted linear least squares regression. The slope and intercept calculated using the calibration curve may be used to calculate the unknown concentrations of analytes in experimental samples.

After obtaining the concentration of the one or more kidney panel analytes, the concentration values are entered into a multivariate algorithm to generate an estimated GFR (Glomerular Filtration Rate) score. For example, the concentrations of two analytes, three analytes, four analytes, five analytes, or six analytes selected from N-acetylthreonine, phenylacetylglutamine, tryptophan, TMAP, pseudouridine, and creatinine may be determined. In one example, clinical parameters (e.g., BUN, SCr, urine albumin measurements), markers of kidney function (e.g., β-2 microglobulin, β-TRACE, 2-mannopyranosyl tryptophan (2-MPT)), and/or patient information (e.g., age, family history of CKD, other risk factors) may be used in combination with the concentration values of analytes obtained using the methods described herein.

IV. Kit

A kit for assaying one or more of the kidney panel analytes selected from the group consisting of N-acetylthreonine, phenylacetylglutamine, tryptophan, TMAP, pseudouridine, creatinine, meso-erythritol, arabitol, myo-inositol, N-acetylserine, N-acetylalanine, 3-methylhistidine, trans-4-hydroxyproline, kynurenine, urea, C-glycosyltryptophan, 3-indoxylsulfate, and combinations thereof, wherein, if the one or more assayed analytes is only one analyte, the one analyte is not creatinine, is described herein. For example, a kit may include packaging material and measured amounts of one or more analyte standards or internal standards in amounts sufficient for one or more assays. In exemplary embodiments, the internal standards may be isotopically labeled, the kit may comprise pre-made mobile phase solutions, and/or the kit may comprise mobile phase reagents and instructions to prepare the mobile phase solutions. Kits may also comprise instructions recorded in tangible form (e.g. on paper such as, for example, an instruction booklet or an electronic medium) for using the reagents to measure the one or more analytes.

EXAMPLES

I. Sample Preparation

A. Reagents and Instruments

Mass spectrometric grade (98%) formic acid and ammonium formate (>98%) were obtained from Sigma-Aldrich; HPLC grade methanol and acetonitrile were obtained from JT Baker; and Hydrochloric acid, 6N (Certified) was obtained from Fisher Scientific. A Multi-Tube Vortexer from VWR Scientific was used for mixing. Centrifugation of plates was carried out in a Sorvall ST 40R centrifuge from Thermo Scientific with a 3617 bucket rotor. Human plasma (lithium heparin) and serum were obtained from Bioreclamation. Bovine serum albumin (fatty acid free) was obtained from GenDepot. Phenylacetyl L-Glutamine, N-Acetyl-L-alanine, Beta-Pseudouridine-13C, 15N2, L-Tryptophan-d5, D-Arabinitol-$^{13}$C$_5$, Erythritol-$^{13}$C$_4$, 2-($\alpha$-D-Mannopyranosyl)-L-tryptophan-$d_4$, and 3-Indoxyl sulfate-$d_4$ potassium salt were obtained from Toronto Research Chemicals; Creatinine Hydrochloride, L-Tryptophan, N-Acetyl-DL-serine, L-Kynurenine, trans-4-hydroxy-L-proline, 3-Methyl-L-histidine, D-(+)-Arabitol, meso-Erythritol, myo-Inositol, 3-Indoxyl sulfate potassium salt, and urea were obtained from Sigma-Aldrich; Beta-pseudouridine was obtained from MP Biomedicals; Acetyl-L-threonine was obtained from Santa Cruz Biotechnology; and Nα-(Phenyl-d5-acetyl)-L-glutamine, Creatinine-d3, N-Acetyl-d3-L-threonine-2,3-d2, N-Acetyl-L-alanine-2,3,3,3-$d_4$, N-Acetyl-L-serine-2,3,3-$d_3$, trans-4-Hydroxy-L-proline-2,5,5-$d_3$, N$^7$-Methyl-$d_3$-L-histidine, myo-Inositol-1,2,3,4,5,6-$d_6$ were obtained from CDN Isotopes; L-Kynurenine sulfate (Ring-$d_4$, 3,3-$d_2$) and Urea ($^{13}$C, $^{15}$N$_2$) were obtained from Cambridge Isotope Laboratories. N,N,N-Trimethyl-L-Alanyl-L-Proline-$^{13}$C$_3$ ($^{13}$C$_3$-L,L-TMAP) was obtained from Albany Molecular Research.

B. Sample Preparation

Sample preparation was carried out in a polypropylene 96-well plate. Study samples. QC samples, and calibration standards were thawed on ice and vortexed. To extract the analytes from the study samples and QC samples, 175 µL of a working internal standard (WIS) solution of acetonitrile/methanol/water/formic acid mixture (88/10/2/0.2) containing the appropriate internal standard(s) was added to each well. The WIS solution may be comprised of one or more internal standards and may comprise one or more internal standards for each of the seventeen analytes described herein. The sample blanks were extracted by adding 175 µL of acetonitrile/methanol/water/formic acid mixture (88/10/2/0.2) without internal standards. The WIS concentrations for sixteen analytes are shown in Table 1. All WIS solutions were prepared in a solution of acetonitrile/methanol/water/formic acid (88/10/2/0.2). The determination of WIS concentration may be based on, for example, the concentrations of the analyte in the calibration range. For example, the concentration of the WIS for TMAP may be about the concentration of TMAP calibration standards C and D.

TABLE 1

Working Internal Standard (WIS) Solutions

| Internal Standard Name | Concentration (μg/mL) |
|---|---|
| N-Acetyl-L-alanine-2,3,3,3-$d_4$ | 0.0400 |
| Creatinine-$d_3$ | 0.100 |
| $N^\alpha$-(Phenyl-$d_5$-acetyl)-L-glutamine | 0.0500 |
| N-Acetyl-L-serine-2,3,3-$d_3$ | 0.0400 |
| N-Acetyl-$d_3$-L-threonine-2,3-$d_2$ | 0.300 |
| $N^\tau$-Methyl-$d_3$-L-histidine | 0.0800 |
| L-Tryptophan-$d_5$ | 0.500 |
| L-Kynurenine sulfate (Ring-$d_4$,3,3-$d_2$) | 1.00 |
| trans-4-Hydroxy-L-proline-2,5,5-$d_3$ | 0.200 |
| D-Arabinitol-$^{13}C_5$ | 0.200 |
| Erythritol-$^{13}C_4$ | 0.100 |
| 3-Indoxyl sulfate-$d_4$ potassium salt | 0.200 |
| Urea ($^{13}C$,$^{15}N_2$) | 50.0 |
| myo-Inositol-1,2,3,4,5,6-$d_6$ | 1.00 |
| β-Pseudouridine-$^{13}C$,$^{15}N_2$ | 0.500 |
| 2-(α-D-Mannopyranosyl)-L-tryptophan-$d_4$ | 0.200 |

The calibration range of each analyte was determined. For each analyte, the LLOQ represents the low end of the calibration range, and the high end of the calibration range is represented by the ULOQ. One of ordinary skill in the art would understand how to determine the calibration range for each analyte without undue experimentation. Eight calibrators (standards A-H) were used to cover the calibration ranges. The final analyte concentrations in each calibrator are listed in Table 2. Calibration spiking solutions were prepared at 20-fold of the corresponding calibration concentrations.

TABLE 2

Calibration Ranges for Analytes

| Analyte | Actual Concentration of Calibration Range in Assay (μg/mL) | | | | | | | |
|---|---|---|---|---|---|---|---|---|
|  | A | B | C | D | E | F | G | H |
| N-acetylthreonine | 0.02 | 0.04 | 0.08 | 0.2 | 0.6 | 1 | 1.8 | 2 |
| Phenylacetylglutamine | 0.1 | 0.2 | 0.4 | 1 | 3 | 7.5 | 18 | 20 |
| Creatinine | 2 | 4 | 8 | 20 | 60 | 100 | 180 | 200 |
| Tryptophan | 1 | 2 | 4 | 10 | 30 | 50 | 90 | 100 |
| Pseudouridine | 0.4 | 0.8 | 1.6 | 4 | 12 | 20 | 36 | 40 |
| N-acetylalanine | 0.0075 | 0.015 | 0.03 | 0.06 | 0.24 | 0.6 | 1.5 | 3 |
| Urea | 10 | 20 | 40 | 80 | 320 | 800 | 2,000 | 4,000 |
| Kynurenine | 0.025 | 0.05 | 0.1 | 0.2 | 0.8 | 2 | 5 | 10 |
| 3-Methylhistidine | 0.04 | 0.08 | 0.16 | 0.32 | 1.28 | 3.2 | 8 | 16 |
| trans-4-hydroxyproline | 0.05 | 0.1 | 0.2 | 0.4 | 1.6 | 4 | 10 | 20 |
| N-Acetylserine | 0.015 | 0.03 | 0.06 | 0.12 | 0.48 | 1.2 | 3 | 6 |
| meso-Erythritol | 0.03 | 0.06 | 0.12 | 0.24 | 0.96 | 2.4 | 6 | 12 |
| Arabitol | 0.05 | 0.1 | 0.2 | 0.4 | 1.6 | 4 | 10 | 20 |
| myo-Inositol | 0.1 | 0.2 | 0.4 | 0.8 | 3.2 | 8 | 20 | 40 |
| 3-Indoxyl sulfate | 0.03 | 0.06 | 0.12 | 0.24 | 0.96 | 2.4 | 6 | 12 |
| Manno-L-tryptophan | 0.00500 | 0.0100 | 0.0200 | 0.0400 | 0.160 | 0.400 | 1.00 | 2.00 |

QC levels were determined based on LLOQ and ULOQ. Low, mid, and high level QC samples were prepared from combination of human plasma or serum pools of appropriate analyte concentrations with fortification of analytes as necessary. LLOQ samples were prepared in a fatty-acid free BSA solution (7.5% in PBS) at the same concentrations as standard A in Table 2 for all analytes. QC samples were stored at −80° C.

For study samples, QC samples, calibration standards, and blanks, 25 μL of the extracted sample was transferred to the appropriate wells of the plate. The plate was sealed and mixed on a plate shaker at high speed for approximately 2 minutes. The plate was centrifuged at 4° C. for 10 minutes at 4,000 rpm; and an aliquot of 150 μL of the supernatant was transferred to a new plate for LC-MS/MS analysis. To assess sample recovery, medium QC samples were spiked with a concentration equivalent to calibration standard E as presented in Table 2. The calibration values for standard E are presented in the column headed "E". Stock solutions, calibration spiking solutions, and internal standard solutions were stored at 4° C.

Example 1: Chromatographic Purification and Separation of Analytes from Samples

Chromatographic methods were developed using UHPLC to analyze one or more and up to ten analytes from a single injection. For each chromatographic method a single fixed aliquot of 1.0 μL, of the final extraction solution was injected onto the UPLC column for each sample analyzed. For Chromatography Methods 1, 3, 5, 6, 7 and 8 an Agilent 1290 Infinity UHPLC system equipped with a binary solvent pump unit, a refrigerated autosampler (set at 4° C.), and a column heater (set at 60° C.) was used for liquid chromatography with a HILIC column (Waters ACQUITY UPLC® BEH Amide, 1.7 μm, 2.1×150 mm). A Waters Acquity UPLC system equipped with a binary solvent pump unit, a refrigerated autosampler (set at 4° C.), and a thermostatted column manager (set at 60° C.) was used for liquid chromatography with a HILIC column (Waters ACQUITY UPLC® BEH Amide, 1.7 μm, 2.1×150 mm) for Chromatography Method 2 and with a reversed phase column (Waters ACQUITY UPLC® BEH C18, 1.7 μm, 2.1×100 mm) for Chromatography Method 4. The details of each chromatography method (i.e., mobile phase buffers, elution gradients, flow rates, run time) are exemplified below.

A. Chromatography Method 1 (5 Analytes: N-Acetylthreonine, Phenylacetylglutamine, Pseudouridine, Tryptophan, Creatinine)

In one example, a liquid chromatography method was developed for the purification and separation in the same injection of one or more, two or more, and up to all five analytes selected from the group consisting of N-acetylthreonine, phenylacetylglutamine, pseudouridine, tryptophan, creatinine and combinations thereof, wherein, if the one or more assayed analytes is only one analyte, the one analyte is not creatinine.

Mobile phase A was 20 mM ammonium formate+1% formic acid in water and mobile phase B was 100% acetonitrile. Linear gradient elution, was carried out with an initial condition of 12% mobile phase A (88% mobile phase B) and 550 µL/min flow rate unless otherwise indicated. Mobile phase A was increased from the initial 12% to 22% (78% mobile phase B) at 1.9 min, from 22% to 30% (70% mobile phase B) at 2.5 min, and from 30% to 42% (58% mobile phase B) at 2.7 min. Then, mobile phase A reverted to 12% (88% mobile phase B) at 3.4 min where it was maintained for 0.3 min for equilibration before the next sample was injected. The total run time was 3.70 min.

Chromatography Method 1 separated a plurality of up to five analytes with good peak shapes. Exemplary chromatograms of the resulting separated analytes are shown in FIGS. 1A-F. The approximate retention time for the peak of interest for each analyte is indicated. Approximate retention times (in minutes) were 1.11, 2.45, 2.61, 1.43, and 1.83 for phenylacetylglutamine, pseudouridine, tryptophan, N-acetylthreonine, and creatinine, respectively.

B. Chromatography Method 2 (6 Analytes: Pseudouridine, N-Acetylthreonine, Meso-Erythritol, Arabitol, Myo-Inositol, N-Acetylserine)

In another example, a liquid chromatography method was developed for the purification and separation in the same injection of one or more, two or more, and up to all six analytes selected from the group consisting of pseudouridine, N-acetylthreonine, meso-erythritol, arabitol, myo-inositol, N-acetylserine and combinations thereof.

Mobile phase A was 50 mM ammonium acetate+0.1% ammonium hydroxide in water and mobile phase B was 100% acetonitrile. Linear gradient elution, was carried out with an initial condition of 7% mobile phase A (93% mobile phase B) and 450 µL/min flow rate unless otherwise indicated. Mobile phase A was increased from the initial 7% to 20% (80% mobile phase B) at 1.5 min, from 20% to 30% (70% mobile phase B) at 4.7 min, and from 30% to 35% (65% mobile phase B) at 5.0 min. Then, mobile phase A reverted to 7% (93% mobile phase B) at 5.1 min where it was maintained for 1.9 min for equilibration before the next sample was injected. The total run time was 7.0 min.

Chromatography Method 2 separated a plurality of up to six analytes with good peak shapes. Exemplary chromatograms of the resulting separated analytes are shown in FIGS. 2A-H. Approximate retention times (in minutes) were 2.21, 3.30, 2.72, 2.99, 4.59, and 2.89 for meso-erythritol, N-acetylserine, arabitol, N-acetylthreonine, myo-inositol, and pseudouridine, respectively.

C. Chromatography Method 3 (9 Analytes: N-Acetylthreonine, Phenylacetylglutamine, Tryptophan, Creatinine, N-Acetylalanine, 3-Methylhistidine, Trans-4-Hydroxyproline, Kynurenine, Urea)

In another example, a liquid chromatography method was developed for the purification and separation in the same injection of one or more, two or more, and up to all nine analytes selected from the group consisting of N-acetylthreonine, phenylacetylglutamine, tryptophan, creatinine, N-acetylalanine, 3-methylhistidine, trans-4-hydroxyproline, kynurenine, urea and combinations thereof, wherein, if the one or more assayed analytes is only one analyte, the one analyte is not creatinine.

Mobile phase A was 20 mM ammonium formate+1% formic acid in water and mobile phase B was 100% acetonitrile. Linear gradient elution, was carried out with an initial condition of 12% mobile phase A (88% mobile phase B) and 500 µL/min flow rate unless otherwise indicated. Mobile phase A was increased from the initial 12% to 22% (78% mobile phase B) at 1.9 min, from 22% to 30% (70% mobile phase B) at 2.5 min, from 30% to 35% (65% mobile phase B) at 3.1 min, from 35% to 38% (62% mobile phase B) at 3.7 min, and from 38% to 45% (55% mobile phase B) at 5.0 min where it was maintained for 0.5 min. Then, mobile phase A reverted to 12% (88% mobile phase B) at 5.7 min where it was maintained for 1.3 min for equilibration before the next sample was injected. The total run time was 7.0 min.

Chromatography Method 3 separated a plurality of up to nine analytes with good peak shapes. Exemplary chromatograms of the resulting separated analytes are shown in FIGS. 3A-I. Approximate retention times (in minutes) were 1.36, 1.94, 3.74, 1.17, and 1.69 for urea, creatinine, trans-4-hydroxyproline, N-acetylalanine, N-acetylthreonine, 3-methylhistidine, tryptophan, kynurenine, and phenylacetylglutamine, respectively.

D. Chromatography Method 4 (Tryptophan, 3-Indoxyl Sulfate, C-Glycosyltryptophan)

In another example, a liquid chromatography method was developed for the purification and separation in the same injection of one or more, two or more, and up to all three analytes selected from the group consisting of tryptophan, 3-indoxyl sulfate, and C-glycosyltryptophan, and combinations thereof.

Mobile phase A was 0.1% Formic Acid in water and mobile phase B was 0.1% Formic Acid in Acetonitrile. Linear gradient elution, was carried out with an initial condition of 2% mobile phase B (98% mobile phase A) and a flow rate of 700 µL/min. Mobile phase B was increased from the initial 2% to 90% (10% mobile phase A) at 2.5 min and was maintained at 90% for 0.3 min. Then, mobile phase B reverted to 2% (98% mobile phase A) at 2.9 min where it was maintained for 0.4 min for equilibration before the next sample was injected. The total run time was 3.30 min.

Chromatography Method 4 separated a plurality of up to three analytes with good peak shapes. Exemplary chromatograms of the resulting separated analytes are shown in FIGS. 4A-H. Approximate retention times (in minutes) were 0.91 and 0.95 for C-glycosyltryptophan, 1.32 and 1.33 for tryptophan and 1.45 for 3-indoxylsulfate in serum and plasma, respectively.

E. Chromatography Method 5 (6 Analytes: N-Acetylthreonine, Phenylacetylglutamine, Pseudouridine, Tryptophan, TMAP, Creatinine)

In another example, a liquid chromatography method was developed for the purification and separation in the same injection of one or more, two or more, and up to all six analytes selected from the group consisting of N-acetylthreonine, phenylacetylglutamine, pseudouridine, tryptophan, TMAP, creatinine, and combinations thereof. If the one or more assayed analytes is only one analyte, the one analyte is not creatinine.

Mobile phase A was 20 mM ammonium formate+1% formic acid in water and mobile phase B was 100% acetonitrile. Linear gradient elution, was carried out with an initial condition of 12% mobile phase A (88% mobile phase B) and 550 µL/min flow rate. Mobile phase A was increased from the initial 12% to 22% (78% mobile phase B) at 1.9 min, from 22% to 30% (70% mobile phase B) at 2.5 min, and from 30% to 42% (58% mobile phase B) at 2.7 min. Then, mobile phase A reverted to 12% (88% mobile phase B) at 3.4 min where it was maintained for 0.3 min for equilibration before the next sample was injected. The total run time was 3.70 min.

Figure 5:
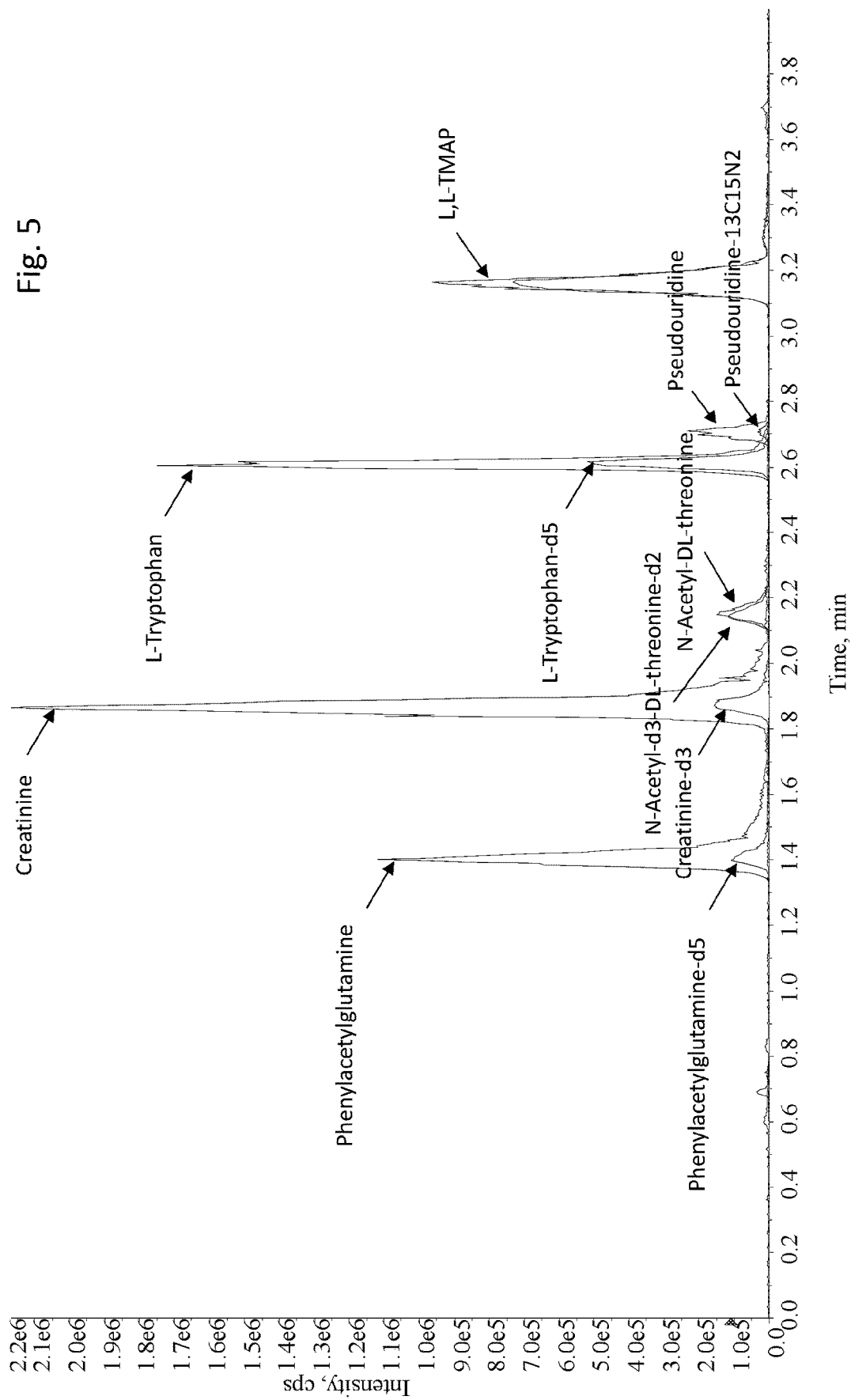
FIG. 5 shows an exemplary chromatogram of phenylacetylglutamine, creatinine, N-acetylthreonine, tryptophan, pseudouridine, and TMAP in a single chromatogram, generated using Chromatography Method 5. Internal standards were included for phenylacetylglutamine, creatinine, N-acetylthreonine, tryptophan, and pseudouridine; TMAP is endogenous.

Chromatography Method 5 separated a plurality of up to six analytes with good peak shapes. Exemplary chromatograms of the resulting separated analytes are shown in FIG. 5. Approximate retention times (in minutes) were 1.40, 1.86, 2.14, 2.61, 2.71, and 3.16 for phenylacetylglutamine, creatinine, N-acetylthreonine, tryptophan, pseudouridine, and TMAP, respectively.

F. Chromatography Method 6 (10: N-Acetylthreonine, Meso-Erythritol, Arabitol, Myo-Inositol, 3-Indoxyl Sulfate, Tryptophan, Phenylacetylglutamine, Creatinine, Pseudouridine, N-Acetylserine)

In another example, a liquid chromatography method was developed for the purification and separation in the same injection of one or more, two or more, and up to all ten analytes selected from the group consisting of N-acetylthreonine, meso-erythritol, arabitol, myo-inositol, 3-indoxyl sulfate, tryptophan, phenylacetylglutamine, creatinine, pseudouridine, and N-acetylserine, and combinations thereof, wherein, if the one or more assayed analytes is only one analyte, the one analyte is not creatinine.

Mobile phase A was 100 mM ammonium acetate+0.2% ammonium hydroxide in water and mobile phase B was 100% acetonitrile. Linear gradient elution, was carried out with an initial condition of 7% mobile phase A (93% mobile phase B) and 500 µL/min flow rate. Mobile phase A was increased from the initial 7% to 20% (80% mobile phase B) at 1.5 min, from 20% to 30% (70% mobile phase B) at 4.7 min, and from 30% to 35% (65% mobile phase B) at 5.0 min. Then, mobile phase A reverted to 7% (93% mobile phase B) at 5.1 min where it was maintained for 1.9 min for equilibration before the next sample was injected. The total run time was 7.0 min.

Figure 6:
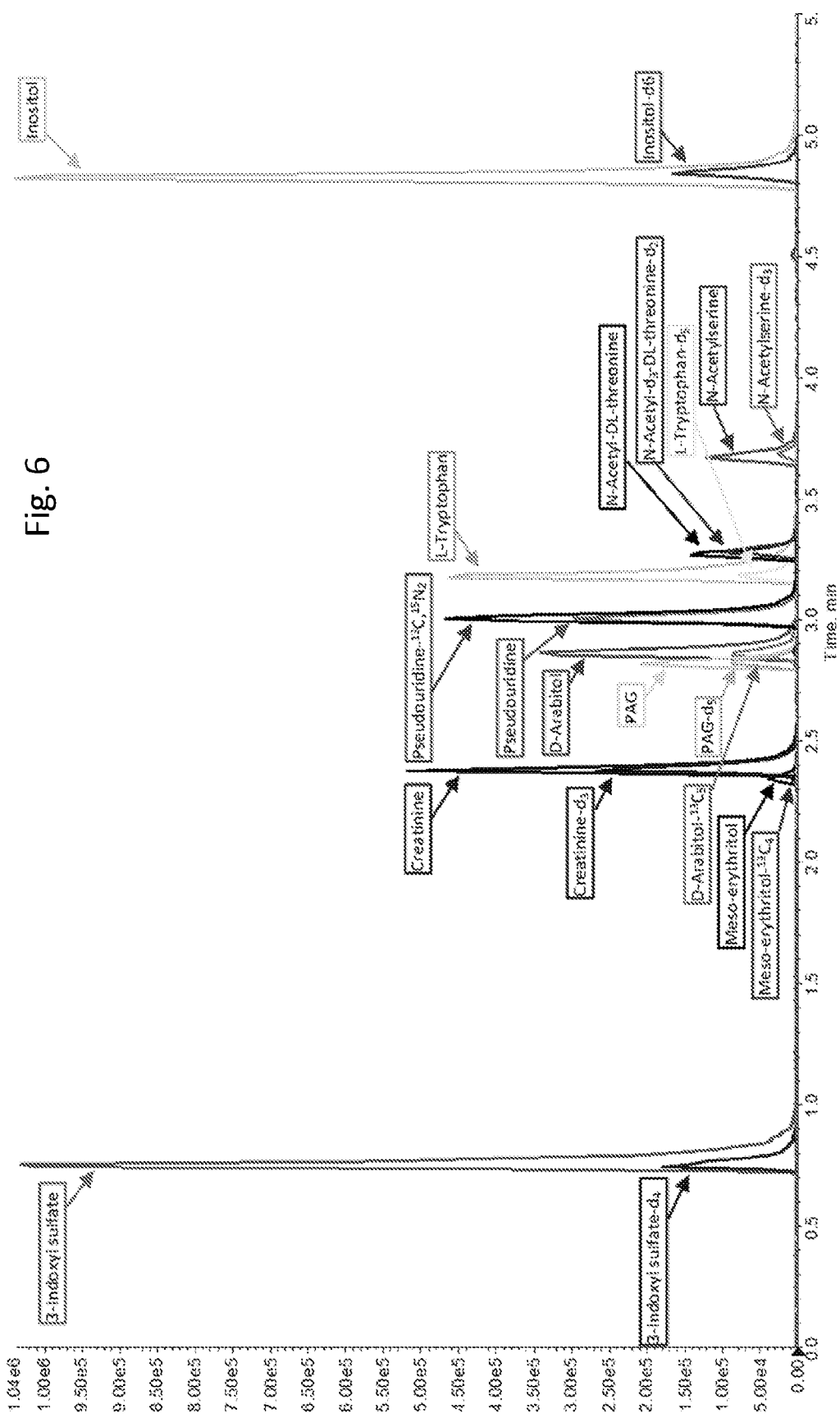
FIG. 6 shows an exemplary chromatogram of N-acetylthreonine, meso-erythritol, arabitol, myo-inositol, 3-indoxyl sulfate, tryptophan, phenylacetylglutamine, creatinine, pseudouridine, and N-acetylserine in a single chromatogram, including internal standards, generated using Chromatography Method 6.

Chromatography Method 6 separated a plurality of up to ten analytes with good peak shapes. An exemplary chromatogram of the resulting separated analytes is shown in FIG. 6. Approximate retention times (in minutes) were 2.35, 2.87, 4.85, 0.78, 3.20, 2.82, 2.40, 3.00, 3.30, and 3.69 for meso-erythritol, arabitol, myo-inositol, 3-indoxyl sulfate, tryptophan, phenylacetylglutamine, creatinine, pseudouridine, N-acetylthreonine, and N-acetylserine, respectively.

G. Chromatography Method 7 (5: Arabitol, Phenylacetylglutamine, Creatinine, Pseudouridine, N-Acetylthreonine)

In another example, a liquid chromatography method was developed for the purification and separation in the same injection of one or more, two or more, and up to all five analytes selected from the group consisting of arabitol, phenylacetylglutamine, creatinine, pseudouridine, N-acetylthreonine, and combinations thereof, wherein, if the one or more assayed analytes is only one analyte, the one analyte is not creatinine.

Mobile phase A was 100 mM ammonium acetate+0.2% ammonium hydroxide in water and mobile phase B was 100% acetonitrile. Linear gradient elution, was carried out with an initial condition of 7% mobile phase A (93% mobile phase B) and 800 µL/min flow rate. Mobile phase A was increased from the initial 7% to 20% (80% mobile phase B) at 0.9 min, from 20% to 25% (75% mobile phase B) at 1.9 min, and from 25% to 30% (70% mobile phase B) at 2.1 min. Then, mobile phase A reverted to 7% (93% mobile phase B) at 2.2 min where it was maintained for 0.5 min for equilibration before the next sample was injected. The total run time was 2.7 min.

Figure 7:
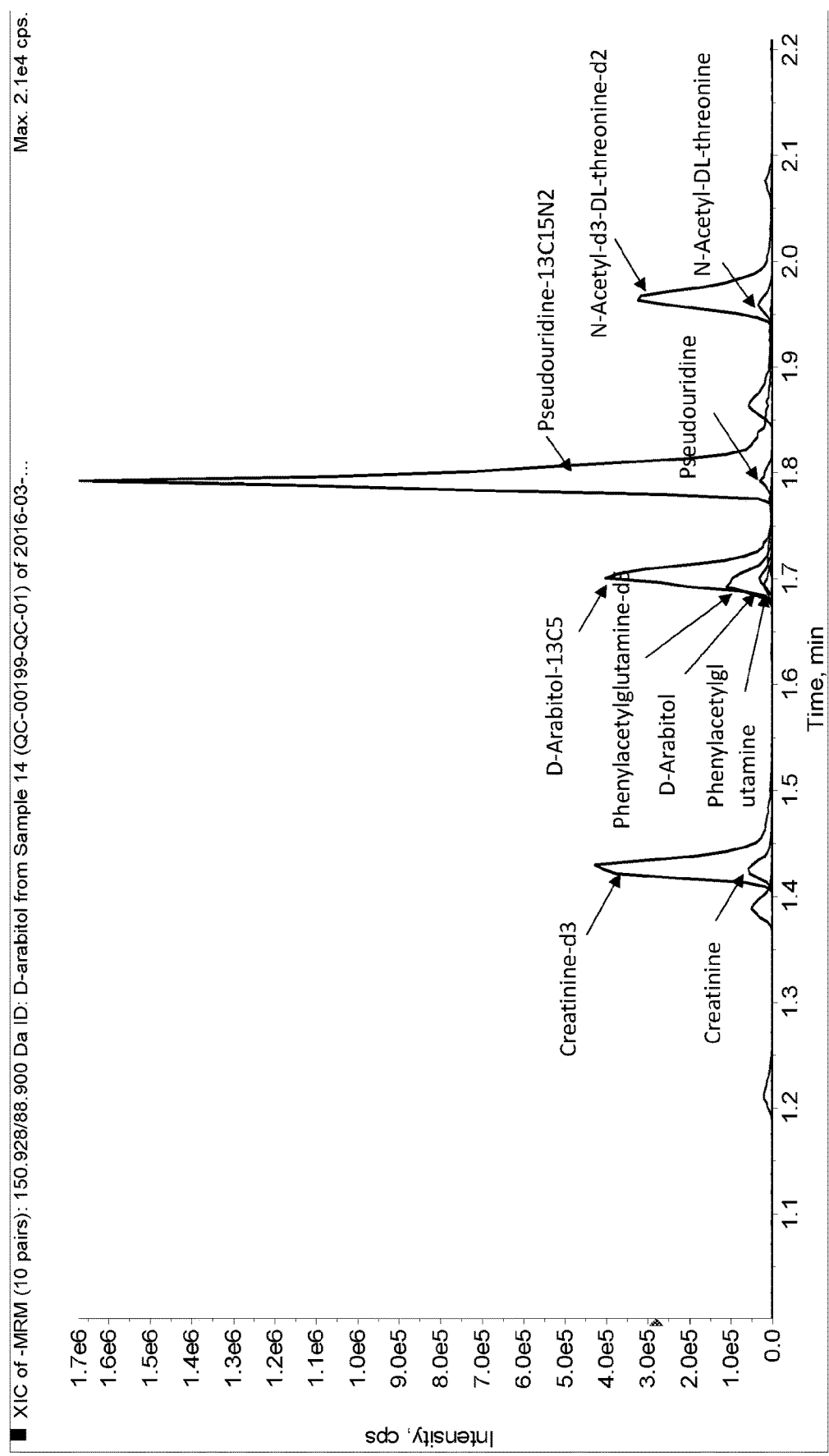
FIG. 7 shows an exemplary chromatogram of arabitol, phenylacetylglutamine, creatinine, pseudouridine, and N-acetylthreonine in a single chromatogram, including internal standards, generated using Chromatography Method 7.

Chromatography Method 7 separated a plurality of up to five analytes with good peak shapes. An exemplary chromatogram of the resulting separated analytes is shown in FIG. 7. Approximate retention times (in minutes) were 1.74, 1.74, 1.48, 1.84, and 1.98 for arabitol, phenylacetylglutamine, creatinine, pseudouridine, and N-acetylthreonine, respectively.

H. Chromatography Method 8 (6: Myo-Inositol, Tryptophan, Phenylacetylglutamine, Creatinine, Pseudouridine, N-Acetylthreonine)

In another example, a liquid chromatography method was developed for the purification and separation in the same injection of one or more, two or more, and up to all six analytes selected from the group consisting of myo-inositol, tryptophan, phenylacetylglutamine, creatinine, pseudouridine, N-acetylthreonine, and combinations thereof, wherein, if the one or more assayed analytes is only one analyte, the one analyte is not creatinine.

Mobile phase A was 100 mM ammonium acetate+0.2% ammonium hydroxide in water and mobile phase B was 100% acetonitrile. Linear gradient elution, was carried out with an initial condition of 7% mobile phase A (93% mobile phase B) and 800 µL/min flow rate. Mobile phase A was increased from the initial 7% to 22% (78% mobile phase B) at 0.9 min, from 22% to 30% (70% mobile phase B) at 2.5 min, and from 30% to 35% (65% mobile phase B) at 2.7 min. Then, mobile phase A reverted to 7% (93% mobile phase B) at 2.8 min where it was maintained for 0.4 min for equilibration before the next sample was injected. The total run time was 3.2 min.

Figure 8:
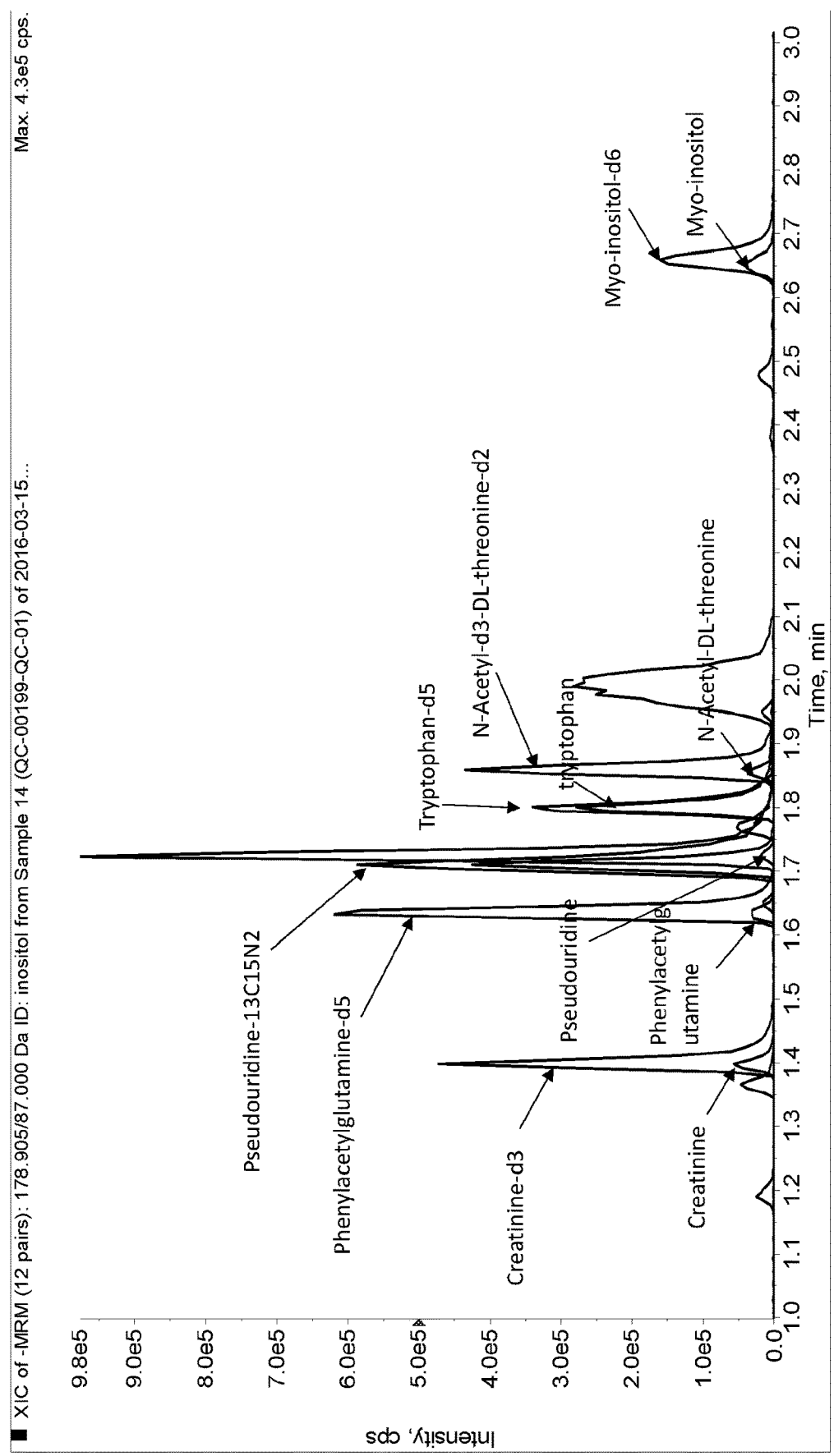
FIG. 8 shows an exemplary chromatogram of myo-inositol, tryptophan, phenylacetylglutamine, creatinine, pseudouridine and N-acetylthreonine in a single chromatogram, including internal standards, generated using Chromatography Method 8.

Chromatography Method 8 separated a plurality of up to six analytes with good peak shapes. An exemplary chromatogram of the resulting separated analytes is shown in FIG. 8. Approximate retention times (in minutes) were 2.64, 1.83, 1.64, 1.40, 1.74, and 1.85 for myo-inositol, tryptophan, phenylacetylglutamine, creatinine, pseudouridine, and N-acetylthreonine, respectively.

Example 2: MS/MS Measurement of Analytes

Mass spectrometry was performed on the sample extracts as described in the methods below using an AB Sciex QTrap 5500 mass spectrometer with Turbo V source (ESI). Raw data were acquired from the instrument and processed using Analyst 1.6.2 software (AB Sciex). For quantitation, peak area ratios of analyte to internal standard were fitted against the concentrations of the calibration standards by weighted ($1/x^2$) linear least squares regression. The resulting slope and intercept of the calibration curve were used to calculate the unknown concentrations in experimental samples.

A. MS/MS Method 1

A method was developed to detect in the same injection the levels of one or more, two or more, and up to all five analytes selected from the group consisting of pseudouridine, N-acetylthreonine, phenylacetylglutamine, tryptophan, creatinine and combinations thereof, wherein, if the one or more assayed analytes is only one analyte, the one analyte is not creatinine. The same MS/MS method was used to detect in the same injection the levels of one or more, two or more, and up to all six analytes selected from the group consisting of pseudouridine, N-acetylthreonine, phenylacetylglutamine, tryptophan, TMAP, creatinine, and combinations thereof.

The eluent from the chromatography column described in Example 1, Chromatography Method 1, was directly and automatically introduced into the electrospray source of a mass spectrometer. In another example, the eluent from the chromatography column described in Example 1, Chromatography Method 5, was directly and automatically introduced into the electrospray source of a mass spectrometer. Acetonitrile: Water (50:50) was used for needle wash. The instrument was operated in positive multiple reaction monitoring (MRM) mode. Ionspray voltage was set at 4.0 kV, source temperature at 550° C., curtain gas (e.g., nitrogen) at 20 psi, and nebulizer and desolvation gas (e.g., nitrogen) flow rates at 75 psi, collisionally activated dissociation (CAD) gas (e.g., nitrogen) at medium.

Raw data were acquired from the instrument and processed using Analyst 1.6.2 software (AB Sciex). For quantitation, peak area ratios of analyte to internal standard were fitted against the concentrations of the calibration standards by weighted ($1/x^2$) linear least squares regression. The resulting slope and intercept of the calibration curve were used to calculate the unknown concentrations in experimental samples. Exemplary ions that were generated for the quantitation of pseudouridine, N-acetylthreonine, phenylacetylglutamine, tryptophan, and creatinine, and TMAP are listed in Table 3. The parent ions are listed under the column headed "Parent ion (m/z)", and the daughter ions used for quantitation in this example are listed in the column labeled "Daughter ion for quantitation (m/z)". The choice of daughter ion for quantitation in this example was optimized for sensitivity across the analytical measurement range; however, additional daughter ions may be selected to replace or augment the daughter ions used for quantitation in the examples.

TABLE 3

Parent and Daughter Ion Mass to Charge Ratios (m/z) of Analytes as measured in positive ionization mode

| Analyte | Parent ion (m/z) | Daughter ion for quantitation (m/z) | Additional daughter ions (m/z) (all ±0.5) |
|---|---|---|---|
| N-acetyl-DL-threonine | 162.0 ± 0.5 | 74.1 ± 0.5 | 144.0, 126.1, 119.9, 116.1, 102.0, 97.9, 84.0, 70.0, 57.0, 56.0, 43.0, 28.1 |
| N-acetyl-d3-DL-threonine-d2 | 167.0 ± 0.5 | 77.1 ± 0.5 | 149.1, 131.9, 129.8, 125.9, 122.8, 121.0, 104.0, 91.0, 86.1, 76.0, 59.0, 58.1, 45.9, 43.0, 31.1, 29.2, 28.0 |
| phenylacetylglutamine | 265.0 ± 0.5 | 91.0 ± 0.5 | 248.1, 219.1, 147.1, 136.0, 130.0, 129.1, 101.1, 84.0, 83.0, 65.0, 56.0, 50.9, 44.0, 40.9, 39.1, 28.0 |
| phenylacetylglutamine-d5 | 270.0 ± 0.5 | 96.3 ± 0.5 | 253.3, 224.3, 147.0, 141.3, 130.0, 100.8, 84.0, 69.0, 68.1, 56.0, 41.1, 28.1 |
| creatinine | 113.9 ± 0.5 | 43.0 ± 0.5 | 86.0, 72.0, 44.1, 42.0, 28.1 |
| creatinine-d3 | 116.9 ± 0.5 | 47.0 ± 0.5 | 89.2, 43.1, 29.1, 28.0 |
| L-tryptophan | 205.0 ± 0.5 | 146.0 ± 0.5 | 188.1, 170.0, 159.1, 144.0, 143.0, 142.0, 140.0, 132.0, 130.1, 128.1, 126.9, 117.9, 116.9, 114.9, 103.0, 91.0, 89.9, 89.0, 77.0, 74.9, 74.0, 64.9, 63.0, 62.0, 61.0, 50.9, 49.9, 39.2, 28.0 |
| L-tryptophan-d5 | 210.0 ± 0.5 | 150.1 ± 0.5 | 191-193, 173-174, 163-164, 144.8-151.2, 117.1-122.1, 102.9-110.1, 89.9-96.0, 74.1-81.1, 60.9-68.9, 50.1-54.1, 38.0-43.1, 28.0-29.0 |
| pseudouridine | 244.9 ± 0.5 | 191.0 ± 0.5 | 209.0, 179.0, 167.0, 163.0, 154.8, 151.0, 148.0, 139.0, 125.0, 120.0, 111.8, 109.8, 107.8, 96.0, 92.0, 84.0, 82.0, 80.0, 68.0, 65.2, 55.0, 54.0, 43.0, 41.0, 39.0 |
| pseudouridine-13C15N2 | 247.9 ± 0.5 | 194.0 ± 0.5 | 230.2, 212.0, 206.9, 194.1, 182.2, 169.9, 166.0, 157.9, 154.0, 148.9, 141.9, 128.1, 120.9, 113.0, 109.1, 96.8, 92.7, 91.0, 85.3, 83.1, 81.2, 78.8, 77.0, 69.1, 65.0, 56.9, 55.0, 53.3, 51.3, 44.9, 43.0, 40.9, 39.0 |

TABLE 3-continued

Parent and Daughter Ion Mass to Charge Ratios (m/z) of Analytes as measured in positive ionization mode

| Analyte | Parent ion (m/z) | Daughter ion for quantitation (m/z) | Additional daughter ions (m/z) (all ±0.5) |
|---|---|---|---|
| TMAP | 229.1 ± 0.5 | 142.2 ± 0.5 or 70.0 ± 0.5 | 170.1, 126.0, 124.0, 116.0, 114.0, 98.0, 96.0, 68.0, 60.0, 59.1, 58.1, 54.9 |
| $^{13}C_3$-L,L-TMAP | 232.2 ± 0.5 | 142.1 ± 0.5 or 70.1 ± 0.5 | 170.1, 126.0, 124.0, 116.0, 114.0, 98.0, 97.1, 96.0, 93.9, 81.0, 80.0, 79.0, 77.0, 74.0, 72.1, 71.1, 69.0, 68.0, 67.1, 63.0, 62.1, 61.1, 60.0, 59.0, 58.1, 57.1, 56.1, 55.0, 54.0, 53.1 |

FIGS. 9-14 show mass spectra resulting from fragmentation of the parent ions indicated in Table 3.

Figure 9:
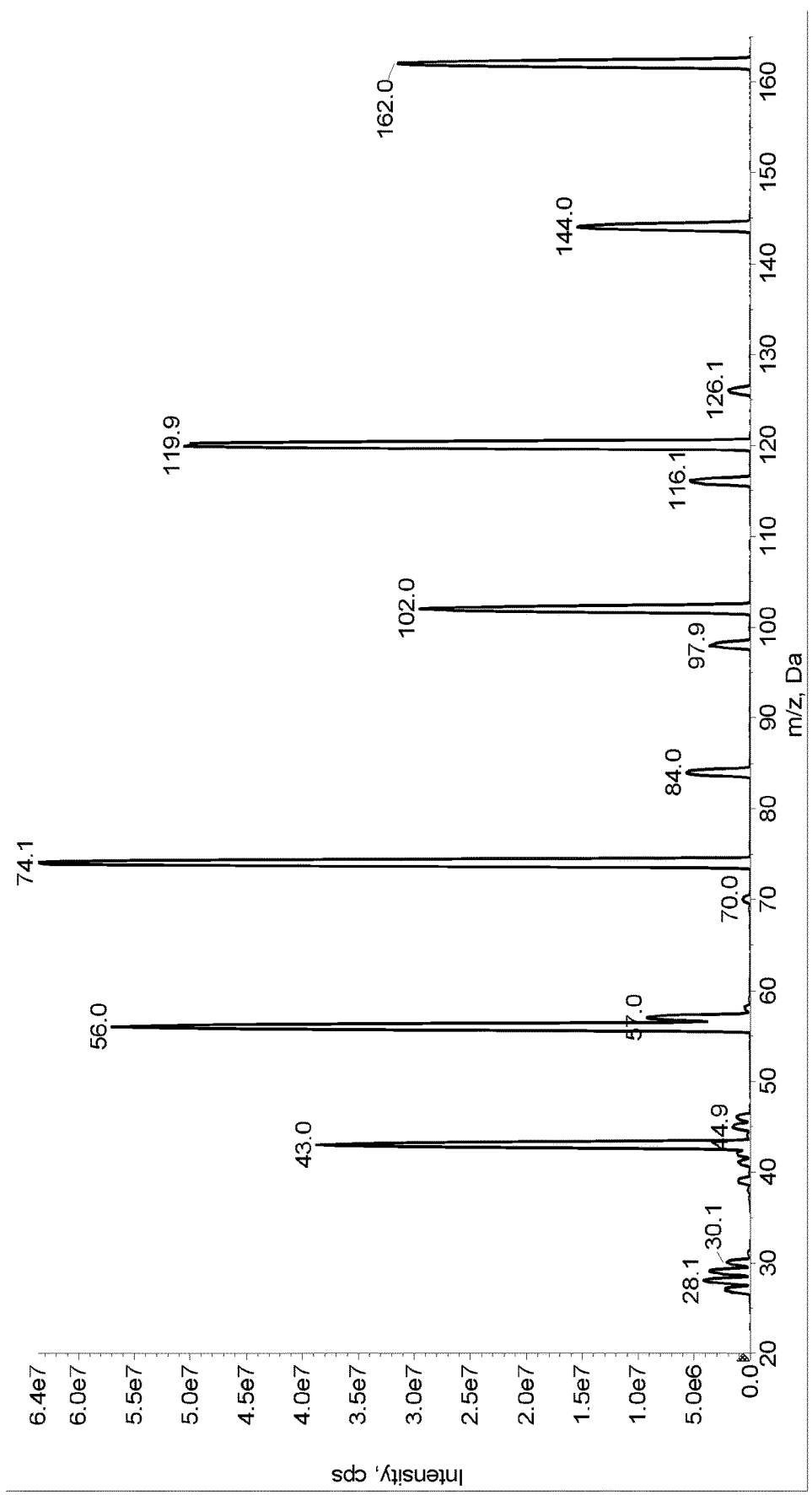
FIG. 9 shows exemplary parent and daughter ion peaks generated from tandem mass spectrometric fragmentation of N-acetylthreonine.

MRM transitions that were generated for the quantitation of N-acetylthreonine in positive ionization mode include those produced by fragmenting a parent ion having a m/z of about 162.0±0.5 to produce daughter ions having m/z of about 74.1±0.5, 144.0±0.5, 126.1±0.5, 119.9±0.5, 116.1±0.5, 102.0±0.5, 97.9±0.5, 84.0±0.5, 70.0±0.5, 57.0±0.5, 56.0±0.5, 43.0±0.5, and 28.1±0.5. These parent and daughter ion peaks generated from tandem mass spectrometric fragmentation of N-acetylthreonine are illustrated in FIG. 9. Any of the daughter ions may be selected for quantitation. In this example, the daughter ion used for quantitation of N-acetylthreonine has a m/z of about 74.1±0.5. The calibration range for N-acetylthreonine was determined to be 0.0200 to 2.00 µg/mL.

Figure 10:
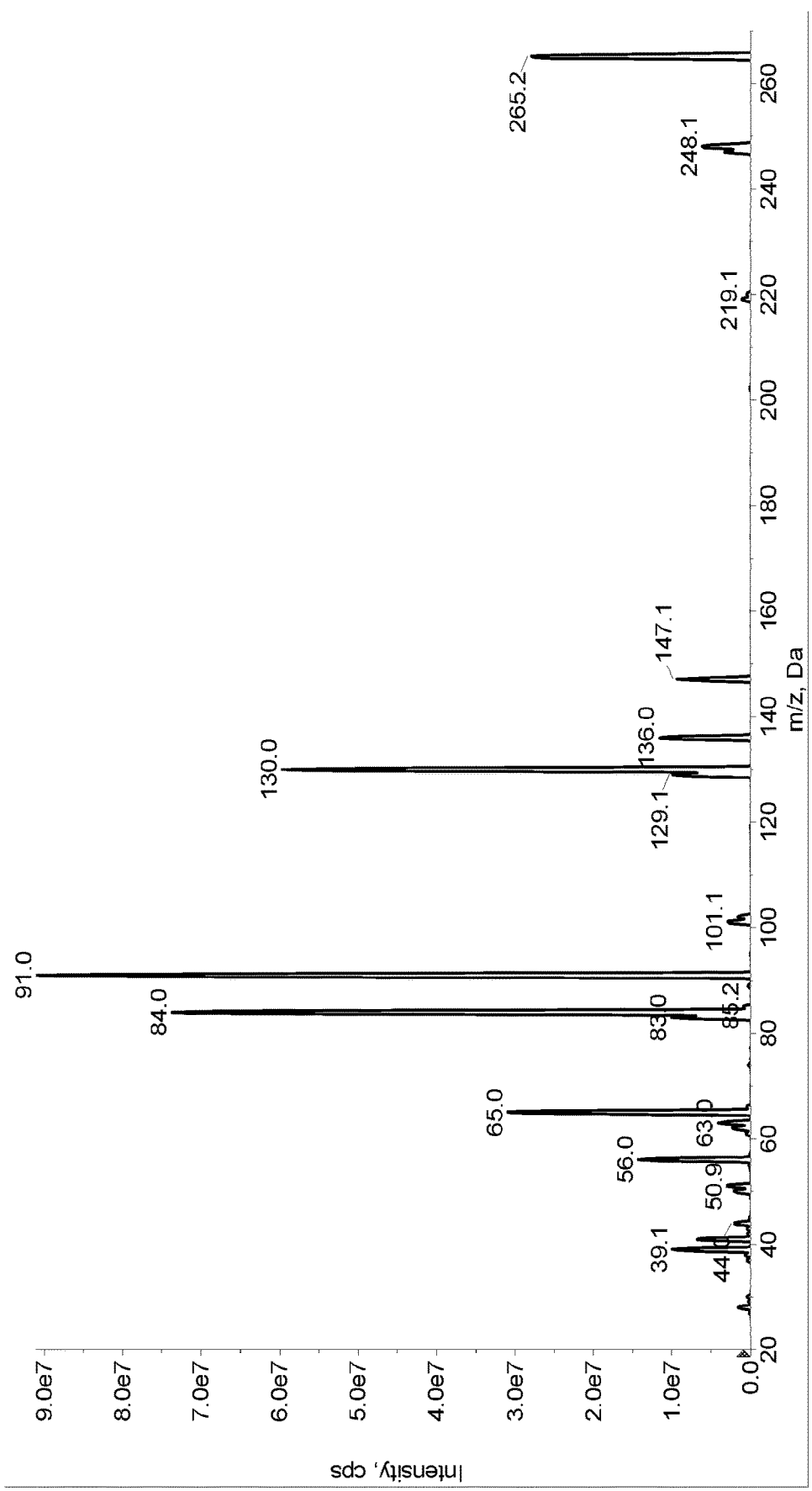
FIG. 10 shows exemplary parent and daughter ion peaks generated from tandem mass spectrometric fragmentation of phenylacetylglutamine.

MRM transitions that were generated for the quantitation of phenylacetylglutamine in positive ionization mode include those produced by fragmenting a parent ion having m/z of about 265.0±0.5 to produce daughter ions having m/z of about 91.0±0.5, 248.1±0.5, 219.1±0.5, 147.1±0.5, 136.0±0.5, 130.0±0.5, 129.1±0.5, 101.1±0.5, 84.0±0.5, 83.0±0.5, 65.0±0.5, 56.0±0.5, 50.9±0.5, 44.0±0.5, 40.9±0.5, 39.1±0.5, and 28.0±0.5. These parent and daughter ion peaks generated from tandem mass spectrometric fragmentation of phenylacetylglutamine are illustrated in FIG. 10. Any of the daughter ions may be selected for quantitation. In this example, the daughter ion used for quantitation of phenylacetylglutamine has m/z of about 91.0±0.5. The calibration range for phenylacetylglutamine was determined to be 0.100 to 20.0 µg/mL.

Figure 11:
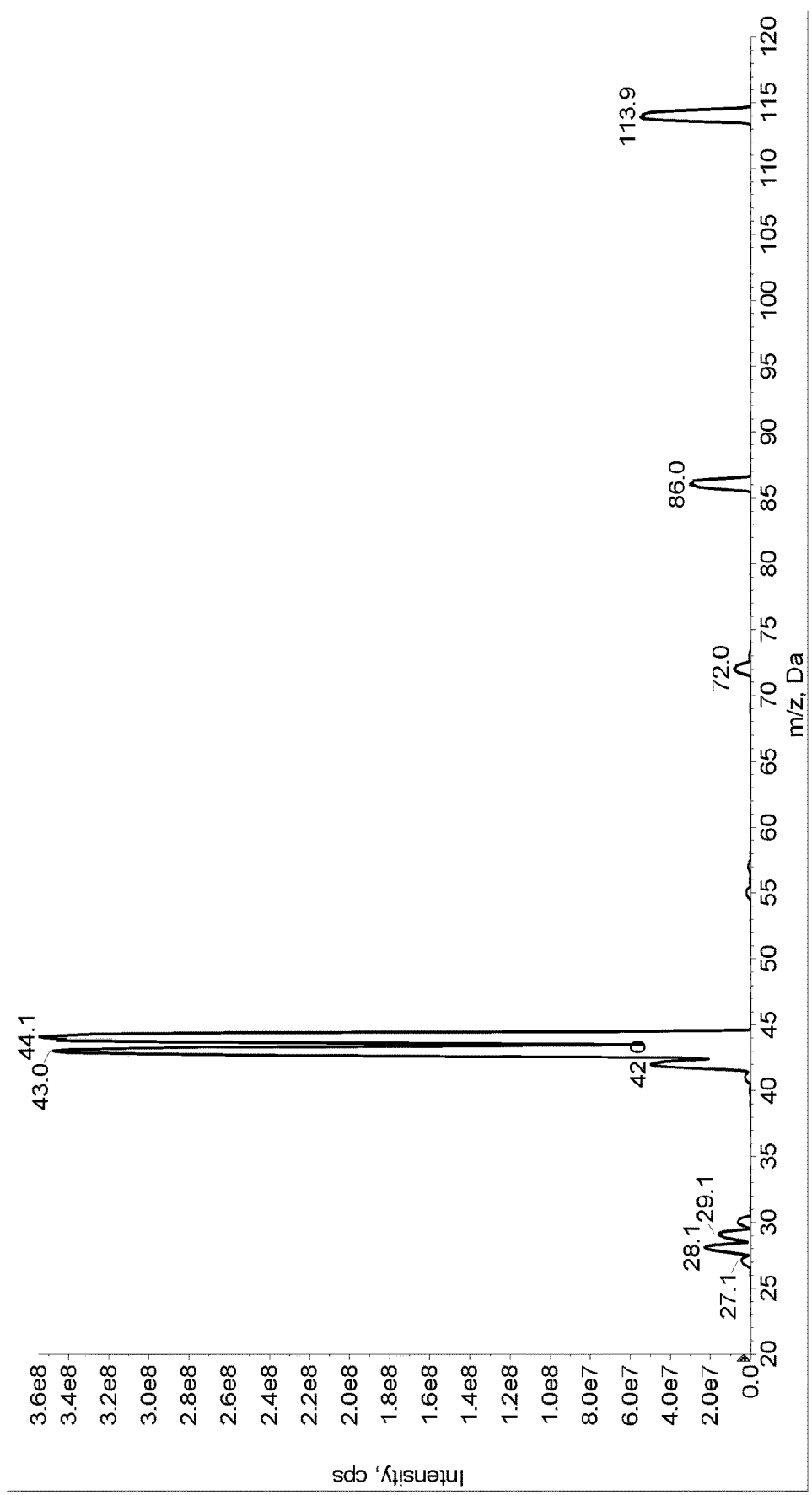
FIG. 11 shows exemplary parent and daughter ion peaks generated from tandem mass spectrometric fragmentation of creatinine.

MRM transitions that were generated for the quantitation of creatinine in positive ionization mode include those produced by fragmenting a parent ion having m/z of about 113.9±0.5 to produce daughter ions having a m/z of about 43.0±0.5, 86.0±0.5, 72.0±0.5, 44.1±0.5, 42.0±0.5, and 28.1±0.5. These parent and daughter ion peaks generated from tandem mass spectrometric fragmentation of creatinine are illustrated in FIG. 11. Any of the daughter ions may be selected for quantitation. In this example, the daughter ion used for quantitation of creatinine has a m/z of about 43.0±0.5. The calibration range for creatinine was determined to be 2.00 to 200 µg/mL.

Figure 12:
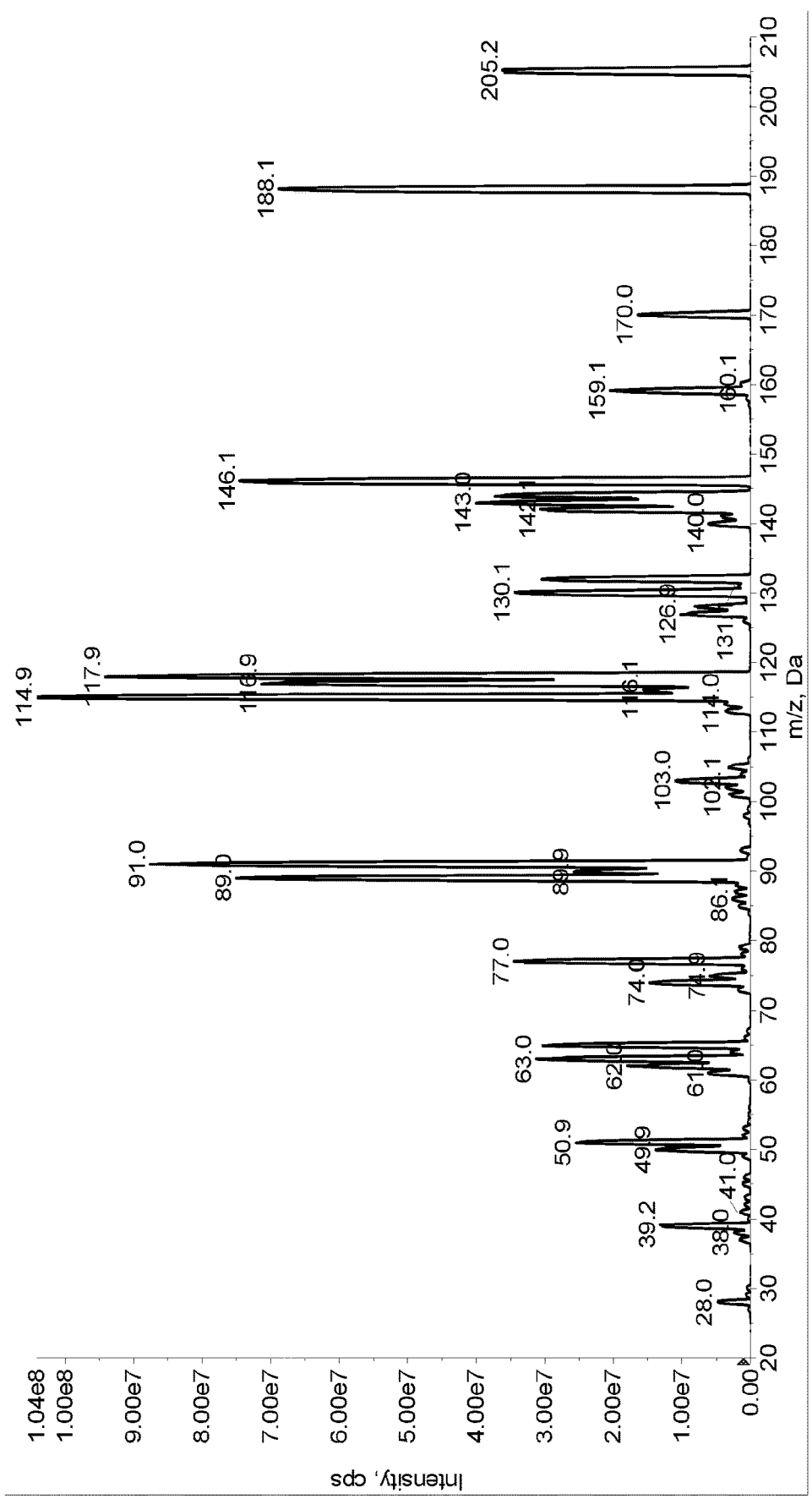
FIG. 12 shows exemplary parent and daughter ion peaks generated from tandem mass spectrometric fragmentation of tryptophan.

MRM transitions that were generated for the quantitation of tryptophan in positive ionization mode include those produced by fragmenting a parent ion having a m/z of about 205.0±0.5 to produce daughter ions having m/z of about 146.0±0.5, 191-193±0.5, 173-174±0.5, 163-164±0.5, 144.8-151.2±0.5, 117.1-122.1±0.5, 102.9-110.1±0.5, 89.9-96.0±0.5, 74.1-81.1±0.5, 60.9-68.9±0.5, 50.1-54.1±0.5, 38.0-43.1±0.5, and 28.0-29.0±0.5. These parent and daughter ion peaks generated from tandem mass spectrometric fragmentation of tryptophan are illustrated in FIG. 12. Any of the daughter ions may be selected for quantitation. In this example, the daughter ion used for quantitation of tryptophan has a m/z of about 146.0±0.5. The calibration range for tryptophan was determined to be 1.00 to 100 µg/mL.

Figure 13:
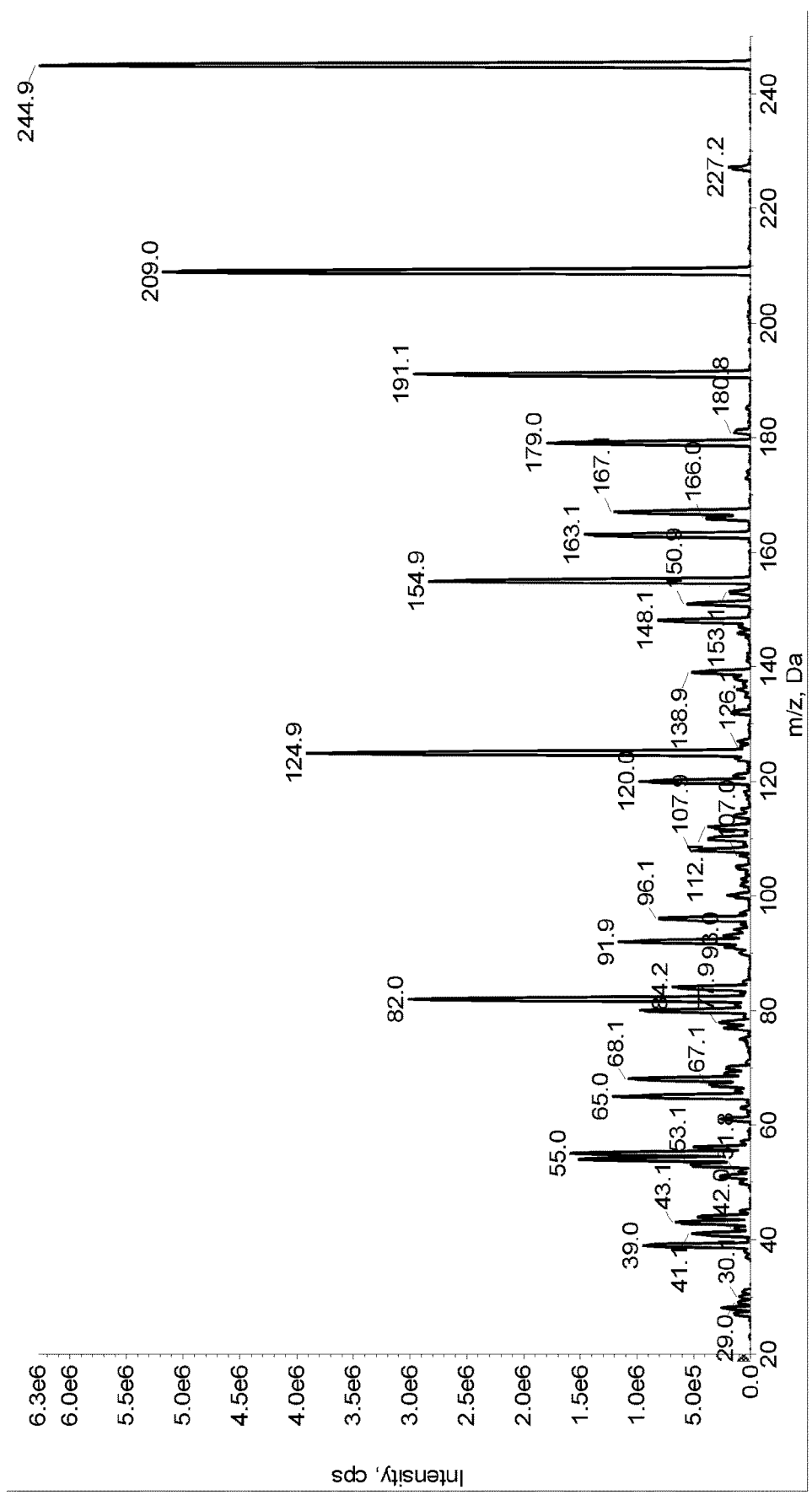
FIG. 13 shows exemplary parent and daughter ion peaks generated from tandem mass spectrometric fragmentation of pseudouridine.

MRM transitions that were generated for the quantitation of pseudouridine in positive ionization mode include those produced by fragmenting a parent ion having a m/z of about 244.9±0.5 to produce daughter ions having m/z of about 191.0±0.5, 209.0±0.5, 179.0±0.5, 167.0±0.5, 163.0±0.5, 154.8±0.5, 151.0±0.5, 148.0±0.5, 139.0±0.5, 125.0±0.5, 120.0±0.5, 111.8±0.5, 109.8±0.5, 107.8±0.5, 96.0±0.5, 92.0±0.5, 84.0±0.5, 82.0±0.5, 80.0±0.5, 68.0±0.5, 65.2±0.5, 55.0±0.5, 54.0±0.5, 43.0±0.5, 41.0±0.5, and 39.0±0.5. These parent and daughter ion peaks generated from tandem mass spectrometric fragmentation of pseudouridine are illustrated in FIG. 13. Any of the daughter ions may be selected for quantitation. In this example, the daughter ion used for quantitation of pseudouridine has a m/z of about 191.0±0.5. The calibration range for pseudouridine was determined to be 10.0 to 400 µg/mL.

Figure 14A:
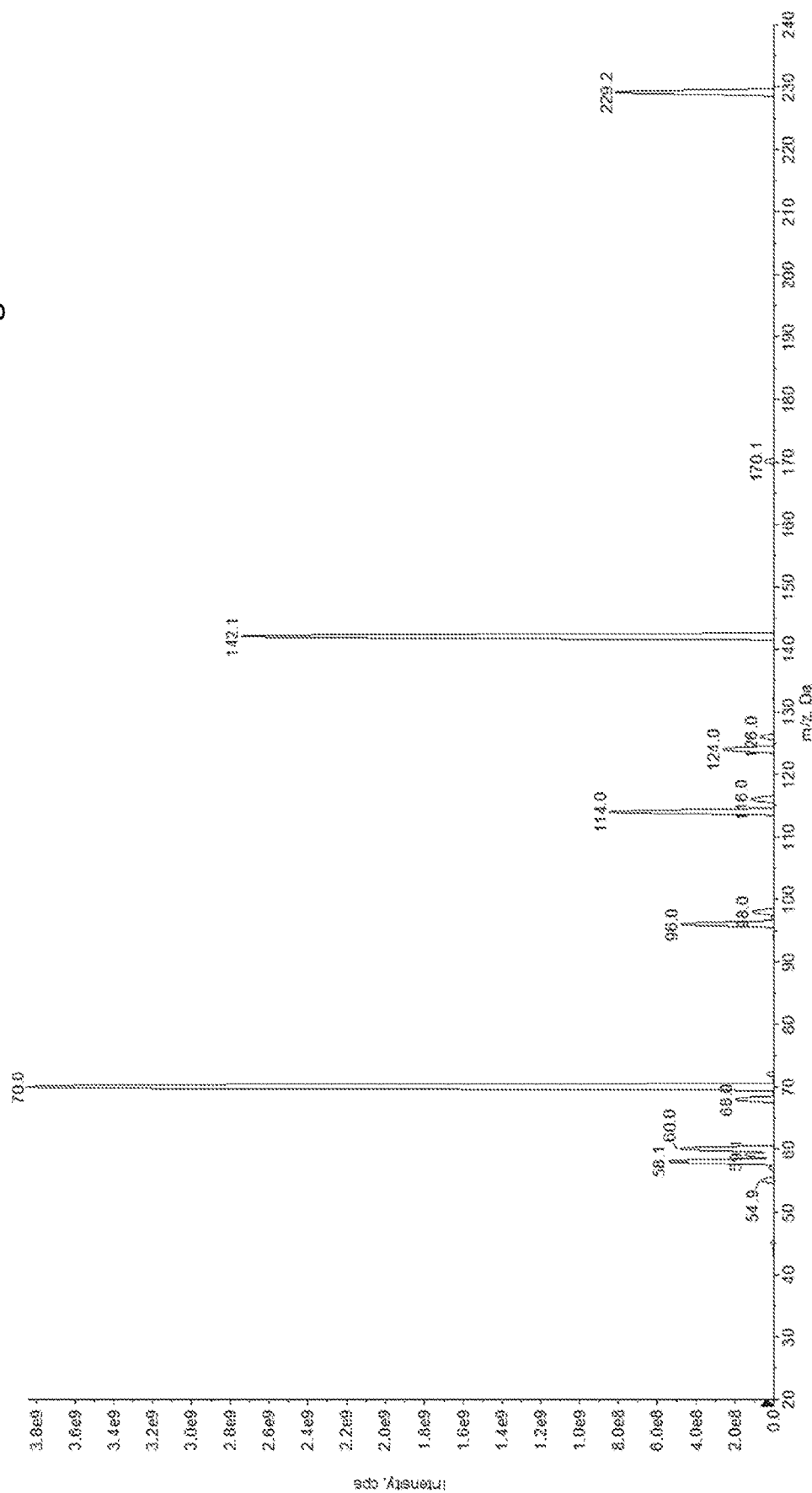
FIGS. 14A-B show exemplary parent and daughter ion peaks generated from tandem mass spectrometric fragmentation of TMAP in positive ionization mode (A) and negative ionization mode (B).
Figure 14B:
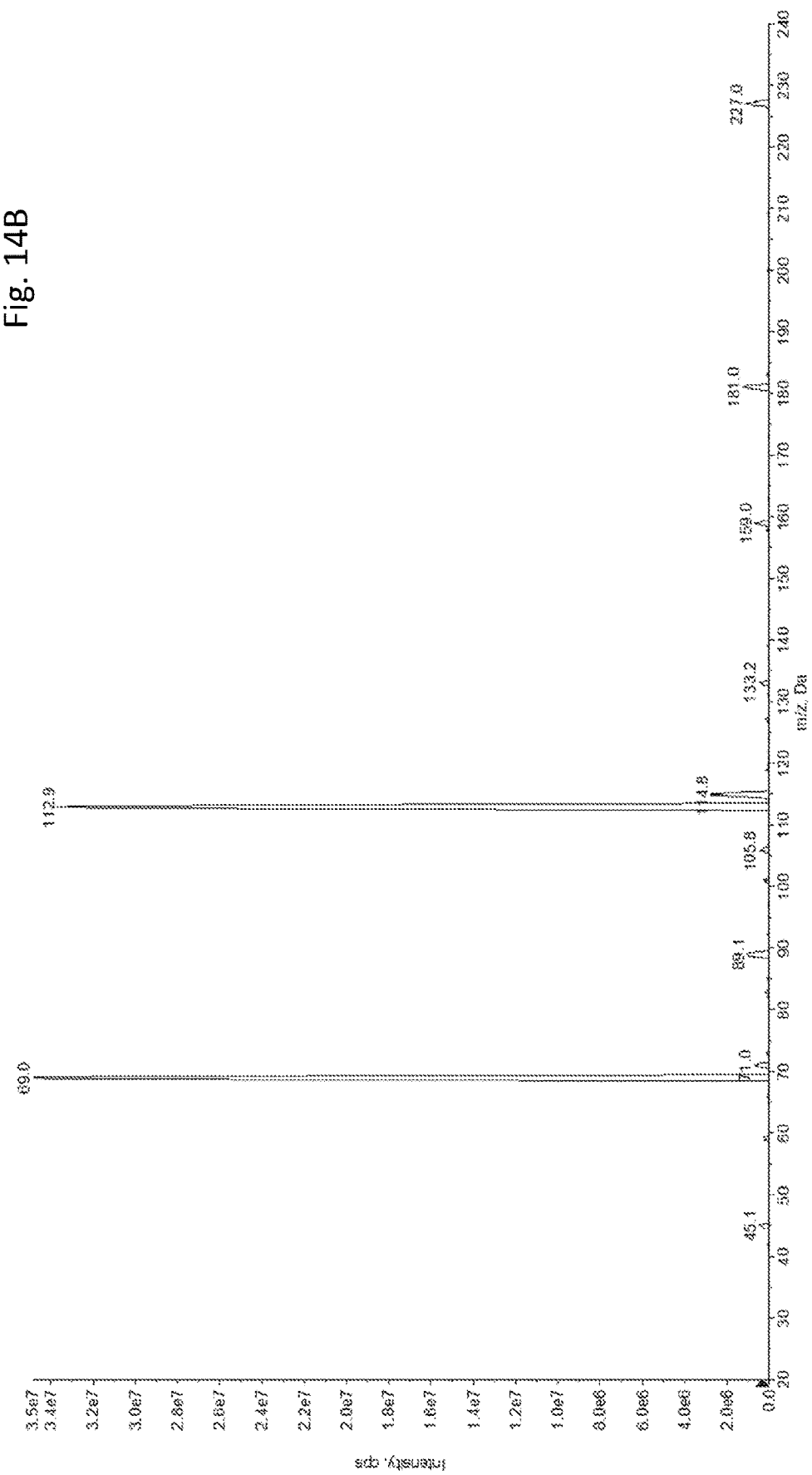

MRM transitions that were generated for the quantitation of TMAP in positive ionization mode include those produced by fragmenting a parent ion having a m/z of about 229.1±0.5 to produce daughter ions having m/z of about 170.1±0.5, 142.2±0.5, 126.0±0.5, 124.0±0.5, 116.0±0.5, 114.0±0.5, 98.0±0.5, 96.0±0.5, 70.0±0.5, 68.0±0.5, 60.0±0.5, 59.1±0.5, 58.1±0.5, 54.9±0.5, 227.0±0.5, 181.0±0.5, 159.0±0.5, 133.2±0.5, 114.8±0.5, 112.9±0.5, 105.8±0.5, 89.1±0.5, 71.0±0.5, 69.0±0.5, and 45.1±0.5. Any of the daughter ions may be selected for quantitation. For example, daughter ions having a m/z of about 58.1±0.5, 70.0±0.5, 114.0±0.5, or 142.2±0.5 may be used for the quantitation of TMAP. These parent and daughter ion peaks generated from tandem mass spectrometric fragmentation of TMAP are illustrated in FIG. 14.

B. MS/MS Method 2

In another example, a method was developed to detect in the same injection the levels of one or more, two or more, and up to all six analytes selected from the group consisting of pseudouridine, N-acetylthreonine, meso-erythritol, arabitol, myo-inositol, N-acetylserine and combinations thereof. The eluent from the chromatography column described in Example 1, Chromatography Method 2, was directly and automatically introduced into the electrospray source of a mass spectrometer. Water:acetonitrile (90:10) was used for the strong/seal wash; acetonitrile:water (90:10) was used for the weak wash.

The instruments were operated in negative MRM mode. Ionspray voltage was set at −4.0 kV, source temperature at 550° C., and curtain gas at 20 psi; nebulizer and desolvation gas flow rates were set at 70 psi, and CAD gas at medium.

Exemplary ions that were generated for the quantitation of pseudouridine, N-acetylthreonine, meso-erythritol, arabitol, myo-inositol, and N-acetylserine are shown in Table 4. The parent ions are listed under the column headed "Parent ion (m/z)", and the daughter ions used for quantitation in this example are listed in the column labeled "Daughter ion for quantitation (m/z)". The choice of daughter ion for quantitation in this example was optimized for sensitivity across the analytical measurement range; however, any of the daughter ions may be selected to replace or augment the daughter ions used for quantitation in the examples.

TABLE 4

Ions useful for quantitation of analytes

| Analyte | Parent ion (m/z) | Daughter ion for quantitation (m/z) | Additional daughter ions (m/z) (all ±0.5) |
|---|---|---|---|
| pseudouridine | 242.9 ± 0.5 | 153.0 ± 0.5 | 182.8, 151.9, 139.9, 138.9, 124.0, 110.8, 109.9, 96.0, 82.0, 55.0, 42.0, 41.0 |
| Pseudouridine-$^{13}$C,$^{15}$N$_2$ | 245.9 ± 0.5 | 156.0 ± 0.5 | 186.0, 141.8, 141.0, 114.0, 111.0, 97.0, 44.1 |
| Acetyl-L-threonine | 159.9 ± 0.5 | 73.9 ± 0.5 | 118.1, 115.8, 97.9, 71.9, 70.9, 70.1, 56.1, 54.0, 42.0, 40.9. 26.0 |
| N-Acetyl-d$_3$-L-threonine-d$_2$ | 165.0 ± 0.5 | 102.0 ± 0.5 | 120.0, 103.0, 82.2, 77.0, 76.0, 74.1 |
| meso-Erythritol | 120.9 ± 0.5 | 88.9 ± 0.5 | 120.0, 119.0, 105.9, 103.0, 100.9, 93.9, 92.8, 79.9, 77.0, 70.9, 67.9, 65.8, 65.0, 58.9, 52.0, 43.2, 40.0 |
| Erythritol-$^{13}$C$_4$ | 124.9 ± 0.5 | 73.9 ± 0.5 | 123.0, 110.0, 107.0, 105.0, 98.0, 95.2, 91.9, 87.0, 82.1, 81.1, 76.1, 67.0, 65.9, 61.0, 60.1, 58.0, 44.8, 41.2, 39.9, 25.8 |
| D-Arabitol | 150.9 ± 0.5 | 88.9 ± 0.5 | 149.1, 136.0, 133.0, 131.1, 119.0, 112.8, 108.2, 103.1, 100.9, 96.8, 91.8, 84.9, 83.0, 81.9, 78.8, 77.0, 73.0, 70.9, 68.9, 66.9, 59.0, 57.0, 55.0, 45.0, 42.9, 41.2 |
| D-Arabinitol-$^{13}$C$_5$ | 155.9 ± 0.5 | 91.9 ± 0.5 | 154.1, 138.0, 136.0, 123.1, 118.1, 107.0, 104.9, 102.0, 88.9, 86.9, 76.0, 74.0, 73.2, 61.0, 59.9, 58.0, 45.0, 43.1 |
| myo-Inositol | 178.9 ± 0.5 | 87.0 ± 0.5 | 177.2, 161.0, 159.0, 146.8, 141.0, 134.9, 128.8, 125.0, 122.7, 117.0, 112.8, 110.9, 100.9, 98.9, 97.0, 95.0, 90.8, 89.0, 85.0, 82.9, 81.0, 78.8, 74.8, 73.1, 70.9, 68.9, 59.0, 56.9, 55.0, 45.1, 43.0, 41.0 |
| myo-Inositol-d$_6$ | 184.9 ± 0.5 | 88.9 ± 0.5 | 181.8, 167.1, 164.1, 158.1, 144.9, 140.0, 131.9, 130.1, 128.9, 119.9, 118.9, 117.2, 104.1, 103.1, 102.0, 100.9, 97.9, 93.1, 90.0, 88.0, 85.9, 82.0, 80.8, 76.9, 74.1, 72.9, 72.1, 69.8, 62.1, 61.0, 60.1, 58.1, 57.0, 46.0, 45.0, 42.1 |
| N-acetylserine | 145.9 ± 0.5 | 74.0 ± 0.5 | 119.0, 116.0, 104.9, 103.9, 103.0, 97.9, 84.0, 81.0, 72.0, 70.0, 64.9, 60.8, 57.0, 42.0, 40.9 |

TABLE 4-continued

Ions useful for quantitation of analytes

| Analyte | Parent ion (m/z) | Daughter ion for quantitation (m/z) | Additional daughter ions (m/z) (all ±0.5) |
|---|---|---|---|
| Acetylserine-$d_3$ | 148.9 ± 0.5 | 117.0 ± 0.5 | 121.9, 106.9, 98.9, 87.0, 86.0, 74.9, 73.0, 70.9, 60.8, 59.0, 58.0, 45.0, 41.2, 42.0 |

C. MS/MS Method 3

In another example, a method was developed to detect in the same injection the levels of one or more, two or more, and up to all nine analytes selected from the group consisting of N-acetylthreonine, phenylacetylglutamine, tryptophan, creatinine, N-acetylalanine, 3-methylhistidine, trans-4-hydroxyproline, kynurenine, urea and combinations thereof, wherein, if the one or more assayed analytes is only one analyte, the one analyte is not creatinine. The eluent from the chromatography column described in Example 3, Chromatography Method 3, was directly and automatically introduced into the electrospray source of a mass spectrometer. Water:acetonitrile (90:10) was used for the strong/seal wash; acetonitrile:water (90:10) was used for the weak wash. The instrument was operated in positive multiple reaction monitoring (MRM) mode. Ionspray voltage was set at 4.0 kV, source temperature at 550° C., curtain gas (e.g., nitrogen) at 20 psi, and nebulizer and desolvation gas (e.g., nitrogen) flow rates at 75 psi, collisionally activated dissociation (CAD) gas (e.g., nitrogen) at medium.

Exemplary ions that were generated for the quantitation of N-acetylthreonine, phenylacetylglutamine, tryptophan, creatinine, N-acetylalanine, 3-methylhistidine, trans-4-hydroxyproline, kynurenine, and urea are shown in Table 5. The parent ions are listed under the column headed "Parent ion (m/z)", and the daughter ions used for quantitation in this example are listed in the column labeled "Daughter ion for quantitation (m/z)". The choice of daughter ion for quantitation in this example was optimized for sensitivity across the analytical measurement range; however, any of the daughter ions may be selected to replace or augment the daughter ions used for quantitation in the examples.

TABLE 5

Ions useful for quantitation of analytes

| Analyte | Parent ion (m/z) | Daughter ion for quantitation (m/z) | Additional daughter ions (m/z) (all ± 0.5) |
|---|---|---|---|
| Acetyl-L-threonine | 162.0 ± 0.5 | 74.1 ± 0.5 | 144.0, 126.1, 119.9, 116.1, 102.0, 97.9, 84.0, 70.0, 57.0, 56.0, 43.0, 28.1 |
| N-Acetyl-$d_3$-L-threonine-$d_2$ | 167.0 ± 0.5 | 77.1 ± 0.5 | 149.1, 131.9, 129.8, 125.9, 122.8, 121.0, 104.0, 91.0, 86.1, 76.0, 59.0, 58.1, 45.9, 43.0, 31.1, 29.2, 28.0 |
| Phenylacetyl-L-glutamine | 265.0 ± 0.5 | 91.0 ± 0.5 | 248.1, 219.1, 147.1, 136.0, 130.0, 129.1, 101.1, 84.0, 83.0, 65.0, 56.0, 50.9, 44.0, 40.9, 39.1, 28.0 |
| Phenylacetylglutamine-$d_5$ | 270.0 ± 0.5 | 96.3 ± 0.5 | 253.3, 224.3, 147.0, 141.3, 130.0, 100.8, 84.0, 69.0, 68.1, 56.0, 41.1, 28.1 |
| Creatinine | 113.9 ± 0.5 | 43.0 ± 0.5 | 86.0, 72.0, 44.1, 42.0, 28.1 |
| Creatinine-$d_3$ | 116.9 ± 0.5 | 47.0 ± 0.5 | 89.2, 43.1, 29.1, 28.0 |
| L-Tryptophan | 205.0 ± 0.5 | 146.0 ± 0.5 | 188.1, 170.0, 159.1, 144.0, 143.0, 142.0, 140.0, 132.0, 130.1, 128.1, 126.9, 117.9, 116.9, 114.9, 103.0, 91.0, 89.9, 89.0, 77.0, 74.9, 74.0, 64.9, 63.0, 62.0, 61.0, 50.9, 49.9, 39.2, 28.0 |
| L-Tryptophan-$d_5$ | 210.0 ± 0.5 | 150.1 ± 0.5 | 191-193, 173-174, 163-164, 144.8-151.2, 117.1-122.1, 102.9-110.1, 89.9-96.0, 74.1-81.1, 60.9-68.9, 50.1-54.1, 38.0-43.1, 28.0-29.0 |

TABLE 5-continued

Ions useful for quantitation of analytes

| Analyte | Parent ion (m/z) | Daughter ion for quantitation (m/z) | Additional daughter ions (m/z) (all ± 0.5) |
|---|---|---|---|
| N-Acetyl-L-alanine | 131.9 ± 0.5 | 89.9 ± 0.5 | 114.1, 86.1, 44.0 |
| N-Acetyl-L-alanine-$d_4$ | 136.0 ± 0.5 | 94.0 ± 0.5 | 118.1, 90.0, 48.0 |
| 3-Methyl-L-histidine | 170.0 ± 0.5 | 94.9 ± 0.5 | 109.1, 97.0, 96.0, 92.9, 83.0, 81.0, 80.1, 70.2, 67.9, 67.0, 55.0, 54.0, 42.0, 41.0 |
| 3-Methyl-L-histidine-$d_3$ | 173.0 ± 0.5 | 127.0 ± 0.5 | 129.1, 112.0, 100.1, 83.0 |
| trans-4-Hydroxy-L-proline | 131.9 ± 0.5 | 68.0 ± 0.5 | 114.2, 86.0, 58.0, 41.0 |
| trans-4-Hydroxy-L-proline-$d_3$ | 134.9 ± 0.5 | 71.1 ± 0.5 | 117.1, 89.0, 70.0, 61.0 |
| L-Kynurenine | 209.0 ± 0.5 | 94.0 ± 0.5 | 192.1, 191.2, 174.0, 164.1, 163.1, 150.0, 146.1, 136.0, 119.9, 118.1, 98.9, 88.0, 73.9 |
| Kynurenine-$d^6$ | 215.0 ± 0.5 | 98.0 ± 0.5 | 198.2, 197.2, 179.1, 170.1, 169.2, 155.1, 154.1, 151.0, 142.0, 141.0, 125.0, 118.0, 99.9, 99.1, 97.0, 89.9, 74.2 |
| Urea | 60.9 ± 0.5 | 29.2 ± 0.5 | 44.0, 43.0, 42.1, 28.0, 27.1 |
| Urea-$^{13}C$, $^{15}N_2$ | 63.9 ± 0.5 | 29.1 ± 0.5 | 46.0, 45.0, 44.1, 30.0 |

D. MS/MS Method 4

In another example, a method was developed to detect in the same injection the levels of one or more, two or more, and up to all three analytes selected from the group consisting of tryptophan, C-glycosyltryptophan, and 3-indoxyl sulfate. The eluent from the chromatography column described in Example 1, Chromatography Method 4, was directly and automatically introduced into the electrospray source of a mass spectrometer. Methanol was used for needle wash. The instrument was operated in negative MRM mode. Ionspray voltage was set at −4.5 kV, source temperature at 550° C., and curtain gas at 20 psi; nebulizer and desolvation gas flow rates were set at 60 psi and 65 psi, respectively, and CAD gas at high.

Exemplary ion pairs that may be used for the quantitation of tryptophan, C-glycosyltryptophan, and 3-indoxylsulfate are shown in Table 6. The parent ions are listed under the column headed "Parent ion (m/z)", and the daughter ions used for quantitation in this example are listed in the column labeled "Daughter ion for quantitation (m/z)". The choice of daughter ion for quantitation in this example was optimized for sensitivity across the analytical measurement range; however, any of the daughter ions may be selected to replace or augment the daughter ions used for quantitation in the examples.

TABLE 6

Ions useful for quantitation of analytes

| Analyte | Parent ion (m/z) | Daughter ion for quantitation (m/z) | Additional daughter ions (m/z) (all ± 0.5) |
|---|---|---|---|
| L-Tryptophan | 202.9 ± 0.5 | 115.9 ± 0.5 | 185.9, 158.9, 141.9, 130.0, 74.1, 72.2, 59.0, 44.9 |
| L-Tryptophan-$d_5$ | 208.0 ± 0.5 | 119.9 ± 0.5 | 190.2, 164.2, 162.2, 147.1, 146.0, 134.1, 121.0, 120.0, 76.0, 75.0, 73.9, 72.8, 72.0 |
| 3-indoxylsulfate | 211.8 + 0.5 | 79.9 ± 0.5 | 132.0, 104.0, 80.9, 77.0 |
| 3-indoxylsulfate-$d_4$ | 215.9 ± 0.5 | 80.9 ± 0.5 | 136.0, 79.9 |
| Manno-L-tryptophan | 365.2 ± 0.5 | 245.0 ± 0.5 | 130.0, 142.0, 156.0, 116.0 |
| Manno-L-tryptophan-$d_4$ | 369.2 ± 0.5 | 249.0 ± 0.5 | |

D. MS/MS Method 5

In another example, a method was developed to detect in the same injection the levels of one or more, two or more, and up to all ten analytes selected from the group consisting of meso-erythritol, D-arabitol, inositol, 3-indoxyl sulfate, L-tryptophan, phenylacetylglutamine, creatinine, pseudouridine, N-acetylthreonine, and N-acetylserine, and combinations thereof. The eluent from the chromatography column described in Example 1, Chromatography Method 6, was directly and automatically introduced into the electrospray source of a mass spectrometer.

In another example, the eluent from the chromatography column described in Example 1, Chromatography Method 7, was directly and automatically introduced into the electrospray source of a mass spectrometer. The method detected, in the same injection, the levels of one or more, two or more, and up to all five analytes selected from the group consisting of D-arabitol, phenylacetylglutamine, creatinine, pseudouridine, N-acetylthreonine, and combinations thereof, wherein, if the one or more assayed analytes is only one analyte, the one analyte is not creatinine.

In another example, the eluent from the chromatography column described in Example 1, Chromatography Method 8, was directly and automatically introduced into the electrospray source of a mass spectrometer. The method detected, in the same injection, the levels of one or more, two or more, and up to all six analytes selected from the group consisting of inositol, L-tryptophan, phenylacetylglutamine, creatinine, pseudouridine, N-acetylthreonine, and combinations thereof, wherein, if the one or more assayed analytes is only one analyte, the one analyte is not creatinine. Acetonitrile:Water (50:50) was used for the needle wash. The instrument was operated in negative MRM mode. Ionspray voltage was set at −4.5 kV, source temperature at 550° C., and curtain gas at 20 psi; nebulizer and desolvation gas flow rates were set at 50 psi, and CAD gas at medium.

Exemplary ion pairs that may be used for the quantitation of meso-erythritol, D-arabitol, inositol, 3-indoxyl sulfate, L-tryptophan, phenylacetylglutamine, creatinine, pseudouridine, N-acetylthreonine, and N-acetylserine are shown in Table 7. The parent ions are listed under the column headed "Parent ion (m/z)", and the daughter ions used for quantitation in this example are listed in the column labeled "Daughter ion for quantitation (m/z)". The choice of daughter ion for quantitation in this example was optimized for sensitivity across the analytical measurement range; however, any of the daughter ions may be selected to replace or augment the daughter ions used for quantitation in the examples.

TABLE 7

Ions useful for quantitation of analytes

| Analyte | Parent ion ± 0.5 (m/z) | Daughter ion for quantitation ± 0.5 (m/z) |
|---|---|---|
| Meso-erythritol | 120.9 | 89 |
| Meso-erythritol-$^{13}C_4$ | 124.9 | 74 |
| D-Arabitol | 150.9 | 88.9 |
| D-Arabitol-$^{13}C_5$ | 155.9 | 91.9 |
| Inositol | 178.9 | 87 |
| Inositol-$d_6$ | 184.9 | 88.9 |
| 3-Indoxyl sulfate | 211.8 | 103.9 |
| 3-Indoxyl sulfate-$d_4$ | 215.9 | 107.9 |
| L-Tryptophan | 202.9 | 115.9 |
| L-Tryptophan-$d_5$ | 207.9 | 119.9 |
| Phenylacetylgluta mine | 262.9 | 42 |

TABLE 7-continued

Ions useful for quantitation of analytes

| Analyte | Parent ion ± 0.5 (m/z) | Daughter ion for quantitation ± 0.5 (m/z) |
|---|---|---|
| Phenylacetylgluta mine-$d_5$ | 268 | 42 |
| Creatinine | 111.9 | 67.9 |
| Creatinine-$d_3$ | 114.9 | 68 |
| Pseudouridine | 242.9 | 42 |
| Pseudouridine-$^{13}C$, $^{15}N_2$ | 245.9 | 156 |
| N-Acetyl-DL-threonine | 159.9 | 73.9 |
| N-Acetyl-$d_3$-DL-threonine-$d_2$ | 164.9 | 102 |
| N-Acetylserine | 145.9 | 74 |
| N-Acetylserine-$d_3$ | 148.9 | 117 |

Example 3: Method Validation

A. Chromatography Method 1 and MS/MS Method 1

The analytical performance of the combination of Chromatography Method 1 and MS/MS Method 1 resulted in the quantitation of a plurality of up to five analytes in a single injection with a run time of 3.7 minutes.

The precision of the method for measuring a plurality of five analytes was evaluated at three QC levels (low, mid, and high) in plasma and serum. Three replicates per QC level per matrix were analyzed in two runs per day over 20 days for a total of 40 runs. A total of 120 replicates per QC level were included in the inter-day CV calculations for each analyte per matrix. The inter-day precision was less than 6.3% at each QC level in plasma and less than 7.1% at each QC level in serum. The results are presented in Table 8. Linear responses ($R^2>0.98$) were observed over a 100 fold range for N-acetylthreonine, creatinine, pseudouridine, and tryptophan, and over a 200-fold range for phenylacetylglutamine. Calibration ranges were selected based on analysis of over 1,000 plasma and serum samples.

TABLE 8

Inter-day Precision for a Plurality of Analytes in Plasma and serum.

| Analyte | QC Level | SERUM Mean (µg/mL) | SERUM % CV | PLASMA Mean (µg/mL) | PLASMA % CV |
|---|---|---|---|---|---|
| Acetylthreonine (n = 120) | Low | 0.0772 | 5.9 | 0.0758 | 6.0 |
| | Mid | 0.889 | 5.9 | 0.891 | 5.3 |
| | High | 1.78 | 4.8 | 1.64 | 5.4 |
| Creatinine (n = 120) | Low | 7.42 | 7.1 | 6.70 | 5.3 |
| | Mid | 88.9 | 6.6 | 87.0 | 4.9 |
| | High | 172 | 5.5 | 158 | 5.4 |
| Phenylacetylglutamine (n = 120) | Low | 0.328 | 6.4 | 0.327 | 6.3 |
| | Mid | 8.15 | 5.1 | 8.19 | 4.2 |
| | High | 16.0 | 3.8 | 14.7 | 3.8 |
| Pseudouridine (n = 120) | Low | 1.27 | 6.1 | 1.23 | 5.1 |
| | Mid | 16.4 | 5.1 | 16.4 | 4.8 |
| | High | 32.1 | 3.7 | 29.8 | 4.4 |
| Tryptophan (n = 120) | Low | 4.07 | 6.9 | 3.26 | 6.1 |
| | Mid | 44.5 | 5.4 | 43.4 | 4.9 |
| | High | 88.0 | 4.3 | 80.6 | 4.8 |

Accuracy and precision of dilution QCs in serum and plasma were evaluated to accurately measure samples with analyte values above the ULOQ (i.e., outside the calibration range). The dilution QCs were prepared by diluting the high QC matrix 5-fold with fatty acid-free BSA solution. Three replicates of dilution QCs per matrix were analyzed in two runs per day over five days for a total of 10 runs. A total of 30 replicates were included in the inter-day accuracy and precision calculations. The inter-day accuracy (as compared to the measured high QC value) in serum was greater than 94.5% and the inter-day precision was less than 7.6%; the inter-day accuracy in plasma was greater than 94.7% and the inter-day precision was less than 4.4%. The results are presented in Table 9.

TABLE 9

Inter-Day Accuracy and Precision of the 5X Dilution QC

| | N-acetylthreonine (n = 30) | Creatinine (n = 30) | Phenylacetyl glutamine (n = 30) | Pseudouridine (n = 30) | Tryptophan (n = 30) |
|---|---|---|---|---|---|
| SERUM | | | | | |
| Mean (mg/mL) | 1.80 | 177 | 17.0 | 33.6 | 83.3 |
| % CV | 7.6 | 5.8 | 7.0 | 6.0 | 6.8 |
| % Accuracy | 97.9 | 101 | 94.5 | 95.0 | 107 |
| PLASMA | | | | | |
| Mean (mg/mL) | 1.66 | 163 | 15.5 | 30.3 | 76.3 |
| % CV | 3.7 | 4.0 | 3.2 | 3.9 | 4.4 |
| % Accuracy | 100 | 101 | 94.7 | 99.6 | 107 |

The precision at the LLOQ was evaluated. The signal-to-noise ratio for every analyte was greater than 5:1. Three replicates of the LLOQ samples were analyzed in two runs per day over 15 days for a total of 30 runs. A total of 90 replicates of the LLOQ were included in the inter-day % CV calculations for each analyte. All intra- and inter-day precision was less than 2.8% CV; the data are shown in Table 10. These results indicated that quantitation of the plurality of analytes at the lower limit was highly precise.

TABLE 10

Intra- and Inter-Day Precision at the LLOQ.

| | LLOQ Concentration (μg/mL) | | | | |
|---|---|---|---|---|---|
| Day | 0.0200 N-acetylthreonine (% RSD) | 2.00 Creatinine (% RSD) | 0.100 Phenylacetyl glutamine (% RSD) | 0.400 Pseudouridine (% RSD) | 1.00 Tryptophan (% RSD) |
| 1 (n = 6) | 5.2 | 5.8 | 11.2 | 4.7 | 9.6 |
| 2 (n = 6) | 7.6 | 6.3 | 10.0 | 5.4 | 10.9 |
| 3 (n = 6) | 5.7 | 3.3 | 6.5 | 4.8 | 7.0 |
| 4 (n = 6) | 9.9 | 2.6 | 4.7 | 3.2 | 5.3 |
| 5 (n = 6) | 4.6 | 4.2 | 4.2 | 3.7 | 3.5 |
| 6 (n = 6) | 6.1 | 7.6 | 3.7 | 7.6 | 8.1 |
| 7 (n = 6) | 10.1 | 8.1 | 8.1 | 9.8 | 6.2 |
| 8 (n = 6) | 4.3 | 8.8 | 5.5 | 4.1 | 6.8 |
| 9 (n = 6) | 3.1 | 5.5 | 6.6 | 10.1 | 9.2 |
| 10 (n = 6) | 8.9 | 3.1 | 7.1 | 6.0 | 5.7 |
| 11 (n = 6) | 5.1 | 5.3 | 5.7 | 4.6 | 6.5 |
| 12 (n = 6) | 7.1 | 9.9 | 8.6 | 5.7 | 6.1 |
| 13 (n = 6) | 4.9 | 3.7 | 3.6 | 8.4 | 12.8 |
| 14 (n = 6) | 5.0 | 6.6 | 12.3 | 5.9 | 7.2 |
| 15 (n = 6) | 5.0 | 6.5 | 4.6 | 5.9 | 5.3 |
| Intel-Day (n = 90) | 6.5 | 6.4 | 8.6 | 7.0 | 9.3 |

In order to assess the recovery of analytes during the extraction, QC samples in serum and plasma were fortified with known concentrations of analytes. Six replicates of the spiked QC samples were extracted and analyzed along with regular QC samples in triplicate. Recovery of the spiked amount was calculated after subtraction of the amount in the spiked QC samples. The recoveries for the five analytes were determined to be 97.4% to 113% in serum and 103% to 110% in plasma for the five analytes. The data are presented in Table 11.

TABLE 11

| | Recovery of Analytes | | | | |
|---|---|---|---|---|---|
| | N-acetylthreonine | Creatinine | Phenylacetylglutamine | Pseudouridine | Tryptophan |
| | SERUM | | | | |
| % Recovery | 103 | 97.4 | 98.5 | 103 | 113 |
| | PLASMA | | | | |
| % Recovery | 105 | 110 | 105 | 103 | 109 |

To evaluate the interference of the sample type on quantitation of analytes, a post column infusion experiment with an internal standard solution was performed concurrent with analysis of ten individual lots of plasma and serum samples extracted without internal standards. Internal standard transitions were monitored and the level of suppression/enhancement at the retention times of the analytes was observed. Tryptophan demonstrated a matrix effect in the retention area and eluted just prior to a suppression that appeared to exceed 25% of the unaffected signal. However, since the co-eluting internal standards in this assay are isotopically-labeled, any mild sample type effect should occur similarly for the analyte and internal standard. By using the peak area ratio of the analyte to internal standard for quantitation, the sample type effect is thus compensated for in the final calculation.

Interference was also evaluated for icterus, lipidemia, known isomers of the analytes, and pharmaceuticals including statins, NSAIDs, pain relievers, antihistamines, and anti-diabetics. Chromatography Method 1 and MS/MS Method 1 was determined to be free of interference from the tested interference conditions.

B. Chromatography Method 2 and MS/MS Method 2

The analytical performance of the combination of Chromatography Method 2 and MS/MS Method 2 resulted in the quantitation of a plurality of up to six analytes selected from the group consisting of pseudouridine, N-acetylthreonine, meso-erythritol, arabitol, myo-inositol, and N-acetylserine in a single injection with a run time of 7.0 minutes.

The precision of the method for measuring a plurality of six analytes was evaluated in a representative lot of plasma and serum. Twelve replicates for plasma and six replicates for serum were analyzed over three runs. The inter-run precision was less than 7.3% in plasma and less than 20% in serum. The results are presented in Table 12.

TABLE 12

Inter-run Precision for a Plurality of Analytes in Plasma and Serum.

| | Plasma | | Serum | |
|---|---|---|---|---|
| Analyte | Inter-Run Mean (µg/mL) (n = 36) | Inter-Run % RSD (n = 36) | Inter-Run Mean (µg/mL) (n =18) | Inter-Run % RSD (n = 18) |
| pseudouridine | 0.645 | 2.6 | 0.778 | 20 |
| N-acetylthreonine | 0.0657 | 4.5 | 0.0721 | 10 |
| meso-erythritol | 0.459 | 7.3 | 0.749 | 5.3 |
| arabitol | 0.530 | 2.8 | 0.522 | 3.6 |
| myo-inositol | 3.58 | 2.5 | 5.08 | 2.8 |
| N-acetylserine | 0.100 | 6 | 0.102 | 4.3 |

The precision and accuracy at the LLOQ were evaluated. The signal-to-noise ratio for every analyte was greater than 5:1. Six replicates of the LLOQ samples were analyzed in three runs. A total of 18 replicates of the LLOQ were included in the inter-day % RSD and accuracy calculations for each analyte for each matrix. Inter-run precision was less than 18.0% for plasma and less than 13% for serum. Inter-run accuracy was between 98.7-104% for plasma and between 95.7-101.1% for serum. The data are shown in Table 13.

TABLE 13

Inter-Run Precision and Accuracy at the LLOQ.

| | Plasma (n = 18) | | | Serum (n = 18) | | |
|---|---|---|---|---|---|---|
| Analyte | Inter-Run Mean (µg/mL) | Inter-Run % RSD | Inter-Run Accuracy (%) | Inter-Run Mean (µg/mL) | Inter-Run % RSD | Inter-Run Accuracy (%) |
| pseudouridine | 0.0252 | 4.7 | 101 | 0.0249 | 13 | 100.4 |
| N-acetylthreonine | 0.00744 | 11.9 | 99.1 | 0.0075 | 9.4 | 100.67 |
| meso-erythritol | 0.0311 | 18 | 104 | 0.0304 | 9.0 | 98.5 |
| arabitol | 0.049 | 7.2 | 98.7 | 0.0495 | 8.7 | 101.1 |
| myo-inositol | 0.1 | 6.8 | 100 | 0.1043 | 7.8 | 95.7 |
| N-acetylserine | 0.015 | 4.8 | 99 | 0.0150 | 5.9 | 100 |

In order to assess the recovery of analytes during the extraction, QC samples in serum and plasma were fortified with known concentrations of analytes. Six replicates of the spiked QC samples were extracted and analyzed along with regular QC samples in triplicate. Recovery of the spiked amount was calculated after subtraction of the amount in the spiked QC samples. The recoveries for the six analytes were determined to be 80.4% to 97.5% in plasma and 75.6% to 96.0% in serum for the six analytes. The data are presented in Table 14.

TABLE 14

Recovery of Analytes

| Analyte | Plasma Average % Recovery | Serum Average % Recovery |
|---|---|---|
| pseudouridine | 94.4 | 75.6 |
| N-acetylthreonine | 90.7 | 89.4 |
| meso-erythritol | 97.5 | 93.4 |
| arabitol | 91.4 | 96.0 |
| myo-inositol | 87.2 | 93.5 |
| N-acetylserine | 80.4 | 79.9 |

C. Chromatography Method 3 and MS/MS Method 3

The analytical performance of the combination of Chromatography Method 3 and MS/MS Method 3 resulted in the quantitation of a plurality of up to nine analytes selected from the group consisting of N-acetylthreonine, phenylacetylglutamine, tryptophan, creatinine, N-acetylalanine, 3-methylhistidine, trans-4-hydroxyproline, kynurenine, and urea in a single injection with a run time of 7.0 minutes.

The precision of the method for measuring a plurality of nine analytes was evaluated in a representative lot of plasma and serum. Twelve replicates for plasma and six replicates for serum were analyzed over three runs. The inter-run precision was less than 6.2% in plasma and less than 6.0% in serum. The results are presented in Table 15.

TABLE 15

Inter-run Precision for a Plurality of Analytes in Plasma and Serum.

| | Plasma | | Serum | |
|---|---|---|---|---|
| Analyte | Inter-Run Mean (µg/mL) (n = 36) | Inter-Run % RSD (n = 36) | Inter-Run Mean (µg/mL) (n = 18) | Inter-Run % RSD (n = 18) |
| N-acetylthreonine | 0.0717 | 4.9 | 0.0847 | 4.4 |
| phenylacetylglutamine | 0.252 | 4.5 | 0.64 | 2.2 |
| tryptophan | 11.0 | 4.2 | 15.04 | 4.1 |
| creatinine | 7.880 | 2.8 | 9.72 | 3.3 |
| N-acetylalanine | 0.160 | 6.2 | 0.20 | 6.0 |
| 3-methylhistidine | 0.891 | 5.7 | 1.13 | 4.1 |
| trans-4-hydroxyproline | 1.97 | 4.8 | 2.08 | 4.2 |
| kynurenine | 0.228 | 3.9 | 0.437 | 4.1 |
| urea | 209 | 3.1 | 481 | 2.2 |

The precision and accuracy at the LLOQ were evaluated. The signal-to-noise ratio for every analyte was greater than 5:1. Six replicates of the LLOQ samples were analyzed in three runs. A total of 18 replicates of the LLOQ were included in the inter-day % RSD and accuracy calculations for each analyte for each matrix. Inter-run precision was less than 14.4% for plasma and less than 9.5% for serum. Inter-run accuracy was between 91.7-102% for plasma and between 92.6-101.9% for serum. The data are shown in Table 16.

TABLE 16

Inter-Run Precision and Accuracy at the LLOQ.

| | Plasma (n = 18) | | | Serum (n = 18) | | |
|---|---|---|---|---|---|---|
| Analyte | Inter-Run Mean (µg/mL) | Inter-Run % RSD | Inter-Run Accuracy (%) | Inter-Run Mean (µg/mL) | Inter-Run % RSD | Inter-Run Accuracy (%) |
| N-acetylthreonine | 0.00754 | 8.4 | 101 | 0.008 | 7.9 | 95.5 |
| phenylacetylglutamine | 0.0124 | 4.8 | 98.9 | 0.0127 | 8.0 | 98.2 |
| tryptophan | 0.2 | 14.4 | 92.8 | 0.206 | 8.0 | 96.9 |
| creatinine | 0.176 | 4 | 101 | 0.188 | 7.6 | 92.6 |
| N-acetylalanine | 0.007 | 7.2 | 98.4 | 0.0078 | 9.1 | 96.0 |
| 3-methylhistidine | 0.0409 | 13.5 | 102 | 0.081 | 4.9 | 99.13 |
| trans-4-hydroxyproline | 0.0493 | 5.5 | 98.6 | 0.050 | 9.5 | 100.17 |
| kynurenine | 0.0229 | 6.2 | 91.7 | 0.025 | 7.3 | 101.9 |
| urea | 9 | 7.6 | 93.4 | 10.5 | 7.4 | 94.6 |

In order to assess the recovery of analytes during the extraction, QC samples in serum and plasma were fortified with known concentrations of analytes. Six replicates of the spiked QC samples were extracted and analyzed along with regular QC samples in triplicate. Recovery of the spiked amount was calculated after subtraction of the amount in the spiked QC samples. The recoveries for the nine analytes were determined to be 86.1% to 96.4% in plasma and 91.5% to 98.3% in serum for the nine analytes. The data are presented in Table 17.

TABLE 17

Recovery of Analytes

| Analyte | Plasma Average % Recovery | Serum Average % Recovery |
| --- | --- | --- |
| N-acetylthreonine | 89.9 | 94.3 |
| phenylacetylglutamine | 91.8 | 94.8 |
| tryptophan | 96.4 | 91.5 |
| creatinine | 93.6 | 93.7 |
| N-acetylalanine | 89.5 | 95.4 |
| 3-methylhistidine | 86.1 | 98.3 |
| trans-4-hydroxyproline | 86.3 | 93.7 |
| kynurenine | 86.6 | 92.7 |
| urea | 96.1 | 93.2 |

D. Chromatography Method 4 and MS/MS Method 4

The analytical performance of the combination of Chromatography Method 4 and MS/MS Method 4 resulted in the quantitation of a plurality of up to three analytes selected from the group consisting of tryptophan, C-glycosyltryptophan, and 3-indoxyl sulfate in a single injection with a run time of 3.30 minutes.

The precision of the method for measuring tryptophan and/or 3-indoxyl sulfate was evaluated in a representative lot of plasma and serum. Twelve replicates for plasma and six replicates for serum were analyzed over three runs. The inter-run precision was less than 4.4% in plasma and less than 5.8% in serum. The results are presented in Table 18.

TABLE 18

Inter-run Precision for a Plurality of Analytes in Plasma and Serum.

| | Plasma | | Serum | |
| --- | --- | --- | --- | --- |
| Analyte | Inter-Run Mean (µg/mL) (n = 36) | Inter-Run % RSD (n = 36) | Inter-Run Mean (µg/mL) (n = 18) | Inter-Run % RSD (n = 18) |
| tryptophan | 10.8 | 3.2 | 14.5 | 5.8 |
| 3-indoxyl sulfate | 0.6 | 4.4 | 0.865 | 5.8 |

The precision and accuracy at the LLOQ were evaluated. The signal-to-noise ratio for every analyte was greater than 5:1. Six replicates of the LLOQ samples were analyzed in three runs. A total of 18 replicates of the LLOQ were included in the inter-day % RSD and accuracy calculations for each analyte for each matrix. Inter-run precision was less than 7.8% for plasma and less than 8.3% for serum. Inter-run accuracy was between 106-107% for plasma and between 93.5-94.2% for serum. The data are shown in Table 19.

TABLE 19

Inter-Run Precision and Accuracy at the LLOQ.

| | Plasma (n = 18) | | | Serum (n = 18) | | |
| --- | --- | --- | --- | --- | --- | --- |
| Analyte | Inter-Run Mean (µg/mL) | Inter-Run % RSD | Inter-Run Accuracy (%) | Inter-Run Mean (µg/mL) | Inter-Run % RSD | Inter-Run Accuracy (%) |
| tryptophan | 0.212 | 7.8 | 106 | 0.212 | 8.3 | 94.2 |
| 3-indoxyl sulfate | 0.0 | 4.3 | 107 | 0.0319 | 7.7 | 93.5 |

In order to assess the recovery of analytes during the extraction, QC samples in serum and plasma were fortified with known concentrations of analytes. Six replicates of the spiked QC samples were extracted and analyzed along with regular QC samples in triplicate. Recovery of the spiked amount was calculated after subtraction of the amount in the spiked QC samples. The recovery for tryptophan was determined to be 97.7% in plasma and 90.9% in serum; the recovery for 3-indoxylsulfate was determined to be 94.3% in plasma and 96.3% in serum.

E. Chromatography Method 6 and MS/MS Method 5

The analytical performance of the combination of Chromatography Method 6 and MS/MS Method 5 resulted in the quantitation of a plurality of up to ten analytes selected from the group consisting of meso-erythritol, D-arabitol, inositol, 3-indoxyl sulfate, L-tryptophan, phenylacetylglutamine, creatinine, pseudouridine, N-acetylthreonine, and N-acetylserine in a single injection with a run time of 7.0 minutes.

The precision of the method for measuring a plurality of ten analytes was evaluated in representative lots of plasma and serum. Twelve replicates for plasma and serum were analyzed over three runs. The results are presented in Table 20.

TABLE 20

Inter-run Precision for a Plurality of Analytes in Plasma and Serum.

| | Plasma | | Serum | |
|---|---|---|---|---|
| Analyte | Inter-Run Mean (µg/mL) (n = 36) | Inter-Run % RSD (n = 36) | Inter-Run Mean (µg/mL) (n = 36) | Inter-Run % RSD (n = 36) |
| meso-erythritol | 0.542 | 9.8 | 0.687 | 7.6 |
| Arabitol | 0.424 | 10.1 | 0.463 | 8.1 |
| Inositol | 3.59 | 6.2 | 3.57 | 6 |
| 3-indoxyl sulfate | 1.19 | 31.7 | 1 | 26.1 |
| tryptophan | 11.5 | 3.4 | 13.6 | 3.2 |
| phenylacetylglutamine | 0.234 | 9.3 | 0.196 | 12.4 |
| creatinine | 8.37 | 4.7 | 8.42 | 6.3 |
| pseudouridine | 0.671 | 7.2 | 0.693 | 6.9 |
| N-acetylthreonine | 0.06655 | 5.6 | 0.0647 | 7.3 |
| N-acetylserine | 0.118 | 8.6 | 0.125 | 11.3 |

In order to assess the recovery of analytes during the extraction, QC samples in serum and plasma were fortified with known concentrations of analytes. Six replicates of the spiked QC samples were extracted and analyzed along with six regular QC replicate samples in plasma and serum. Recovery of the spiked amount was calculated after subtraction of the amount in the spiked QC samples. The recovery for the ten analytes was determined to be greater than 90% in plasma and serum.

F. Chromatography Method 7 and MS/MS Method 5

The analytical performance of the combination of Chromatography Method 7 and MS/MS Method 5 resulted in the quantitation of a plurality of up to five analytes selected from the group consisting of arabitol, phenylacetylglutamine, creatinine, pseudouridine, N-acetylthreonine in a single injection with a run time of 2.7 minutes.

The precision of the method for measuring a plurality of five analytes was evaluated in representative lots of plasma and serum. Twelve replicates for plasma and serum were analyzed over three runs. The results are presented in Table 21.

TABLE 21

Inter-run Precision for a Plurality of Analytes in Plasma and Serum.

| | Plasma | | Serum | |
|---|---|---|---|---|
| Analyte | Inter-Run Mean (µg/mL) (n = 36) | Inter-Run % RSD (n = 36) | Inter-Run Mean (µg/mL) (n = 36) | Inter-Run % RSD (n = 36) |
| Arabitol | 0.488 | 12.2 | 0.527 | 10 |
| phenylacetylglutamine | 0.249 | 8 | 0.199 | 10.8 |
| creatinine | 8.32 | 3.7 | 8.4 | 3.2 |
| pseudouridine | 0.662 | 8.3 | 0.697 | 7.5 |
| N-acetylthreonine | 0.0653 | 7.2 | 0.0621 | 6 |

In order to assess the recovery of analytes during the extraction, QC samples in serum and plasma were fortified with known concentrations of analytes. Six replicates of the spiked QC samples were extracted and analyzed along with six regular QC replicate samples in plasma and serum. Recovery of the spiked amount was calculated after subtraction of the amount in the spiked QC samples. The recovery of the analytes phenylacetylglutamine, creatinine, and pseudouridine was determined to be greater than 90% in plasma and serum; the recovery of the analytes arabitol and N-acetylthreonine were determined to be greater than 85%.

G. Chromatography Method 8 and MS/MS Method 5

The analytical performance of the combination of Chromatography Method 8 and MS/MS Method 5 resulted in the quantitation of a plurality of up to six analytes selected from the group consisting of myo-inositol, tryptophan, phenylacetylglutamine, creatinine, pseudouridine, N-acetylthreonine in a single injection with a run time of 3.2 minutes.

The precision of the method for measuring a plurality of six analytes was evaluated in representative lots of plasma and serum. Twelve replicates for plasma and serum were analyzed over three runs. The results are presented in Table 22.

TABLE 22

Inter-run Precision for a Plurality of Analytes in Plasma and Serum.

| | Plasma | | Serum | |
|---|---|---|---|---|
| Analyte | Inter-Run Mean (µg/mL) (n = 36) | Inter-Run % RSD (n = 36) | Inter-Run Mean (µg/mL) (n = 36) | Inter-Run % RSD (n = 36) |
| Inositol | 3.53 | 7.6 | 3.59 | 6.6 |
| tryptophan | 11.6 | 2.1 | 13.3 | 3.5 |
| phenylacetylglutamine | 0.257 | 10.5 | 0.208 | 9.7 |
| creatinine | 8.33 | 3.9 | 8.42 | 4 |
| pseudouridine | 0.658 | 7.5 | 0.698 | 6.6 |
| N-acetylthreonine | 0.066 | 8 | 0.0633 | 8.2 |

In order to assess the recovery of analytes during the extraction, QC samples in serum and plasma were fortified with known concentrations of analytes. Six replicates of the spiked QC samples were extracted and analyzed along with six regular QC replicate samples in plasma and serum. Recovery of the spiked amount was calculated after subtraction of the amount in the spiked QC samples. The recovery of the six analytes was determined to be greater than 90% in plasma and serum.

APPENDIX A

TABLE A

Combinations of 2, 3, and 4 analtyes are shown for Method 1
Combinations of 2, 3, 4, and 5 analytes are shown for Method 5
Combinations of 2 analytes are shown for Methods 2, 3, 4, 6, 7, and 8

| | pseudouridine | N-acetylthreonine | phenylacetylglutamine | tryptophan | creatinine | meso-erythritol | arabitol | myo-inositol | N-acetylserine | N-acetylalanine | 3-methylhistidine | trans-4-hydroxyproline | kymurenine | urea | 3-indoxylsulfate | C-glycosyltryptophan | TMAP |
|---|---|---|---|---|---|---|---|---|---|---|---|---|---|---|---|---|---|
| Combination 1 | X | X | | | | | | | | | | | | | | | |
| Combination 2 | X | | X | | | | | | | | | | | | | | |
| Combination 3 | X | | | X | | | | | | | | | | | | | |
| Combination 4 | X | | | | X | | | | | | | | | | | | |
| Combination 5 | | X | X | | | | | | | | | | | | | | |
| Combination 6 | | X | | X | | | | | | | | | | | | | |
| Combination 7 | | X | | | X | | | | | | | | | | | | |
| Combination 8 | | | X | X | | | | | | | | | | | | | |
| Combination 9 | | | X | | X | | | | | | | | | | | | |
| Combination 10 | | | | X | X | | | | | | | | | | | | |
| Combination 11 | X | X | X | | | | | | | | | | | | | | |
| Combination 12 | X | X | | X | | | | | | | | | | | | | |
| Combination 13 | X | X | | | X | | | | | | | | | | | | |
| Combination 15 | X | | X | X | | | | | | | | | | | | | |
| Combination 16 | X | | X | | X | | | | | | | | | | | | |
| Combination 14 | X | | | X | X | | | | | | | | | | | | |
| Combination 17 | | X | X | X | | | | | | | | | | | | | |
| Combination 18 | | X | X | | X | | | | | | | | | | | | |
| Combination 19 | | X | | X | X | | | | | | | | | | | | |
| Combination 20 | | | X | X | X | | | | | | | | | | | | |
| Combination 21 | X | X | X | X | | | | | | | | | | | | | |
| Combination 22 | X | | X | X | X | | | | | | | | | | | | |
| Combination 23 | | X | X | X | X | | | | | | | | | | | | |
| Combination 24 | X | X | | X | X | | | | | | | | | | | | |

| | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| Combination 25 | X | X | X | X | | | | | | | | | | | | | |
| Combination 26 | X | | | | X | | | | | | | | | | | | |
| Combination 27 | X | | | | | X | | | | | | | | | | | |
| Combination 28 | X | | | | | | X | | | | | | | | | | |
| Combination 29 | X | | | | | | | X | | | | | | | | | |
| Combination 30 | | X | | | X | | | | | | | | | | | | |
| Combination 31 | | X | | | | X | | | | | | | | | | | |
| Combination 32 | | X | | | | | X | | | | | | | | | | |
| Combination 33 | | X | | | | | | X | | | | | | | | | |
| Combination 34 | | | | | X | X | | | | | | | | | | | |
| Combination 35 | | | | | X | | X | | | | | | | | | | |
| Combination 36 | | | | | X | | | X | | | | | | | | | |
| Combination 37 | | | | | | X | X | | | | | | | | | | |
| Combination 38 | | | | | | X | | X | | | | | | | | | |
| Combination 39 | | | | | | | X | X | | | | | | | | | |
| Combination 40 | | X | | | | | | | X | | | | | | | | |
| Combination 41 | | X | | | | | | | | X | | | | | | | |
| Combination 42 | | X | | | | | | | | | X | | | | | | |
| Combination 43 | | X | | | | | | | | | | X | | | | | |
| Combination 44 | | X | | | | | | | | | | | X | | | | |
| Combination 45 | | | X | | | | | | X | | | | | | | | |
| Combination 46 | | | X | | | | | | | X | | | | | | | |
| Combination 47 | | | X | | | | | | | | X | | | | | | |
| Combination 48 | | | X | | | | | | | | | X | | | | | |
| Combination 49 | | | X | | | | | | | | | | X | | | | |
| Combination 50 | | | | X | | | | | X | | | | | | | | |
| Combination 51 | | | | X | | | | | | X | | | | | | | |
| Combination 52 | | | | X | | | | | | | X | | | | | | |
| Combination 53 | | | | X | | | | | | | | X | | | | | |
| Combination 54 | | | | X | | | | | | | | | X | | | | |
| Combination 55 | | | | | X | | | | X | | | | | | | | |
| Combination 56 | | | | | X | | | | | X | | | | | | | |
| Combination 57 | | | | | X | | | | | | X | | | | | | |
| Combination 58 | | | | | X | | | | | | | X | | | | | |
| Combination 59 | | | | | X | | | | | | | | X | | | | |
| Combination 60 | | | | | | | | | X | X | | | | | | | |
| Combination 61 | | | | | | | | | X | | X | | | | | | |
| Combination 62 | | | | | | | | | X | | | X | | | | | |
| Combination 63 | | | | | | | | | X | | | | X | | | | |
| Combination 64 | | | | | | | | | | X | X | | | | | | |
| Combination 65 | | | | | | | | | | X | | X | | | | | |
| Combination 66 | | | | | | | | | | X | | | X | | | | |
| Combination 67 | | | | | | | | | | | X | X | | | | | |
| Combination 68 | | | | | | | | | | | X | | X | | | | |
| Combination 69 | | | | | | | | | | | | X | X | | | | |
| Combination 70 | | | X | | | | | | | | | | | | X | | |
| Combination 71 | | | X | | | | | | | | | | | | | X | |

| | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| Combination 72 | | | | | | | | | | | | | | | | X | X | |
| Combination 73 | X | X | | | | | | | | | | | | | | | | |
| Combination 74 | X | | X | | | | | | | | | | | | | | | |
| Combination 75 | X | | | X | | | | | | | | | | | | | | |
| Combination 76 | X | | | | X | | | | | | | | | | | | | |
| Combination 77 | X | | | | | | | | | | | | | | | | | X |
| Combination 78 | | X | X | | | | | | | | | | | | | | | |
| Combination 79 | | X | | X | | | | | | | | | | | | | | |
| Combination 80 | | X | | | X | | | | | | | | | | | | | |
| Combination 81 | | X | | | | | | | | | | | | | | | | X |
| Combination 82 | | | X | X | | | | | | | | | | | | | | |
| Combination 83 | | | X | | X | | | | | | | | | | | | | |
| Combination 84 | | | X | | | | | | | | | | | | | | | X |
| Combination 85 | | | | X | X | | | | | | | | | | | | | |
| Combination 86 | | | | X | | | | | | | | | | | | | | X |
| Combination 87 | | | | | X | | | | | | | | | | | | | X |
| Combination 88 | X | X | X | | | | | | | | | | | | | | | |
| Combination 89 | X | X | | X | | | | | | | | | | | | | | |
| Combination 90 | X | X | | | X | | | | | | | | | | | | | |
| Combination 91 | X | X | | | | | | | | | | | | | | | | X |
| Combination 92 | X | | X | X | | | | | | | | | | | | | | |
| Combination 93 | X | | X | | X | | | | | | | | | | | | | |
| Combination 94 | X | | X | | | | | | | | | | | | | | | X |
| Combination 95 | X | | | X | X | | | | | | | | | | | | | |
| Combination 96 | X | | | X | | | | | | | | | | | | | | X |
| Combination 97 | | | X | X | | | | | | | | | | | | | | X |
| Combination 98 | | X | X | X | | | | | | | | | | | | | | |
| Combination 99 | | X | X | | X | | | | | | | | | | | | | |
| Combination 100 | | X | X | | | | | | | | | | | | | | | X |
| Combination 101 | | X | | X | X | | | | | | | | | | | | | |
| Combination 102 | | X | | X | | | | | | | | | | | | | | X |
| Combination 103 | | X | | | X | | | | | | | | | | | | | X |
| Combination 104 | | | X | X | X | | | | | | | | | | | | | |
| Combination 105 | | | X | X | | | | | | | | | | | | | | X |
| Combination 106 | | | X | | X | | | | | | | | | | | | | X |
| Combination 107 | | | | X | X | | | | | | | | | | | | | X |
| Combination 108 | X | X | X | X | | | | | | | | | | | | | | |
| Combination 109 | X | X | X | | | | | | | | | | | | | | | X |
| Combination 110 | X | X | X | | X | | | | | | | | | | | | | |
| Combination 111 | X | X | | X | X | | | | | | | | | | | | | |
| Combination 112 | X | X | | X | | | | | | | | | | | | | | X |
| Combination 113 | X | X | | | X | | | | | | | | | | | | | X |
| Combination 114 | X | | X | X | X | | | | | | | | | | | | | |
| Combination 115 | X | | X | X | | | | | | | | | | | | | | X |
| Combination 116 | X | | X | | X | | | | | | | | | | | | | X |
| Combination 117 | X | | | X | X | | | | | | | | | | | | | X |
| Combination 118 | | X | X | X | X | | | | | | | | | | | | | |

| | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Combination 119 | | X | X | X | | | | | | | | | | | | X |
| Combination 120 | | X | X | | X | | | | | | | | | | | X |
| Combination 121 | | | X | X | X | | | | | | | | | | | X |
| Combination 122 | | X | | X | X | | | | | | | | | | | X |
| Combination 123 | X | X | X | X | X | | | | | | | | | | | |
| Combination 124 | X | X | X | X | | | | | | | | | | | | X |
| Combination 125 | X | X | X | | X | | | | | | | | | | | X |
| Combination 126 | X | X | | X | X | | | | | | | | | | | X |
| Combination 127 | X | | X | X | X | | | | | | | | | | | X |
| Combination 128 | | X | X | X | X | | | | | | | | | | | X |
| Combination 129 | X | X | | | | | | | | | | | | | | |
| Combination 130 | X | | X | | | | | | | | | | | | | |
| Combination 131 | X | | | X | | | | | | | | | | | | |
| Combination 132 | X | | | | X | | | | | | | | | | | |
| Combination 133 | X | | | | | X | | | | | | | | | | |
| Combination 134 | X | | | | | | X | | | | | | | | | |
| Combination 135 | X | | | | | | | X | | | | | | | | |
| Combination 136 | X | | | | | | | | X | | | | | | | |
| Combination 137 | X | | | | | | | | | | | | | | X | |
| Combination 138 | | X | X | | | | | | | | | | | | | |
| Combination 139 | | X | | X | | | | | | | | | | | | |
| Combination 140 | | X | | | X | | | | | | | | | | | |
| Combination 141 | | X | | | X | | | | | | | | | | | |
| Combination 142 | | X | | | | X | | | | | | | | | | |
| Combination 143 | | X | | | | | X | | | | | | | | | |
| Combination 144 | | X | | | | | | X | | | | | | | | |
| Combination 145 | | X | | | | | | | | | | | | | X | |
| Combination 146 | | | X | X | | | | | | | | | | | | |
| Combination 147 | | | X | | X | | | | | | | | | | | |
| Combination 148 | | | X | | X | | | | | | | | | | | |
| Combination 149 | | | X | | | X | | | | | | | | | | |
| Combination 150 | | | X | | | | X | | | | | | | | | |
| Combination 151 | | | X | | | | | X | | | | | | | | |
| Combination 152 | | | X | | | | | | | | | | | | X | |
| Combination 153 | | | | X | X | | | | | | | | | | | |
| Combination 154 | | | | X | | X | | | | | | | | | | |
| Combination 155 | | | | X | | | X | | | | | | | | | |
| Combination 156 | | | | X | | | | X | | | | | | | | |
| Combination 157 | | | | X | | | | | X | | | | | | | |
| Combination 158 | | | | X | | | | | | | | | | | X | |
| Combination 159 | | | | | X | X | | | | | | | | | | |
| Combination 160 | | | | | X | | X | | | | | | | | | |
| Combination 161 | | | | | X | | | X | | | | | | | | |
| Combination 162 | | | | | X | | | | X | | | | | | | |
| Combination 163 | | | | | X | | | | | | | | | | X | |
| Combination 164 | | | | | | X | X | | | | | | | | | |
| Combination 165 | | | | | | X | | X | | | | | | | | |

| | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Combination 166 | | | | | X | | X | | | | | | | | | |
| Combination 167 | | | | | X | | | | | | | | | X | | |
| Combination 168 | | | | | | X | X | | | | | | | | | |
| Combination 169 | | | | | | X | | X | | | | | | | | |
| Combination 170 | | | | | | X | | | | | | | | X | | |
| Combination 171 | | | | | | | X | X | | | | | | | | |
| Combination 172 | | | | | | | X | | | | | | | X | | |
| Combination 173 | | | | | | | | X | | | | | | X | | |
| Combination 174 | X | X | | | | | | | | | | | | | | |
| Combination 175 | X | | X | | | | | | | | | | | | | |
| Combination 176 | X | | | X | | | | | | | | | | | | |
| Combination 177 | X | | | | X | | | | | | | | | | | |
| Combination 178 | | X | X | | | | | | | | | | | | | |
| Combination 179 | | X | | X | | | | | | | | | | | | |
| Combination 180 | | X | | | X | | | | | | | | | | | |
| Combination 181 | | X | | X | | | | | | | | | | | | |
| Combination 182 | | X | | | X | | | | | | | | | | | |
| Combination 183 | | | | X | X | | | | | | | | | | | |
| Combination 184 | X | X | | | | | | | | | | | | | | |
| Combination 185 | X | | X | | | | | | | | | | | | | |
| Combination 186 | X | | | X | | | | | | | | | | | | |
| Combination 187 | X | | | X | | | | | | | | | | | | |
| Combination 188 | X | | | | | X | | | | | | | | | | |
| Combination 189 | | X | X | | | | | | | | | | | | | |
| Combination 190 | | X | | X | | | | | | | | | | | | |
| Combination 191 | | X | | X | | | | | | | | | | | | |
| Combination 192 | | X | | | | X | | | | | | | | | | |
| Combination 193 | | | X | X | | | | | | | | | | | | |
| Combination 194 | | | X | | X | | | | | | | | | | | |
| Combination 195 | | | X | | | X | | | | | | | | | | |
| Combination 196 | | | | X | X | | | | | | | | | | | |
| Combination 197 | | | | X | | X | | | | | | | | | | |
| Combination 198 | | | | | X | X | | | | | | | | | | |

What is claimed:

1. A method for detecting and determining in a sample the amount of five or more kidney function analytes, the method comprising:
   a) purifying the sample by liquid chromatography;
   b) subjecting the purified sample to an ionization source under conditions suitable to produce one or more ions detectable by mass spectrometry from each of the five or more of the analytes selected from the group consisting of N-acetylthreonine, TMAP, phenylacetylglutamine, tryptophan, creatinine, N-acetylalanine, 3-methylhistidine, trans-4-hydroxyproline, kynurenine, urea, and pseudouridine, wherein the analytes are not derivatized prior to ionization;
   c) measuring, by tandem mass spectrometry operated in positive mode in a single injection, the amount of the one or more ions from each of the five or more analytes, wherein the one or more ions used to determine the amount of each of the five or more analytes is one or more ions selected from the ions in Tables 3 and 5; wherein an eluent from the liquid chromatography step is directly and automatically introduced into an electrospray source of the mass spectrometer; and
   d) using the measured amount of the one or more ions to determine the amount of each of the five or more analytes in the sample.

2. The method of claim 1, wherein the amount of six or more analytes is determined.

3. The method of claim 1, wherein said liquid chromatography is selected from the group consisting of high performance liquid chromatography, ultra high performance liquid chromatography, and turbulent flow liquid chromatography.

4. The method of claim 1, wherein an internal standard is used to determine the amount of the five or more analytes in the sample.

5. The method of claim 4, wherein the internal standard comprises an isotopically labeled analogue of at least one of the five or more analytes to be measured.

6. The method of claim 1, wherein the run time is 7 minutes or less.

7. The method of claim 6, wherein the run time is 4 minutes or less.

8. The method of claim 3, wherein said ultra high performance liquid chromatography is conducted using hydrophilic interaction chromatography (HILIC).

9. The method of claim 1, wherein five of the five or more analytes comprise N-acetylthreonine, phenylacetylglutamine, tryptophan, creatinine, and pseudouridine.

10. The method of claim 9, wherein the coefficient of variation over 40 samples is equal to or less than 6.5% for each of the five analytes when the sample is plasma.

11. The method of claim 1, wherein nine of the five or more analytes comprise N-acetylthreonine, phenylacetylglutamine, tryptophan, creatinine, N-acetylalanine, 3-methylhistidine, trans-4-hydroxyproline, kynurenine, and urea.

12. The method of claim 11, wherein the coefficient of variation over 12 samples is equal to or less than 14.5% for each of the nine analytes when the sample is plasma.

* * * * *